(12) United States Patent
Wu et al.

(10) Patent No.: US 10,851,370 B1
(45) Date of Patent: Dec. 1, 2020

(54) HOMOLOGOUS RECOMBINATION DIRECTED GENOME EDITING IN EUKARYOTES

(71) Applicant: PILLARGO, INC., San Diego, CA (US)

(72) Inventors: Ying Wu, San Diego, CA (US); Jiagang Zhao, San Diego, CA (US)

(73) Assignee: PILLARGO, INC., San Diego, CA (US)

( * ) Notice: Subject to any disclaimer, the term of this patent is extended or adjusted under 35 U.S.C. 154(b) by 0 days.

(21) Appl. No.: 16/556,054

(22) Filed: Aug. 29, 2019

Related U.S. Application Data

(60) Provisional application No. 62/871,495, filed on Jul. 8, 2019.

(51) Int. Cl.
| | | |
|---|---|---|
| *C12N 15/85* | (2006.01) | |
| *C12N 15/11* | (2006.01) | |
| *C12N 5/071* | (2010.01) | |
| *A61K 48/00* | (2006.01) | |

(52) U.S. Cl.
CPC ............ *C12N 15/11* (2013.01); *C12N 5/0602* (2013.01); *C12N 15/85* (2013.01); *A61K 48/005* (2013.01); *C12N 2320/30* (2013.01); *C12N 2800/22* (2013.01)

(58) Field of Classification Search
CPC .... C12N 2800/22; C12N 15/79; C12N 15/86; C12N 15/85
See application file for complete search history.

(56) References Cited

U.S. PATENT DOCUMENTS

| | | | | |
|---|---|---|---|---|
| 2006/0141600 A1* | 6/2006 | Joshua-Tor | ............ | C07K 14/47 435/199 |
| 2017/0367280 A1 | 12/2017 | Hummel | | |
| 2019/0284547 A1 | 9/2019 | Solomon et al. | | |

FOREIGN PATENT DOCUMENTS

WO 2017139264 A1 8/2017

OTHER PUBLICATIONS

O'Green et al. Unexpected binding behaviors of bacterial Argonautes in human cells cast doubts on their use as targetable gene regulators. PLOS ONE, vol. 13, No. 3, e0193818, Mar. 27, 2018, printed as pp. 1/12-12/12, including pp. 1/11-11/11 of Supplementary Information. (Year: 2018).*

Javidi-Parsijani et al. No evidence of genome editing activity from Natronobacterium gregoryi Argonaute (NgAgo) in human cells. PLOS ONE, vol. 12, No. 5, e0177444, May 11, 2017, printed as pp. 1/14-14/14. (Year: 2017).*

Khin et al. No evidence for genome editing in mouse zygotes and HEK293T human cell line using the DNA-guided Natronobacterium gregoryi Argonaute (NgAgo). PLOS ONE, vol. 12, No. 6, e0178768, Jun. 13, 2017, printed as pp. 1/10-10/10. (Year: 2017).*

Blow, N. To edit or not: The NgAgo story. BioTechniques, vol. 61, pp. 172-174, Oct. 2016. (Year: 2016).*

Lee et al. Failure to detect DNA-guided genome editing using Natronobacterium gregoryi Argonaute. Nature Biotechnology, vol. 35, No. 1, pp. 17-18, Jan. 2017, published online Nov. 28, 2016, including pp. 1/24-24/24 of Supplementary Information. (Year: 2017).*

Cox et al. Therapeutic genome editing: prospects and challenges. Nature Medicine, vol. 21, No. 2, pp. 121-131, Feb. 2015. (Year: 2015).*

Fu et al., "The prokaryotic Argonaute proteins enhance homology sequence-directed recombination in bacteria", Nucleic Acids Research, 47(7), 3568-3579, Jan. 2019.

Solomon et al., "NgAgo-enhanced homologous recombination in *E. coli* is mediated by DNA endonuclease activity", bioRxiv preprint first posted online Apr. 4, 2019; doi: http://dx.doi.org/10.1101/597237.

* cited by examiner

*Primary Examiner* — Jennifer Dunston
(74) *Attorney, Agent, or Firm* — Maschoff Brennan; Brent A. Johnson; Yuefen Zhou

(57) ABSTRACT

Disclosed herein are synthetic nucleic acids comprising a nucleic acid sequence that encodes a codon-Adapted Nuclear Argonaute protein (ANAGO) that is a species-specific to a eukaryote, and compositions comprising ANAGO and donor molecules for use in homologous recombination directed targeted gene editing in the eukaryote.

11 Claims, 8 Drawing Sheets
Specification includes a Sequence Listing.

FIG. 1C

| INDEL | CONTRIBUTION | SEQUENCE | |
|---|---|---|---|
| 0 | 91.4% | GCCGGGGATACCCTCACCAAGATCCT | GCATGTCTTCCATGGCCTTCTTCCTGGTGAAGATGAGTGGCG |
| HDR — | 7.1% | GCCGGGGATACCCTCACCAAGATCCT | GCATGCCTTCCATGGCCTTCTTCCTGGTGAAGATGAGTGGCG |
| -1 | 0.6% | GCCGGGGATACCCTCACCAAGATCC- | GCATGTCTTCCATGGCCTTCTTCCTGGTGAAGATGAGTGGCG |
| -17 | 0.3% | GCCGGGGATAC--------------- | ----------TGTCTTCCATGGCCTTCTTCCTGGTGAAGATGAGTGGC |
| +1 | 0.1% | GCCGGGGATACCCTCACCAAGATCCT | NGCATGTCTTCCATGGCCTTCTTCCTGGTGAAGATGAGTGGC |
| +12 | 0.1% | GCCGGGGATACCCTCACCAAGATCCT | NNNNNNNNNNNNGCATGTCTTCCATGGCCTTCCTGGTGA |
| -16 | 0.1% | GCCGGGGATACCCTCACCAAGATC-- | -------------GCCTTCTTCCTGGTGAAGATGAGTGGCG |
| -9 | 0.1% | GCCGGGGATACCCTCACC-------- | --CATGTCTTCCATGGCCTTCTTCCTGGTGAAGATGAGTGGCG |
| -13 | 0% | GCCGGGGATACCCTCACCC------- | --ATGTCTTCCATGGCCTTCTTCCTGGTGAAGATGAGTGGCG |
| -29 | 0% | GCCGGGGATAC--------------- | ------------CCTTCTTCCATGGCCTTCTTCCTGGCTTCCTGGTGAAGATGAGTGGCG |
| +4 | 0% | GCCGGGGATACCCTCACCAAGATCCT | NNNNGCATGTCTTCCATGGCCTTCCTGGCTTCCTGGTGAAGATGAGT |

FIG. 1D

| INDEL | CONTRIBUTION | SEQUENCE | |
|---|---|---|---|
| 0 | 97% | GTTGCCCCATGTCGACTACATCGAG | GAGGACTCCTCTGTCTTTGCCCAGAGCATCCCGTGGAACCTGGAGCGGAT |
| HDR — | 3% | GTTGCCCCATGTCGACTAGTAG | GAGGACTCCTCTGTCTTGCCCAGAGCATCCCGTGGAACCTGGAGCGGAT |

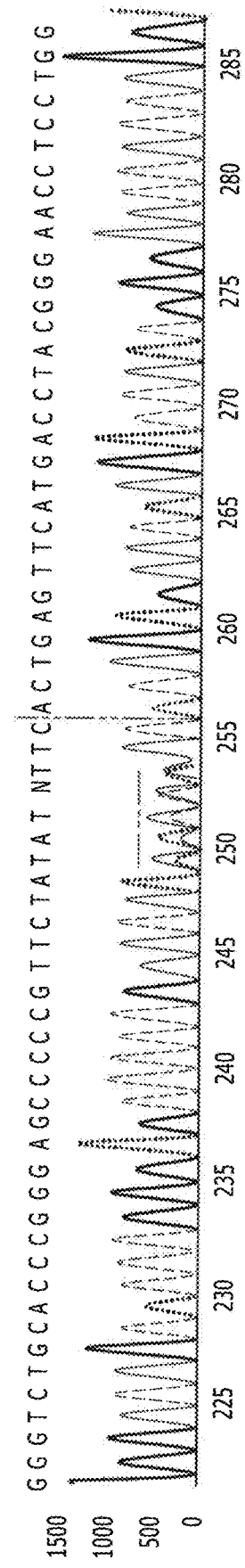

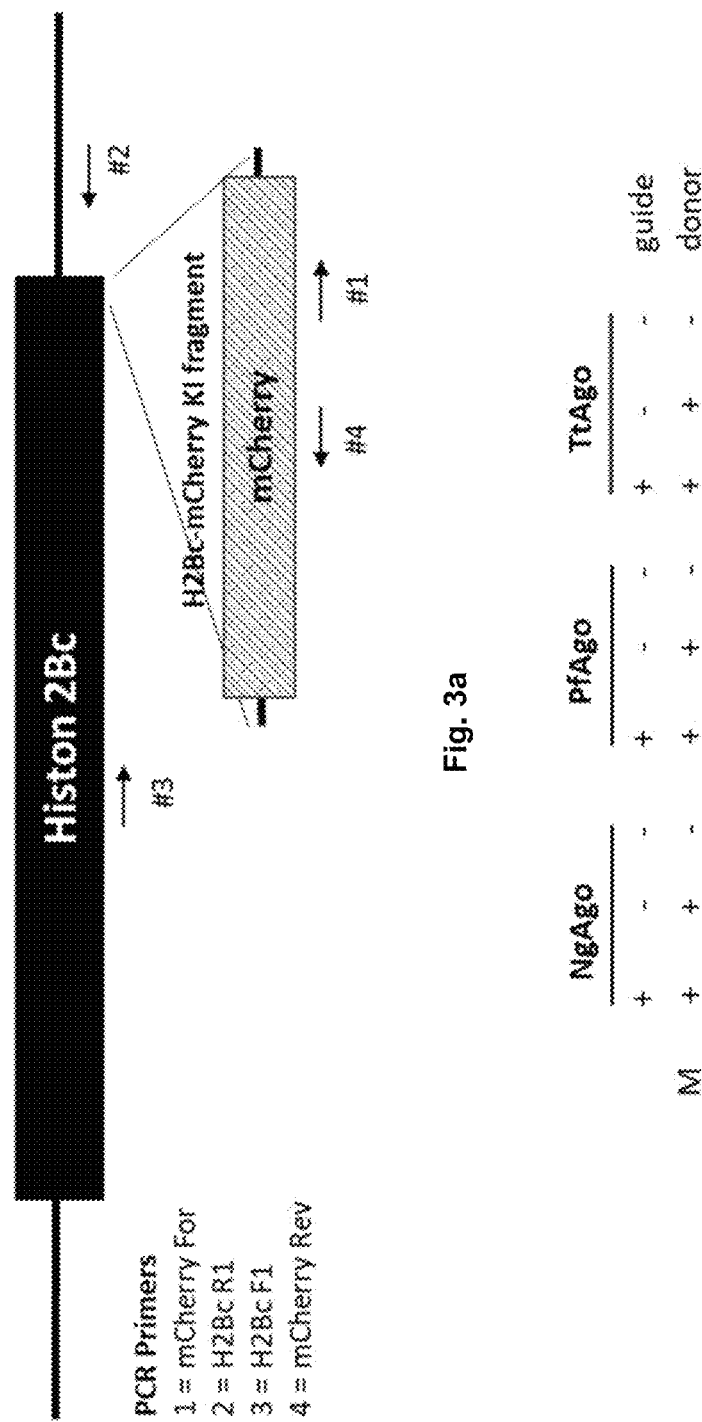
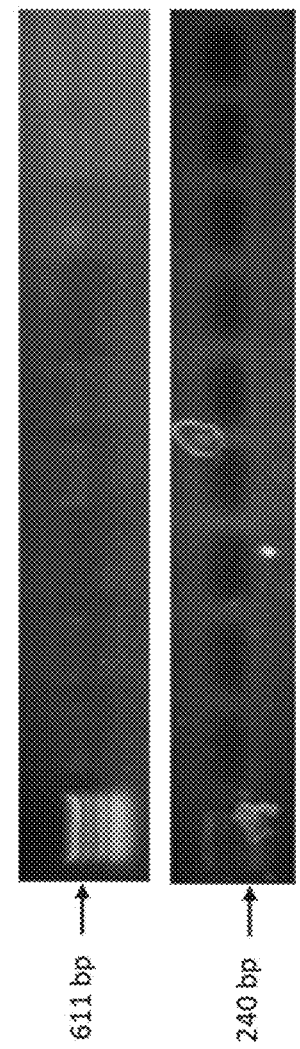
Fig. 3a
Fig. 3b

US 10,851,370 B1

HOMOLOGOUS RECOMBINATION DIRECTED GENOME EDITING IN EUKARYOTES

CROSS-REFERENCE TO RELATED APPLICATION

This application claims benefit of U.S. Provisional Application No. 62/871,495, filed Jul. 8, 2019, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Aug. 28, 2019, is named P3651_10001US02_SL.txt and is 24,380 bytes in size.

FIELD

The present disclosure relates to compositions comprising synthetic nucleic acids comprising human codons that facilitate genome editing. The present invention also relates to methods of using the compositions comprising synthetic nucleic acids for genetic engineering in human beings and other mammals BACKGROUND Genome editing has offered a powerful tool and unprecedented opportunity to study gene functions and to fight diseases by introducing a targeted genomic sequence change at a specific locus of a living cell or organism. Zinc finger nucleases (ZFNs), transcription activator-like effector nucleases (TALENs), and clustered regularly interspaced short palindromic repeats (CRISPR)-associated (Cas) nucleases are the ones that have been used successfully and efficiently by many laboratories. More recently, the RNA-guided endonucleases such as Cas9 and Cpf1 have gained more traction because of their relatively ease of manipulation. The user-friendly CRISPR-Cas9 is very efficient in making mutations via nonhomologous end joining (NHEJ) in human cancer cell lines such as 293T cells. It also can mediate homologous recombination (HR), but at a much lower efficiency (2-5%) in 293T cells and even lower in other biologically relevant cells such as human induced pluripotent stem cells (iPSCs).

Recently, it has been reported that it is feasible to achieve genome editing by using *Natronobacterium gregoryi* Argonaute (NgAgo) with a guide DNA oligo in human cells (Gao F, et al., (2016) Nat Biotechnol. 34(7):768-73). However, multiple labs have failed to reproduce this phenomenon claimed by Gao et al. thus far, which led to the withdrawal of this publication. Interestingly, an eye defect was observed by using an NgAgo approach in zebrafish. The phenotype was most likely caused by an NgAgo mediated gene knockdown effect, and no genetic modification was observed at the DNA level.

Argonautes use an orthogonal mechanism of immune surveillance and promise an entirely novel process for gene editing. Argonautes are a family of endonucleases that use 5' phosphorylated short single-stranded nucleic acids as guides to cleave targets. Similar to Cas9 and Cpf1, Argonautes play key roles in gene expression repression and host defense against foreign nucleic acids. While Cas9 and Cpf1 are only naturally found in prokaryotes, members of Argonaute superfamily are reported to be present in many species (from bacteria to mammals). Although most Argonautes associate with single-stranded (ss) RNAs and play a central role in RNA silencing, some Argonautes bind ssDNAs and cleave target DNAs. It appears that DNA-guided Argonaute binding does not have a specific requirement for sequence or secondary structure. Argonautes are conserved throughout the bacterial and archaeal domains of living organisms. Their major functions are likely to be involved in DNA-guided DNA-interfering host defense systems.

An ideal gene editing tool should be able to introduce a desired base change, deletion or insertion into the genome in a precise, non-bias and error-free manner. Although CRISPR/Cas systems, originally derived from a bacterial host defense mechanism, are versatile and are currently widely used, they are error-prone and sequence-biased.

SUMMARY

Disclosed herein are several novel codon-adapted Argonaute protein variants named ANAGO that are derived from microbial Argonaute proteins capable of editing a target nucleic acid sequence within a prokaryotic cell. The DNA coding sequences of these microbial argonaute proteins, such as NgAgo, PfAgo, TtAgo and MjAgo, can be reengineered and adapted with the codons that have preferential usage in eukaryotes, such as humans to generate new synthetic DNA sequences that encodes the ANAGO that are species-specific to the eukaryotes, wherein the ANAGO conserves or retains the endonuclease activities, capable of editing a target nucleic acid sequence within a eukaryotic cell. Also disclosed herein are the uses of these ANAGO and one or more homologous donor nucleic acids to mediate homologous recombination directed genome editing in eukaryotic cells, such as human cells in a guide-independent fashion. Such an ANAGO induced homologous recombination directed genome/sequence editing (AISE) in human cells can be carried out precisely with no significant off-target events detected. Such a homologous donor nucleic acid can be either single-stranded or double-stranded. Such a AISE technology can be used in gene therapy, such as treating a disease, a disorder, or a condition treatable with genome editing in eukaryotic cells, for example, treating chronic myelogenous leukemia and lowering LDL levels in blood stream.

Some embodiments comprise a synthetic nucleic acid comprising: a first nucleic acid sequence comprising about 1000 or more contiguous nucleotides, or portion thereof, wherein the first nucleic acid sequence encodes an ANAGO that is a polypeptide, capable of editing a target nucleic acid sequence within a eukaryotic cell, wherein the ANAGO is a species-specific to the eukaryote; wherein the first nucleic acid sequence is modified from a second nucleic acid sequence of a microbial species; wherein the second nucleic acid sequence comprises a coding region that is capable of encoding a microbial Argonaute protein that has endonuclease activities in prokaryotic cells; wherein the first nucleic acid sequence is modified so that some of the microbial preferred codons of the second nucleic acid sequence are replaced with codons that have preferential usage by the target eukaryotic species.

Some embodiments comprise a synthetic nucleic acid comprising a first nucleic acid sequence comprising about 1000 or more contiguous nucleotides, or portion thereof having at least 70% identity to the nucleic acid sequence of SEQ ID NO:1; SEQ ID NO:2; SEQ ID NO:3, or SEQ ID NO:4, or portion thereof, wherein the first nucleic acid sequence encodes an ANAGO that is a polypeptide, capable of editing a target nucleic acid sequence within a human cell, wherein the ANAGO is a species-specific to the human being; wherein the first nucleic acid sequence is modified from a second nucleic acid sequence of a microbial species, and wherein the second nucleic acid sequence comprises a coding region that is capable of encoding a microbial Argonaute protein that has endonuclease activities in prokaryotic cells; and wherein the first nucleic acid sequence is modified so that the microbial preferred codons of the second nucleic acid sequence are replaced with codons that have preferential usage in the target human being.

Some embodiments comprise a composition comprising a synthetic nucleic acid or an ANAGO described herein. In some embodiments, the composition is a pharmaceutical composition (e.g., a composition formulated for administration to a subject). In some embodiments, a pharmaceutical composition comprises one or more of a pharmaceutical acceptable excipient, diluent, additive or carrier.

Some embodiments comprise a method of editing a genome of a eukaryotic cell comprising: introducing into the cell (i) a species-specific ANAGO encoded by the first synthetic nucleic acid sequence or an in vitro messenger RNA transcribed by the first synthetic nucleic acid sequence described herein; and (ii) a donor nucleic acid comprising: a desired nucleic acid sequence, a 5'-flanking sequence, and a 3'-flanking sequence, wherein each of the 5'-flanking sequence and the 3'-flanking sequence are located on opposite sides of the desired nucleic acid sequence and independently comprise at least 10 consecutive nucleotides that are at least 90% identical to a target sequence located in the genome of the eukaryotic cell.

Some embodiments comprise a method of editing a genome of a human cell comprising: introducing into the human cell (i) a human ANAGO encoded by the first synthetic nucleic acid sequence comprising about 1000 or more contiguous nucleotides, or portion thereof having at least 70% identity to the nucleic acid sequence of SEQ ID NO:1; SEQ ID NO:2; SEQ ID NO:3, or SEQ ID NO:4, or portion thereof; and (ii) a donor nucleic acid comprising: a desired nucleic acid sequence, a 5'-flanking sequence, and a 3'-flanking sequence, wherein each of the 5'-flanking sequence and the 3'-flanking sequence are located on opposite sides of the desired nucleic acid sequence and independently comprise at least 10 consecutive nucleotides that are at least 90% identical to a target sequence located in the genome of the human cell.

Some embodiments include an ANAGO induced gene editing method, wherein a single or multiple donor molecules targeting different sites can be introduced into a eukaryotic cell at same time for multiplex gene editing at same time.

Some embodiments comprise a kit comprising a synthetic nucleic acid, an ANAGO, a homologous donor nucleic acid, a composition described herein, or a combination thereof.

Some embodiments comprise a kit comprising an ANAGO, such as a human ANAGO, and a homologous donor nucleic acid described herein.

Some embodiments comprise an ANAGO that is further attached to a nuclear localization signal peptide sequence (NLS) to the N-terminus of the protein in ANAGO before introducing the ANAGO into the nucleus of mammalian cells. In some embodiments, a tag sequence such as human influenza hemagglutinin (HA) tag or his tag or myc tag is also included for protein detection purposes.

Some embodiments include delivery of an ANAGO into a eukaryotic cell, such as a human cell, wherein the ANAGO and the donor nucleic acid are introduced into the cell via viral vector, electroporation, lipofection, nucleofection, nanoparticle, or microinjection.

In some embodiments, an ANAGO, such as a human ANAGO, in a protein form, or an in vitro transcribed messenger RNA, is cloned into a mammalian expression vector before introduced into a mammalian cell. The mammalian expression vector can be a plasmid, a lentiviral vector, an adeno-associated viral vector, or any viral vector.

Some embodiments include the use of the ANAGO induced gene editing technology in cancer immunotherapy, antiviral therapy, liver-targeted gene editing, and blindness treatment, etc.

Some embodiments include the use of the ANAGO induced gene editing technology for treating diseases, disorder, or conditions that are potentially treatable using gene editing in eukaryotes, such as treating cancer, e.g. chronic myelogenous leukemia; and lowering LDL levels in blood stream.

BRIEF DESCRIPTION OF THE FIGURES

The drawings illustrate embodiments of the technology and are not limiting. For clarity and ease of illustration, the drawings are not made to scale, and, in some instances, various aspects may be shown exaggerated or enlarged to facilitate an understanding of particular embodiments.

FIG. 1c shows the homology-directed replacement (HDR) analysis of sequencing result of R104C-V114A 70mer donor replacement in HEK293 cells. FIG. 1c discloses SEQ ID NOS 28-38, respectively, in order of appearance.

FIG. 1d shows the homology-directed replacement (HDR) analysis of sequencing result of Y142X-E144X 89mer donor replacement in HEK293 cells. FIG. 1d discloses SEQ ID NOS 39-40, respectively, in order of appearance.

FIG. 2b shows the homology directed replacement (HDR) analysis indicated that 43% genomic DNA PCR products have incorporated the stop codon/Hind III compound mutation in HEK293 cells transfected with the humanized NgAgo and the donor single-stranded oligo BCR-ABL ex6 stop-H3 70mer. FIG. 2b discloses SEQ ID NOS 41-43, respectively, in order of appearance.

FIG. 2c shows the sequencing result that shows the targeted base changes in the designated site (indicated by the dotted line). FIG. 2c discloses SEQ ID NO: 44.

FIG. 3a schematically shows the knock-in of mCherry reporter via micro homologous flanking arms to human Histone 2Bc gene by AISE technology as well as the relative positions of PCR primers used in the experiments.

FIG. 3b shows the 5' junctional PCR product at expected size of 611 bp and 3' junctional PCR product with expected size of 240 bp upon the precise insertion of mCherry in Histon 2Bc gene were visualized in electrophoresis.

DETAILED DESCRIPTION

Figure 1A:
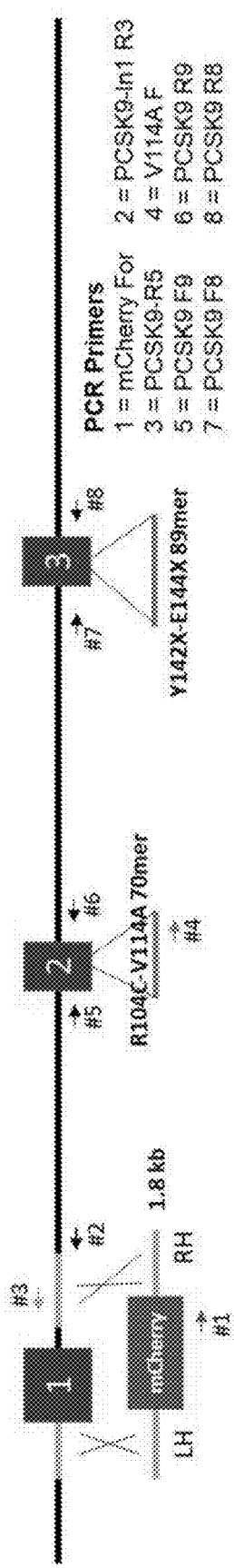
FIG. 1a schematically depicts i) the knock-in of a 1.8 kb fragment of mCherry ORF flanked by homology arms into the exon 1 region of human PCSK9 gene; ii) the introduction of natural loss-of-function R104C-V114A mutation with a single stranded oligonucleotide 70mer donor molecule, for targeting PCSK9 gene by AISE approach; and iii) the introduction of loss-of-function Y142X-E144X mutation with a single-stranded oligonucleotide 89mer donor molecule, for targeting PCSK9 gene by AISE approach.

Presented herein, in some embodiments, is an ANAGO, compositions comprising an ANAGO, kits comprising an ANAGO, and uses thereof, for example, the use of the ANAGO in a homologous recombination directed genome editing in a subject, such as a eukaryote, e.g. a human being. The term "subject" refers to animals, typically mammalian animals, or plants. Any suitable mammal can be treated by a method or composition described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, and pigs) and experimental animal models (e.g., *Drosophila*, zebra fish, *Xenopus*, chick, mouse, rat, rabbit, guinea pig, and pig). In some embodiments a mammal is a human. A mammal can be any age or at any stage of development (e.g., an adult, teen, child, infant, or a mammal in utero). A mammal can be male or female. A mammal can be a pregnant female. In certain embodiments, a mammal can be an animal disease model. In some embodiments, the subject is human. In some embodiments, the subject is an animal. In some embodiments, the subject is a plant.

The term "ANAGO" refers to a codon-Adapted Nuclear Argonaute protein. ANAGO is an Argonaute protein variant derived from a microorganism having DNA endonuclease activities. The DNA coding sequences of a microbial Argonaute protein that has DNA endonuclease activities in microorganisms, such as but not limited to, *natronobacterium gregoryi* [NgAgo], *Pyrococcus furiosus* [PfAgo], *Thermus thermophilus* [TtAgo], *Methanocaldococcus jannaschii* [MjAgo], *Clostridium butyricum* [CbAgo], or *Limnothrix rosea* [LrAgo], etc., can be reengineered and adapted with the codons that are most frequently used (with high usage frequency) or have preferential usage in the cells of a eukaryotic species of interest to generate a new synthetic nucleic acid sequence that encodes an ANAGO, that is species-specific to the eukaryotic species. When expressed in a cell in the eukaryotic species, this ANAGO conserves and/or retains an ability to edit a target nucleic acid sequence within the eukaryotic cell. For example, when the most frequently used codons in human cells are used to replace the microbial preferred codons (referring herein to "reengineering" or "adapting") of a DNA coding sequence of a microbial argonaute protein to generate a new synthetic nucleic acid, which encodes an ANAGO, this type of ANAGO is called human ANAGO. Likewise, when the most frequently used codons or preferentially utilized codons in dog cells are used for reengineering a DNA coding sequence of microbial argonaute protein to generate a new synthetic nucleic acid, which encodes an ANAGO, this type of ANAGO is called dog ANAGO. When the most frequently used codons in plants are used for reengineering a DNA coding sequence of a microbial Argonaute protein to generate a new synthetic nucleic acid, which encodes an ANAGO, this type of ANAGO is called plant ANAGO.

The term "ANAGO" can refer to a protein or to a nucleic acid encoding the protein. For example, when a messenger RNA comprising a synthetic nucleic acid sequence comprises a coding region that encodes an ANAGO in a protein form, the messenger RNA can be called "ANAGO RNA". The DNA comprising the synthetic nucleic acid sequence that transcribes the ANAGO RNA can be called "ANAGO DNA". For example, an ANAGO can be an in vitro transcribed messenger RNA. An ANAGO can be cloned into a mammalian expression vector before being introduced into a eukaryotic cell. For example, a human ANAGO in a form of a protein, or an in vitro transcribed messenger RNA, is cloned into a mammalian expression vector before being introduced into a human cell. The expression vector can be a plasmid, a lentiviral vector, an adeno-associated viral vector, or any viral vector.

The name ANAGO is used both in singular or plural with the all letters always capitalized. For example, we say "an ANAGO", or "two ANAGO", "these ANAGO", "a human ANAGO" or "two human ANAGO", "an ANAGO is used", or "two ANAGO are used", and so on.

The Argonaute protein of a microorganism having DNA endonuclease activities (in short "endonuclease activities") for generating an ANAGO can be from a thermo-bacterium that can tolerate a high temperature of 50-75° C. The ANAGO generated from such a thermo-bacterium can also tolerate a high temperature, such as 50° C., 55° C., >55° C., 50-55° C., 55-60° C., 60-65° C., 65-70° C., 70-75° C., 50-60° C., 60-70° C., 50-70° C., 50-75° C., or any temperature in a range bounded by any of the above values. The Argonaute protein of a microorganism having DNA endonuclease, from which an ANAGO can be derived, can be other microorganisms that are not listed herein.

The ANAGO described herein can be further attached to a Nuclear Localization Signal peptide sequence (NLS) to generate an ANAGO comprising a NLS. This ANAGO comprising a NLS can be further cloned into a eukaryotic expression vector, such as a mammalian expression vector to generate a recombinant ANAGO. This recombinant ANAGO, along with a gene specific donor, with or without a guide oligonucleotide molecule, can be introduced into eukaryotic cells, such as human cells, e.g. HEK293 cells to edit target genomic DNA in a homologous sequence-dependent manner in eukaryotes, such as human. The editing of genome in eukaryotes using species-specific ANAGO can be efficient. The efficiency of the editing of genome in eukaryotic cells, such as human cells, can be at least 1%, at least 5%, 1-60%, 5-60%, 1-70%, 5-70%, 1-80%, 5-80%, 1-90%, 5-90%, 1-100%, 5-100%, more than 1%, more than 5%, 5-10%, 10-15%, 15-20%, 20-25%, 25-30%, 30-35%, 35-40%, 40-45%, 45-50%, 10-20%, 20-30%, 30-40%, 40-50%, 50-60%, 60-70%, 70-80%, 80-90%, 90-100%, 7.1%, 6-8%, 40%, 43%, or any efficiency in a range bounded by any of the above values. The editing of genome in eukaryotic cells, such as human cells, using species-specific ANAGO, such as a human ANAGO can be precise with no significant random insertion and deletion detected. In some embodiments, the homologous recombination directed genome editing in eukaryotic cells, such as human cells, has no off-target events detected.

Either double-stranded or single strand DNA molecules can be used as donor molecules or templates. The homologous donor molecule can have a sequence either short or long. The length of a homology flanking region or arm (5' and/or 3') can be as short as 10 nucleotides. The length of a homology arm or flanking region can be as long as 500 or more nucleotides without upper limit. For example, the length of a homology arm or flanking can be 10-500 nucleotides, 20 nucleotides, 10-20 nucleotides, 20-50 nucleotides, 30-100 nucleotides, 50-100 nucleotides, 100-150 nucleotides, 150-200 nucleotides, 200-300 nucleotides, 300-400 nucleotides, 400-500 nucleotides, 400-600 nucleotides, 500-600 nucleotides, 600-700 nucleotides, 100-300 nucleotides, 300-500 nucleotides, 500-700 nucleotides, 700-1000 nucleotides, 150-250 nucleotides, 250-350 nucleotides, 350-450 nucleotides, 450-550 nucleotides, 550-650 nucleotides, 700-800 nucleotides, 800-900 nucleotides, 900-1000 nucleotides, 800-1000 nucleotides, or any number of nucleotides in a range bounded by any of the above values.

In some embodiments, an altered DNA sequence can be embedded between 5'- and 3'-flanking homologous arms. The length of an altered DNA sequence can be as short as a single nucleotide or as long as 1200 or more nucleotides.

In some embodiments, a single-stranded oligonucleotide (e.g. PCSK9 R104C-V114A 70mer (SEQ ID NO: 5)
5'-CCTGCAGGCCCAGGCTGCC TGCCGGGGATACCTCACCAAGATCCTG

CATG CCTTCCATGGCCTTCTTCCT-3',

FIG. 1a) can be chemically synthesized and used as a donor molecule. The donor molecule harbors 1 or multiple base mismatches (boxed bases) to the targeted genomic sequence at a position at least 15 bases away from both the 5' and 3' ends of oligo.

In some embodiments, a single-stranded oligonucleotide (e.g. BCR-ABLex6 stop-H3 70mer (SEQ ID NO: 6)
5'-GGCAGGGGTCTGCACCCGGGAGCCCCCGTTCT AAGCTTTCACTGA

Figure 2A:
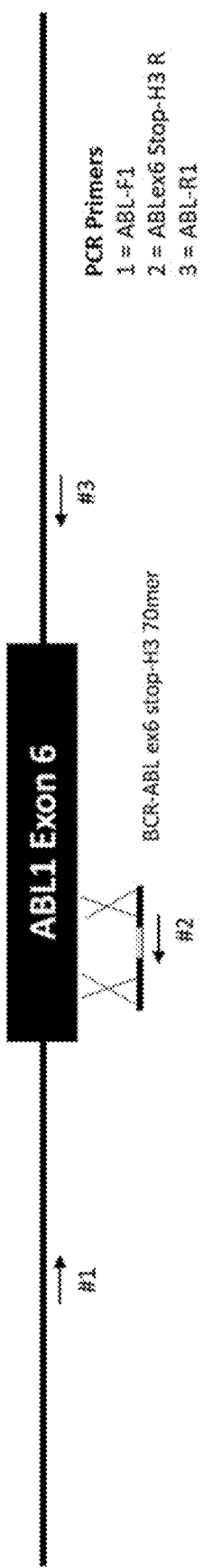
FIG. 2a schematically shows the introduction of a stop codon/HindIII compound mutation into the exon 6 of human ABL1 gene. The region of the engineered 6 specific base changes of BCR-ABL ex6 stop-H3 70mer are marked in light gray color.

GTTCATGACCTACGGGAACCTCCTG-3',

FIG. 2a) can be chemically synthesized and used as a donor molecule. The donor molecule can harbor a restriction enzyme recognition site (boxed sequence) that is inserted into the targeted site and also introduces an in-frame premature stop codon (TAA, bold faced).

In some embodiments, an over 800 bps long donor DNA fragment (e.g. H2Bc-mCherry KI fragment, FIG. 3a) can be synthesized by using a pair of PCR primers that flanks the both ends of a long exogenous gene fragment with a short stretch of sequence (15 to 50 bases or longer) that is homology to the target site in the genome (e.g. the C terminal coding region of human Histon 2Bc gene, FIG. 3a).

In some embodiments, a double-stranded large donor DNA fragment can be generated via fusion PCR (e.g. the 1.8 kb of PCSK9-mCherry knock-in fragment to replace the exon 1 sequence of human PCSK9 gene, see FIG. 1a). The left and right homology arms (over 500 bp long for each one) are generated and fused to an exogenous sequence such as mCherry fragment. The left and right homology regions can be separated by a sequence of 0 to at least 648 bps.

The term "nucleic acid" refers to one or more nucleic acids (e.g., a set or subset of nucleic acids) of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. In some embodiments a nucleic acid refers to DNA. In some embodiments a nucleic acid refers to RNA. Unless specifically limited, the term encompasses nucleic acids comprising deoxyribonucleotides, ribonucleotides and known analogs of natural nucleotides. A nucleic acid may include, as equivalents, derivatives, or variants thereof, suitable analogs of RNA or DNA synthesized from nucleotide analogs, single-stranded ("sense" or "antisense", "plus" strand or "minus" strand, "forward" reading frame or "reverse" reading frame) and double-stranded polynucleotides. Nucleic acids may be single or double stranded. A nucleic acid can be of any length of 2 or more, 3 or more, 4 or more, or 5 or more contiguous nucleotides. A nucleic acid can comprise a specific 5' to 3'order of nucleotides known in the art as a sequence (e.g., a nucleic acid sequence, e.g., a sequence).

A nucleic acid may be naturally occurring and/or may be synthesized, copied or altered (e.g., by a technician, scientist or one of skill in the art). For, example, a nucleic acid may be an amplicon. A nucleic acid may be from a nucleic acid library, such as a gDNA, cDNA or RNA library, for example. A nucleic acid can be synthesized (e.g., chemically synthesized) or generated (e.g., by polymerase extension in vitro, e.g., by amplification, e.g., by PCR). A nucleic acid may be, or may be from, a plasmid, phage, virus, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. Nucleic acid provided for processes or methods described herein may comprise nucleic acids comprising 1 to 1000 or more, 1 to 1000, 1 to 500, 1 to 200, 1 to 100, 1 to 50, 1 to 20, or 1 to 10 nucleotides in length. Oligonucleotides are relatively short nucleic acids. Oligonucleotides can be from about 2 to 200, 2 to 150, 2 to 100, 2 to 50, or 2 to about 35 nucleotides in length. In certain embodiments, oligonucleotides are 18 to 30, 20 to 28 or 21-26 nucleotides in length. In some embodiments, oligonucleotides are single stranded. In certain embodiments, oligonucleotides are primers. Primers are often configured to hybridize to a selected complementary nucleic acid and are configured to be extended by a polymerase after hybridizing.

A genome refers to the genetic material of a cell, a virus, or an organism. The genetic material of a cell or organism often comprises one or more genes. In certain embodiments a gene comprises or consists of one or more nucleic acids. The term "gene" means the segment of DNA involved in producing a polypeptide chain and can include coding regions (e.g., exons), regions preceding and following the coding region (leader and trailer) involved in the transcription/translation of the gene product and the regulation of the transcription/translation, as well as intervening sequences (introns) between individual coding segments (exons). A gene may not necessarily produce a peptide or may produce a truncated or non-functional protein due to genetic variation in a gene sequence (e.g., mutations in coding and non-coding portions of a gene). For example, a non-functional gene can be a pseudogene. A gene may also produce a non-coding RNA, such as long non-coding RNA (lncRNA); microRNA (miRNA); small interfering RNA (siRNA);

Piwi-interacting RNA (piRNAs); or small nucleolar RNA (snoRNA), and other short RNA (Ma L, Bajic V B, and Zhang Z, "On the classification of long non-coding RNAs", RNA Biology. 10 (6): 925-33, June 2013). A gene, whether functional or non-functional, can often be identified by homology to a gene in a reference genome. For example, any specific gene (e.g., a gene of interest, a counterpart gene, a pseudogene and the like) of a subject can be identified in another subject, genome or in a reference genome by one of skill in the art. In a diploid subject, a gene often comprises a pair of alleles (e.g., two alleles). Thus, a method, system or process herein can be applied to one or both alleles of a gene. In some embodiments a method, system or process herein is applied to each allele of a gene.

The term "percent identical" or "percent identity" refers to sequence identity between two amino acid sequences. Identity can be determined by comparing a position in each sequence which may be aligned for purposes of comparison. When an equivalent position in the compared sequences is occupied by the same amino acid, then the molecules are identical at that position. When the equivalent site is occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. In some embodiments an alignment program that permits gaps in the sequence is utilized to align the sequences. The Smith-Waterman is one type of algorithm that permits gaps in sequence alignments. See Meth. Mol. Biol. 70:173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches; and is especially tolerant of small gaps and nucleotide sequence errors. Nucleic acid-encoded amino acid sequences can be used to search both protein and DNA databases.

In some embodiments a nucleic acid described herein comprises a label. As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins can be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

In some embodiments, a carrier, radioisotope and/or a polypeptide can be indirectly or directly associated with, or bound to (e.g., covalently bound to, or conjugated to), a nucleic acid described herein. In certain embodiments agents or molecules are sometimes conjugated to or bound to nucleic acids to alter or extend the in vivo half-life of a nucleic acid or fragment thereof. In some embodiments, a nucleic acid described herein is fused or associated with one or more polypeptides (e.g., a toxin, ligand, receptor, cytokine, antibody, the like or combinations thereof). In certain embodiments, a nucleic acid described herein is linked to a half-life extending vehicle known in the art. Such vehicles include, but are not limited to, polyethylene glycol, glycogen (e.g., glycosylation of the antigen binding protein), and dextran. Such vehicles are described, e.g., in U.S. application Ser. No. 09/428,082, now U.S. Pat. No. 6,660,843 and published PCT Application No. WO 99/25044, hereby incorporated by reference.

In some embodiments carriers or anti-bacterial medications are bound to a nucleic acid described herein by a linker. A linker can provide a mechanism for covalently attaching a carrier and/or anti-bacterial medications to a nucleic acid described herein. Any suitable linker can be used in a composition or method described herein. Non-limiting examples of suitable linkers include silanes, thiols, phosphonic acid, and polyethylene glycol (PEG). Methods of attaching two or more molecules using a linker are well known in the art and are sometimes referred to as "crosslinking". Non-limiting examples of crosslinking include an amine reacting with a N-hydroxysuccinimide (NHS) ester, an imidoester, a pentafluorophenyl (PFP) ester, a hydroxymethyl phosphine, an oxirane or any other carbonyl compound; a carboxyl reacting with a carbodiimide; a sulfhydryl reacting with a maleimide, a haloacetyl, a pyridyldisulfide, and/or a vinyl sulfone; an aldehyde reacting with a hydrazine; any non-selective group reacting with diazirine and/or aryl azide; a hydroxyl reacting with isocyanate; a hydroxylamine reacting with a carbonyl compound; the like and combinations thereof.

In certain embodiments, presented herein is a nucleic acid that encodes and/or expresses an Argonaute protein or Argonaute polypeptide or a functional fragment thereof. An Argonaute protein or Argonaute polypeptide is a DNA-guided endonuclease that can edit nucleic acids within a cell or subject (e.g., within a genome of a subject) in a target specific manner.

In some embodiments, an ANAGO comprises a polypeptide encoded by the sequence of SEQ ID NO:1, SEQ ID NO:2, SEQ ID NO:3, or SEQ ID NO:4. In certain embodiments, an ANAGO comprises an amino acid sequence having 70% to 100% identity, 80% to 100% identity, 90% to 100% identity or 95% to 100% identity, 70-80% identity, 80-90% identity, 90-100% identity, 70-75% identity, 75-80% identity, 80-85% identity, 85-90% identity, 90-95% identity, 95-100% identity, at least 70% identity, at least 75% identity, at least 80% identity, at least 85% identity, at least 90% identity, at least 95% identity, at least 98% identity, at least 99%, or 100% identity to a polypeptide encoded by the sequence of SEQ ID NO:1, SEQ ID NO:2, SEQ ID NO:3, or SEQ ID NO:4, or a portion thereof. In certain embodiments, an ANAGO conserves and/or retains an ability to edit a target nucleic acid sequence (e.g., RNA, DNA, a gene, promoter or the like) within a eukaryotic cell (e.g., a cell of a subject) in a target specific manner. The ability to edit a target sequence within a genome of a subject refers to an ability to insert, remove and/or replace one or more specific nucleotides within a target sequence of a cell (e.g., a human cell).

Argonaute (Ago) proteins are small RNA or DNA guided, site-specific endonucleases, which are present in all three kingdoms of life. The various functions of Argonaute proteins have been studied extensively. Recent studies have suggested that prokaryotic Argonautes are involved in identifying foreign genetic elements in a sequence specific manner and/or in the recruitment of nucleases. Many DNA coding sequences of prokaryotic Argonaute proteins, such as NgAgo, PfAgo, TtAgo, MjAgo, CbAgo, or LrAgo, etc. can be reengineered and adapted to generate an ANAGO that is species-specific in a eukaryote. The microbial preferred codons can be changed to human preferred codons, such as a codon with a frequency of at least 1 per thousand, at least 2 per thousand, at least 3 per thousand, at least 4 per thousand, at least 5 per thousand, at least 6 per thousand, at least 7 per thousand, at least 8 per thousand, at least 9 per thousand, at least 10 per thousand, at least 11 per thousand, at least 12 per thousand, at least 13 per thousand, at least 14 per thousand, at least 15 per thousand, at least 16 per thousand, at least 17 per thousand, at least 18 per thousand, at least 19 per thousand, at least 20 per thousand, at least 21 per thousand, at least 22 per thousand, at least 23 per thousand, at least 24 per thousand, at least 25 per thousand, at least 26 per thousand, at least 27 per thousand, at least 28 per thousand, at least 29 per thousand, at least or 30 per thousand, at least 31 per thousand, at least 32 per thousand, at least 33 per thousand, at least 34 per thousand, at least 35 per thousand, at least 36 per thousand, at least 37 per thousand, at least 38 per thousand, at least 39 per thousand, at least 40 per thousand, to generate a human ANAGO.

Examples of microbial preferred codons are: ACG, CCG, UCG, GUA, CUA, UUA, and GCG etc.; or their corresponding DNA codons.

Examples of human preferred codons include, but are not limited to, UUU, UCU, UAU, UGU, UUC, UCC, UAC, UGC, UUA, UCA, UUG, UCG, UGG, CUU, CCU, CAU, CGU, CUC, CCC, CAC, CGC, CUA, CCA, CAA, CGA, CUG, CCG, CAG, CGG, AUU, ACU, AAU, AGU, AUC, ACC, AAC, AGC, AUA, ACA, AAA, AGA, AUG, ACG, AAG, AGG, GUU, GCU, GAU, GGU, GUC, GCC, GAC, GGC, GUA, GCA, GAA, GGA, GUG, GCG, GAG, GGG, etc. or their corresponding DNA codons.

Any of the microbial preferred codons in the nucleic acid coding sequences of a microbial Argonaute protein can be replaced by any of the human preferred codons during the reengineering process described herein to generate a synthetic nucleic acid that encodes an ANAGO. In some embodiments, at least about 30%, at least about 40%, at least about 50%, at least about 60%, at least about 70%, at least about 80%, at least about 85%, at least about 90%, at least about 95%, about 100%, about 30-50%, about 50-70%; about 70-80%, about 80-90%, about 90-100%, abut 80-85%, about 85-90%, about 90-95%, about 95-100%, or any percentage in a range bonded by these values of the microbial preferred codons in the nucleic acid sequence of the microbial species are replaced by the human codons to generate a synthetic nucleic acid that encodes an ANAGO. In some embodiments, about at least 30, at least 50, at least 70, at least 100, at least 200, at least 300, at least 400, at least 500, at least 600, at least 700, about 30-1000, about 30-50, about 50-70, about 70-90, about 90-100, about 50-60, about 60-70, about 70-80, about 80-90, about 100-300, about 300-500, about 500-700, about 700-900, about 900-1000, about 100-200, about 200-300, about 300-400, about 400-500, about 500-600, about 600-700, about 700-800, about 800-900, about 900-1000, about 1000 or more of bases of the microbial preferred codons in the nucleic acid sequence of the microbial species are replaced by the human codons to generate a synthetic nucleic acid that encodes an ANAGO. In some embodiments, the ANAGO coding sequence shares about 60%, about 70%, about 80%, about 81%, about 85%, about 90%, about 60-90%, about 60-70%, about 70-80%, about 80-85%, about 80-90%, or any percentage in a range bounded by these values of identity with the microbial version of the argonaute coding sequence from which the ANAGO is derived.

In some embodiments, at least 70%, at least 80%, at least 90%, at least 95%, at least 99%, or 100% of the ACG codons in the nucleic acid coding sequence of a microbial Argonaute protein are replaced with a human preferred codon. In some embodiments, at least 70%, at least 80%, at least 90%, at least 95%, at least 99%, or 100% of the ACG codons in the nucleic acid coding sequence of a microbial Argonaute protein codons in the nucleic acid coding sequence of a microbial Argonaute protein are replaced with a UUU codon. In some embodiments, at least 70%, at least 80%, at least 90%, at least 95%, at least 99%, or 100% of the ACG codons in the nucleic acid coding sequence of a microbial Argonaute protein codons in the nucleic acid coding sequence of a microbial Argonaute protein are replaced with a UCU codon. In some embodiments, at least 70%, at least 80%, at least 90%, at least 95%, at least 99%, or 100% of the ACG codons in the nucleic acid coding sequence of a microbial Argonaute protein are replaced with a UAU codon. In some embodiments, at least 70%, at least 80%, at least 90%, at least 95%, at least 99%, or 100% of the ACG codons in the nucleic acid coding sequence of a microbial Argonaute protein are replaced with a UGU codon. In some embodiments, at least 70%, at least 80%, at least 90%, at least 95%, at least 99%, or 100%, of the ACG codons in the nucleic acid coding sequence of a microbial Argonaute protein are replaced with a UUC codon. In some embodiments, at least 70%, at least 80%, at least 90%, at least 95%, at least 99%, or 100%, of the ACG codons in the nucleic acid coding sequence of a microbial Argonaute protein are replaced with a UCC codon. In some embodiments, at least 70%, at least 80%, at least 90%, at least 95%, at least 99%, or 100%, of the ACG codons in the nucleic acid coding sequence of a microbial Argonaute protein are replaced with a UAC codon. In some embodiments, at least 70%, at least 80%, at least 90%, at least 95%, at least 99%, or 100%, of the ACG codons in the nucleic acid coding sequence of a microbial Argonaute protein are replaced with a UGC codon. In some embodiments, at least 70%, at least 80%, at least 90%, at least 95%, at least 99%, or 100%, of the ACG codons in the nucleic acid coding sequence of a microbial Argonaute protein are replaced with a UUA codon. In some embodiments, at least 70%, at least 80%, at least 90%, at least 95%, at least 99%, or 100%, of the ACG codons in the nucleic acid coding sequence of a microbial Argonaute protein are replaced with a UCA codon. In some embodiments, at least 70%, at least 80%, at least 90%, at least 95%, at least 99%, or 100%, of the ACG codons in the nucleic acid coding sequence of a microbial Argonaute protein are replaced with a UUG codon. In some embodiments, at least 70%, at least 80%, at least 90%, at least 95%, at least 99%, or 100%, of the ACG codons in the nucleic acid coding sequence of a microbial Argonaute protein are replaced with a UCG codon. In some embodiments, at least 70%, at least 80%, at least 90%, at least 95%, at least 99%, or 100%, of the ACG codons in the nucleic acid coding sequence of a microbial Argonaute protein are replaced with a UGG codon. In some embodiments, at least 70%, at least 80%, at least 90%, at least 95%, at least 99%, or 100%, of the ACG codons in the nucleic acid coding sequence of a microbial Argonaute protein are replaced with a CUU codon. In some embodiments, at least 70%, at least 80%, at least 90%, at least 95%, at least 99%, or 100%, of the ACG codons in the nucleic acid coding sequence of a microbial Argonaute protein are replaced with a CCU codon. In some embodiments, at least 70%, at least 80%, at least 90%, at least 95%, at least 99%, or 100%, of the ACG codons in the nucleic acid coding sequence of a microbial Argonaute protein are replaced with a CAU codon. In some embodiments, at least 70%, at least 80%, at least 90%, at least 95%, at least 99%, or 100%, of the ACG codons in the nucleic acid coding sequence of a microbial Argonaute protein are replaced with a CGU codon. In some embodiments, at least 70%, at least 80%, at least 90%, at least 95%, at least 99%, or 100%, of the ACG codons in the nucleic acid coding sequence of a microbial Argonaute protein are replaced with a CUC codon. In some embodiments, at least 70%, at least 80%, at least 90%, at least 95%, at least 99%, or 100%, of the ACG codons in the nucleic acid coding sequence of a microbial Argonaute protein are replaced with a CCC codon. In some embodiments, at least 70%, at least 80%, at least 90%, at least 95%, at least 99%, or 100%, of the ACG codons in the nucleic acid coding sequence of a microbial Argonaute protein are replaced with a CAC codon. In some embodiments, at least 70%, at least 80%, at least 90%, at least 95%, at least 99%, or 100%, of the ACG codons in the nucleic acid coding sequence of a microbial Argonaute protein are replaced with a CGC codon. In some embodiments, at least 70%, at least 80%, at least 90%, at least 95%, at least 99%, or 100%, of the ACG codons in the nucleic acid coding sequence of a microbial Argonaute protein are replaced with a CUA codon. In some embodiments, at least 70%, at least 80%, at least 90%, at least 95%, at least 99%, or 100%, of the ACG codons in the nucleic acid coding sequence of a microbial Argonaute protein are replaced with a CCA codon. In some embodiments, at least 70%, at least 80%, at least 90%, at least 95%, at least 99%, or 100%, of the ACG codons in the nucleic acid coding sequence of a microbial Argonaute protein are replaced with a CAA codon. In some embodiments, at least 70%, at least 80%, at least 90%, at least 95%, at least 99%, or 100%, of the ACG codons in the nucleic acid coding sequence of a microbial Argonaute protein are replaced with a CGA codon. In some embodiments, at least 70%, at least 80%, at least 90%, at least 95%, at least 99%, or 100%, of the ACG codons in the nucleic acid coding sequence of a microbial Argonaute protein are replaced with a CUG codon. In some embodiments, at least 70%, at least 80%, at least 90%, at least 95%, at least 99%, or 100%, of the ACG codons in the nucleic acid coding sequence of a microbial Argonaute protein are replaced with a CCG codon. In some embodiments, at least 70%, at least 80%, at least 90%, at least 95%, at least 99%, or 100%, of the ACG codons in the nucleic acid coding sequence of a microbial Argonaute protein are replaced with a CAG codon. In some embodiments, at least 70%, at least 80%, at least 90%, at least 95%, at least 99%, or 100%, of the ACG codons in the nucleic acid coding sequence of a microbial Argonaute protein are replaced with a CGG codon. In some embodiments, at least 70%, at least 80%, at least 90%, at least 95%, at least 99%, or 100%, of the ACG codons in the nucleic acid coding sequence of a microbial Argonaute protein are replaced with an AUU codon. In some embodiments, at least 70%, at least 80%, at least 90%, at least 95%, at least 99%, or 100%, of the ACG codons in the nucleic acid coding sequence of a microbial Argonaute protein are replaced with a ACU codon. In some embodiments, at least 70%, at least 80%, at least 90%, at least 95%, at least 99%, or 100%, of the ACG codons in the nucleic acid coding sequence of a microbial Argonaute protein are replaced with an AAU codon. In some embodiments, at least 70%, at least 80%, at least 90%, at least 95%, at least 99%, or 100%, of the ACG codons in the nucleic acid coding sequence of a microbial Argonaute protein are replaced with a AGU codon. In some embodiments, at least 70%, at least 80%, at least 90%, at least 95%, at least 99%, or 100%, of the ACG codons in the nucleic acid coding sequence of a microbial Argonaute protein are replaced with a AUC codon. In some embodiments, at least 70%, at least 80%, at least 90%, at least 95%, at least 99%, or 100%, of the ACG codons in the nucleic acid coding sequence of a microbial Argonaute protein are replaced with an ACC codon. In some embodiments, at least 70%, at least 80%, at least 90%, at least 95%, at least 99%, or 100%, of the ACG codons in the nucleic acid coding sequence of a microbial Argonaute protein are replaced with a AAC codon. In some embodiments, at least 70%, at least 80%, at least 90%, at least 95%, at least 99%, or 100%, of the ACG codons in the nucleic acid coding sequence of a microbial Argonaute protein are replaced with a AGC codon. In some embodiments, at least 70%, at least 80%, at least 90%, at least 95%, at least 99%, or 100%, of the ACG codons in the nucleic acid coding sequence of a microbial Argonaute protein are replaced with an AUA codon. In some embodiments, at least 70%, at least 80%, at least 90%, at least 95%, at least 99%, or 100%, of the ACG codons in the nucleic acid coding sequence of a microbial Argonaute protein are replaced with an ACA codon. In some embodiments, at least 70%, at least 80%, at least 90%, at least 95%, at least 99%, or 100%, of the ACG codons in the nucleic acid coding sequence of a microbial Argonaute protein are replaced with a AAA codon. In some embodiments, at least 70%, at least 80%, at least 90%, at least 95%, at least 99%, or 100%, of the ACG codons in the nucleic acid coding sequence of a microbial Argonaute protein are replaced with an AGA codon. In some embodiments, at least 70%, at least 80%, at least 90%, at least 95%, at least 99%, or 100%, of the ACG codons in the nucleic acid coding sequence of a microbial Argonaute protein are replaced with an AUG codon. In some embodiments, at least 70%, at least 80%, at least 90%, at least 95%, at least 99%, or 100%, of the ACG codons in the nucleic acid coding sequence of a microbial Argonaute protein are replaced with an ACG codon. In some embodiments, at least 70%, at least 80%, at least 90%, at least 95%, at least 99%, or 100%, of the ACG codons in the nucleic acid coding sequence of a microbial Argonaute protein are replaced with an AAG codon. In some embodiments, at least 70%, at least 80%, at least 90%, at least 95%, at least 99%, or 100%, of the ACG codons in the nucleic acid coding sequence of a microbial Argonaute protein are replaced with an AGG codon. In some embodiments, at least 70%, at least 80%, at least 90%, at least 95%, at least 99%, or 100%, of the ACG codons in the nucleic acid coding sequence of a microbial Argonaute protein are replaced with a GUU codon. In some embodiments, at least 70%, at least 80%, at least 90%, at least 95%, at least 99%, or 100%, of the ACG codons in the nucleic acid coding sequence of a microbial Argonaute protein are replaced with a GCU codon. In some embodiments, at least 70%, at least 80%, at least 90%, at least 95%, at least 99%, or 100%, of the ACG codons in the nucleic acid coding sequence of a microbial Argonaute protein are replaced with a GAU codon. In some embodiments, at least 70%, at least 80%, at least 90%, at least 95%, at least 99%, or 100%, of the ACG codons in the nucleic acid coding sequence of a microbial Argonaute protein are replaced with a GGU codon. In some embodiments, at least 70%, at least 80%, at least 90%, at least 95%, at least 99%, or 100%, of the ACG codons in the nucleic acid coding sequence of a microbial Argonaute protein are replaced with a GUC codon. In some embodiments, at least 70%, at least 80%, at least 90%, at least 95%, at least 99%, or 100%, of the ACG codons in the nucleic acid coding sequence of a microbial Argonaute protein are replaced with a GCC codon. In some embodiments, at least 70%, at least 80%, at least 90%, at least 95%, at least 99%, or 100%, of the ACG codons in the nucleic acid coding sequence of a microbial Argonaute protein are replaced with a GAC codon. In some embodiments, at least 70%, at least 80%, at least 90%, at least 95%, at least 99%, or 100%, of the ACG codons in the nucleic acid coding sequence of a microbial Argonaute protein are replaced with a GGC codon. In some embodiments, at least 70%, at least 80%, at least 90%, at least 95%, at least 99%, or 100%, of the ACG codons in the nucleic acid coding sequence of a microbial Argonaute protein are replaced with a GUA codon. In some embodiments, at least 70%, at least 80%, at least 90%, at least 95%, at least 99%, or 100%, of the ACG codons in the nucleic acid coding sequence of a microbial Argonaute protein are replaced with a GCA codon. In some embodiments, at least 70%, at least 80%, at least 90%, at least 95%, at least 99%, or 100%, of the ACG codons in the nucleic acid coding sequence of a microbial Argonaute protein are replaced with a GAA codon. In some embodiments, at least 70%, at least 80%, at least 90%, at least 95%, at least 99%, or 100%, of the ACG codons in the nucleic acid coding sequence of a microbial Argonaute protein are replaced with a GGA codon. In some embodiments, at least 70%, at least 80%, at least 90%, at least 95%, at least 99%, or 100%, of the ACG codons in the nucleic acid coding sequence of a microbial Argonaute protein are replaced with a GUG codon. In some embodiments, at least 70%, at least 80%, at least 90%, at least 95%, at least 99%, or 100%, of the ACG codons in the nucleic acid coding sequence of a microbial Argonaute protein are replaced with a GCG codon. In some embodiments, at least 70%, at least 80%, at least 90%, at least 95%, at least 99%, or 100%, of the ACG codons in the nucleic acid coding sequence of a microbial Argonaute protein are replaced with a GAG codon. In some embodiments, at least 70%, at least 80%, at least 90%, at least 95%, at least 99%, or 100%, of the ACG codons in the nucleic acid coding sequence of a microbial Argonaute protein are replaced with a GGG codon.

In some embodiments, at least 70%, at least 80%, at least 90%, at least 95%, at least 99%, or 100%, of the CCG codons in the nucleic acid coding sequence of a microbial Argonaute protein are replaced with a human preferred codon. In some embodiments, at least 70%, at least 80%, at least 90%, at least 95%, at least 99%, or 100%, of the CCG codons in the nucleic acid coding sequence of a microbial Argonaute protein are replaced with a UUU codon. In some embodiments, at least 70%, at least 80%, at least 90%, at least 95%, at least 99%, or 100%, of the CCG codons in the nucleic acid coding sequence of a microbial Argonaute protein are replaced with a UCU codon. In some embodiments, at least 70%, at least 80%, at least 90%, at least 95%, at least 99%, or 100%, of the CCG codons in the nucleic acid coding sequence of a microbial Argonaute protein are replaced with a UAU codon. In some embodiments, at least 70%, at least 80%, at least 90%, at least 95%, at least 99%, or 100%, of the CCG codons in the nucleic acid coding sequence of a microbial Argonaute protein are replaced with a UGU codon. In some embodiments, at least 70%, at least 80%, at least 90%, at least 95%, at least 99%, or 100%, of the CCG codons in the nucleic acid coding sequence of a microbial Argonaute protein are replaced with a UUC codon. In some embodiments, at least 70%, at least 80%, at least 90%, at least 95%, at least 99%, or 100%, of the CCG codons in the nucleic acid coding sequence of a microbial Argonaute protein are replaced with a UCC codon. In some embodiments, at least 70%, at least 80%, at least 90%, at least 95%, at least 99%, or 100%, of the CCG codons in the nucleic acid coding sequence of a microbial Argonaute protein are replaced with a UAC codon. In some embodiments, at least 70%, at least 80%, at least 90%, at least 95%, at least 99%, or 100%, of the CCG codons in the nucleic acid coding sequence of a microbial Argonaute protein are replaced with a UGC codon. In some embodiments, at least 70%, at least 80%, at least 90%, at least 95%, at least 99%, or 100%, of the CCG codons in the nucleic acid coding sequence of a microbial Argonaute protein are replaced with a UUA codon. In some embodiments, at least 70%, at least 80%, at least 90%, at least 95%, at least 99%, or 100%, of the CCG codons in the nucleic acid coding sequence of a microbial Argonaute protein are replaced with a UCA codon. In some embodiments, at least 70%, at least 80%, at least 90%, at least 95%, at least 99%, or 100%, of the CCG codons in the nucleic acid coding sequence of a microbial Argonaute protein are replaced with a UUG codon. In some embodiments, at least 70%, at least 80%, at least 90%, at least 95%, at least 99%, or 100%, of the CCG codons in the nucleic acid coding sequence of a microbial Argonaute protein are replaced with a UCG codon. In some embodiments, at least 70%, at least 80%, at least 90%, at least 95%, at least 99%, or 100%, of the CCG codons in the nucleic acid coding sequence of a microbial Argonaute protein are replaced with a UGG codon. In some embodiments, at least 70%, at least 80%, at least 90%, at least 95%, at least 99%, or 100%, of the CCG codons in the nucleic acid coding sequence of a microbial Argonaute protein are replaced with a CUU codon. In some embodiments, at least 70%, at least 80%, at least 90%, at least 95%, at least 99%, or 100%, of the CCG codons in the nucleic acid coding sequence of a microbial Argonaute protein are replaced with a CCU codon. In some embodiments, at least 70%, at least 80%, at least 90%, at least 95%, at least 99%, or 100%, of the CCG codons in the nucleic acid coding sequence of a microbial Argonaute protein are replaced with a CAU codon. In some embodiments, at least 70%, at least 80%, at least 90%, at least 95%, at least 99%, or 100%, of the CCG codons in the nucleic acid coding sequence of a microbial Argonaute protein are replaced with a CGU codon. In some embodiments, at least 70%, at least 80%, at least 90%, at least 95%, at least 99%, or 100%, of the CCG codons in the nucleic acid coding sequence of a microbial Argonaute protein are replaced with a CUC codon. In some embodiments, at least 70%, at least 80%, at least 90%, at least 95%, at least 99%, or 100%, of the CCG codons in the nucleic acid coding sequence of a microbial Argonaute protein are replaced with a CCC codon. In some embodiments, at least 70%, at least 80%, at least 90%, at least 95%, at least 99%, or 100%, of the CCG codons in the nucleic acid coding sequence of a microbial Argonaute protein are replaced with a CAC codon. In some embodiments, at least 70%, at least 80%, at least 90%, at least 95%, at least 99%, or 100%, of the CCG codons in the nucleic acid coding sequence of a microbial Argonaute protein are replaced with a CGC codon. In some embodiments, at least 70%, at least 80%, at least 90%, at least 95%, at least 99%, or 100%, of the CCG codons in the nucleic acid coding sequence of a microbial Argonaute protein are replaced with a CUA codon. In some embodiments, at least 70%, at least 80%, at least 90%, at least 95%, at least 99%, or 100%, of the CCG codons in the nucleic acid coding sequence of a microbial Argonaute protein are replaced with a CCA codon. In some embodiments, at least 70%, at least 80%, at least 90%, at least 95%, at least 99%, or 100%, of the CCG codons in the nucleic acid coding sequence of a microbial Argonaute protein are replaced with a CAA codon. In some embodiments, at least 70%, at least 80%, at least 90%, at least 95%, at least 99%, or 100%, of the CCG codons in the nucleic acid coding sequence of a microbial Argonaute protein are replaced with a CGA codon. In some embodiments, at least 70%, at least 80%, at least 90%, at least 95%, at least 99%, or 100%, of the CCG codons in the nucleic acid coding sequence of a microbial Argonaute protein are replaced with a CUG codon. In some embodiments, at least 70%, at least 80%, at least 90%, at least 95%, at least 99%, or 100%, of the CCG codons in the nucleic acid coding sequence of a microbial Argonaute protein are replaced with a CCG codon. In some embodiments, at least 70%, at least 80%, at least 90%, at least 95%, at least 99%, or 100%, of the CCG codons in the nucleic acid coding sequence of a microbial Argonaute protein are replaced with a CAG codon. In some embodiments, at least 70%, at least 80%, at least 90%, at least 95%, at least 99%, or 100%, of the CCG codons in the nucleic acid coding sequence of a microbial Argonaute protein are replaced with a CGG codon. In some embodiments, at least 70%, at least 80%, at least 90%, at least 95%, at least 99%, or 100%, of the CCG codons in the nucleic acid coding sequence of a microbial Argonaute protein are replaced with an AUU codon. In some embodiments, at least 70%, at least 80%, at least 90%, at least 95%, at least 99%, or 100%, of the CCG codons in the nucleic acid coding sequence of a microbial Argonaute protein are replaced with an ACU codon. In some embodiments, at least 70%, at least 80%, at least 90%, at least 95%, at least 99%, or 100%, of the CCG codons in the nucleic acid coding sequence of a microbial Argonaute protein are replaced with an AAU codon. In some embodiments, at least 70%, at least 80%, at least 90%, at least 95%, at least 99%, or 100%, of the CCG codons in the nucleic acid coding sequence of a microbial Argonaute protein are replaced with an AGU codon. In some embodiments, at least 70%, at least 80%, at least 90%, at least 95%, at least 99%, or 100%, of the CCG codons in the nucleic acid coding sequence of a microbial Argonaute protein are replaced with an AUC codon. In some embodiments, at least 70%, at least 80%, at least 90%, at least 95%, at least 99%, or 100%, of the CCG codons in the nucleic acid coding sequence of a microbial Argonaute protein are replaced with an ACC codon. In some embodiments, at least 70%, at least 80%, at least 90%, at least 95%, at least 99%, or 100%, of the CCG codons in the nucleic acid coding sequence of a microbial Argonaute protein are replaced with an AAC codon. In some embodiments, at least 70%, at least 80%, at least 90%, at least 95%, at least 99%, or 100%, of the CCG codons in the nucleic acid coding sequence of a microbial Argonaute protein are replaced with an AGC codon. In some embodiments, at least 70%, at least 80%, at least 90%, at least 95%, at least 99%, or 100%, of the CCG codons in the nucleic acid coding sequence of a microbial Argonaute protein are replaced with an AUA codon. In some embodiments, at least 70%, at least 80%, at least 90%, at least 95%, at least 99%, or 100%, of the CCG codons in the nucleic acid coding sequence of a microbial Argonaute protein are replaced with an ACA codon. In some embodiments, at least 70%, at least 80%, at least 90%, at least 95%, at least 99%, or 100%, of the CCG codons in the nucleic acid coding sequence of a microbial Argonaute protein are replaced with a AAA codon. In some embodiments, at least 70%, at least 80%, at least 90%, at least 95%, at least 99%, or 100%, of the CCG codons in the nucleic acid coding sequence of a microbial Argonaute protein are replaced with an AGA codon. In some embodiments, at least 70%, at least 80%, at least 90%, at least 95%, at least 99%, or 100%, of the CCG codons in the nucleic acid coding sequence of a microbial Argonaute protein are replaced with an AUG codon. In some embodiments, at least 70%, at least 80%, at least 90%, at least 95%, at least 99%, or 100%, of the CCG codons in the nucleic acid coding sequence of a microbial Argonaute protein are replaced with an ACG codon. In some embodiments, at least 70%, at least 80%, at least 90%, at least 95%, at least 99%, or 100%, of the CCG codons in the nucleic acid coding sequence of a microbial Argonaute protein are replaced with an AAG codon. In some embodiments, at least 70%, at least 80%, at least 90%, at least 95%, at least 99%, or 100%, of the CCG codons in the nucleic acid coding sequence of a microbial Argonaute protein are replaced with an AGG codon. In some embodiments, at least 70%, at least 80%, at least 90%, at least 95%, at least 99%, or 100%, of the CCG codons in the nucleic acid coding sequence of a microbial Argonaute protein are replaced with a GUU codon. In some embodiments, at least 70%, at least 80%, at least 90%, at least 95%, at least 99%, or 100%, of the CCG codons in the nucleic acid coding sequence of a microbial Argonaute protein are replaced with a GCU codon. In some embodiments, at least 70%, at least 80%, at least 90%, at least 95%, at least 99%, or 100%, of the CCG codons in the nucleic acid coding sequence of a microbial Argonaute protein are replaced with a GAU codon. In some embodiments, at least 70%, at least 80%, at least 90%, at least 95%, at least 99%, or 100%, of the CCG codons in the nucleic acid coding sequence of a microbial Argonaute protein are replaced with a GGU codon. In some embodiments, at least 70%, at least 80%, at least 90%, at least 95%, at least 99%, or 100%, of the CCG codons in the nucleic acid coding sequence of a microbial Argonaute protein are replaced with a GUC codon. In some embodiments, at least 70%, at least 80%, at least 90%, at least 95%, at least 99%, or 100%, of the CCG codons in the nucleic acid coding sequence of a microbial Argonaute protein are replaced with a GCC codon. In some embodiments, at least 70%, at least 80%, at least 90%, at least 95%, at least 99%, or 100%, of the CCG codons in the nucleic acid coding sequence of a microbial Argonaute protein are replaced with a GAC codon. In some embodiments, at least 70%, at least 80%, at least 90%, at least 95%, at least 99%, or 100%, of the CCG codons in the nucleic acid coding sequence of a microbial Argonaute protein are replaced with a GGC codon. In some embodiments, at least 70%, at least 80%, at least 90%, at least 95%, at least 99%, or 100%, of the CCG codons in the nucleic acid coding sequence of a microbial Argonaute protein are replaced with a GUA codon. In some embodiments, at least 70%, at least 80%, at least 90%, at least 95%, at least 99%, or 100%, of the CCG codons in the nucleic acid coding sequence of a microbial Argonaute protein are replaced with a GCA codon. In some embodiments, at least 70%, at least 80%, at least 90%, at least 95%, at least 99%, or 100%, of the CCG codons in the nucleic acid coding sequence of a microbial Argonaute protein are replaced with a GAA codon. In some embodiments, at least 70%, at least 80%, at least 90%, at least 95%, at least 99%, or 100%, of the CCG codons in the nucleic acid coding sequence of a microbial Argonaute protein are replaced with a GGA codon. In some embodiments, at least 70%, at least 80%, at least 90%, at least 95%, at least 99%, or 100%, of the CCG codons in the nucleic acid coding sequence of a microbial Argonaute protein are replaced with a GUG codon. In some embodiments, at least 70%, at least 80%, at least 90%, at least 95%, at least 99%, or 100%, of the CCG codons in the nucleic acid coding sequence of a microbial Argonaute protein are replaced with a GCG codon. In some embodiments, at least 70%, at least 80%, at least 90%, at least 95%, at least 99%, or 100%, of the CCG codons in the nucleic acid coding sequence of a microbial Argonaute protein are replaced with a GAG codon. In some embodiments, at least 70%, at least 80%, at least 90%, at least 95%, at least 99%, or 100%, of the CCG codons in the nucleic acid coding sequence of a microbial Argonaute protein are replaced with a GGG codon.

In some embodiments, at least 70%, at least 80%, at least 90%, at least 95%, at least 99%, or 100%, of the TCG codons in the nucleic acid coding sequence of a microbial Argonaute protein are replaced with a human preferred codon. In some embodiments, at least 70%, at least 80%, at least 90%, at least 95%, at least 99%, or 100%, of the TCG codons in the nucleic acid coding sequence of a microbial Argonaute protein are replaced with a UUU codon. In some embodiments, at least 70%, at least 80%, at least 90%, at least 95%, at least 99%, or 100%, of the TCG codons in the nucleic acid coding sequence of a microbial Argonaute protein are replaced with a UCU codon. In some embodiments, at least 70%, at least 80%, at least 90%, at least 95%, at least 99%, or 100%, of the TCG codons in the nucleic acid coding sequence of a microbial Argonaute protein are replaced with a UAU codon. In some embodiments, at least 70%, at least 80%, at least 90%, at least 95%, at least 99%, or 100%, of the TCG codons in the nucleic acid coding sequence of a microbial Argonaute protein are replaced with a UGU codon. In some embodiments, at least 70%, at least 80%, at least 90%, at least 95%, at least 99%, or 100%, of the TCG codons in the nucleic acid coding sequence of a microbial Argonaute protein are replaced with a UUC codon. In some embodiments, at least 70%, at least 80%, at least 90%, at least 95%, at least 99%, or 100%, of the TCG codons in the nucleic acid coding sequence of a microbial Argonaute protein are replaced with a UCC codon. In some embodiments, at least 70%, at least 80%, at least 90%, at least 95%, at least 99%, or 100%, of the TCG codons in the nucleic acid coding sequence of a microbial Argonaute protein are replaced with a UAC codon. In some embodiments, at least 70%, at least 80%, at least 90%, at least 95%, at least 99%, or 100%, of the TCG codons in the nucleic acid coding sequence of a microbial Argonaute protein are replaced with a UGC codon. In some embodiments, at least 70%, at least 80%, at least 90%, at least 95%, at least 99%, or 100%, of the TCG codons in the nucleic acid coding sequence of a microbial Argonaute protein are replaced with a UUA codon. In some embodiments, at least 70%, at least 80%, at least 90%, at least 95%, at least 99%, or 100%, of the TCG codons in the nucleic acid coding sequence of a microbial Argonaute protein are replaced with a UCA codon. In some embodiments, at least 70%, at least 80%, at least 90%, at least 95%, at least 99%, or 100%, of the TCG codons in the nucleic acid coding sequence of a microbial Argonaute protein are replaced with a UUG codon. In some embodiments, at least 70%, at least 80%, at least 90%, at least 95%, at least 99%, or 100%, of the TCG codons in the nucleic acid coding sequence of a microbial Argonaute protein are replaced with a UCG codon. In some embodiments, at least 70%, at least 80%, at least 90%, at least 95%, at least 99%, or 100%, of the TCG codons in the nucleic acid coding sequence of a microbial Argonaute protein are replaced with a UGG codon. In some embodiments, at least 70%, at least 80%, at least 90%, at least 95%, at least 99%, or 100%, of the TCG codons in the nucleic acid coding sequence of a microbial Argonaute protein are replaced with a CUU codon. In some embodiments, at least 70%, at least 80%, at least 90%, at least 95%, at least 99%, or 100%, of the TCG codons in the nucleic acid coding sequence of a microbial Argonaute protein are replaced with a CCU codon. In some embodiments, at least 70%, at least 80%, at least 90%, at least 95%, at least 99%, or 100%, of the TCG codons in the nucleic acid coding sequence of a microbial Argonaute protein are replaced with a CAU codon. In some embodiments, at least 70%, at least 80%, at least 90%, at least 95%, at least 99%, or 100%, of the TCG codons in the nucleic acid coding sequence of a microbial Argonaute protein are replaced with a CGU codon. In some embodiments, at least 70%, at least 80%, at least 90%, at least 95%, at least 99%, or 100%, of the TCG codons in the nucleic acid coding sequence of a microbial Argonaute protein are replaced with a CUC codon. In some embodiments, at least 70%, at least 80%, at least 90%, at least 95%, at least 99%, or 100%, of the TCG codons in the nucleic acid coding sequence of a microbial Argonaute protein are replaced with a CCC codon. In some embodiments, at least 70%, at least 80%, at least 90%, at least 95%, at least 99%, or 100%, of the TCG codons in the nucleic acid coding sequence of a microbial Argonaute protein are replaced with a CAC codon. In some embodiments, at least 70%, at least 80%, at least 90%, at least 95%, at least 99%, or 100%, of the TCG codons in the nucleic acid coding sequence of a microbial Argonaute protein are replaced with a CGC codon. In some embodiments, at least 70%, at least 80%, at least 90%, at least 95%, at least 99%, or 100%, of the TCG codons in the nucleic acid coding sequence of a microbial Argonaute protein are replaced with a CUA codon. In some embodiments, at least 70%, at least 80%, at least 90%, at least 95%, at least 99%, or 100%, of the TCG codons in the nucleic acid coding sequence of a microbial Argonaute protein are replaced with a CCA codon. In some embodiments, at least 70%, at least 80%, at least 90%, at least 95%, at least 99%, or 100%, of the TCG codons in the nucleic acid coding sequence of a microbial Argonaute protein are replaced with a CAA codon. In some embodiments, at least 70%, at least 80%, at least 90%, at least 95%, at least 99%, or 100%, of the TCG codons in the nucleic acid coding sequence of a microbial Argonaute protein are replaced with a CGA codon. In some embodiments, at least 70%, at least 80%, at least 90%, at least 95%, at least 99%, or 100%, of the TCG codons in the nucleic acid coding sequence of a microbial Argonaute protein are replaced with a CUG codon. In some embodiments, at least 70%, at least 80%, at least 90%, at least 95%, at least 99%, or 100%, of the TCG codons in the nucleic acid coding sequence of a microbial Argonaute protein are replaced with a CCG codon. In some embodiments, at least 70%, at least 80%, at least 90%, at least 95%, at least 99%, or 100%, of the TCG codons in the nucleic acid coding sequence of a microbial Argonaute protein are replaced with a CAG codon. In some embodiments, at least 70%, at least 80%, at least 90%, at least 95%, at least 99%, or 100%, of the TCG codons in the nucleic acid coding sequence of a microbial Argonaute protein are replaced with a CGG codon. In some embodiments, at least 70%, at least 80%, at least 90%, at least 95%, at least 99%, or 100%, of the TCG codons in the nucleic acid coding sequence of a microbial Argonaute protein are replaced with an AUU codon. In some embodiments, at least 70%, at least 80%, at least 90%, at least 95%, at least 99%, or 100%, of the TCG codons in the nucleic acid coding sequence of a microbial Argonaute protein are replaced with an ACU codon. In some embodiments, at least 70%, at least 80%, at least 90%, at least 95%, at least 99%, or 100%, of the TCG codons in the nucleic acid coding sequence of a microbial Argonaute protein are replaced with an AAU codon. In some embodiments, at least 70%, at least 80%, at least 90%, at least 95%, at least 99%, or 100%, of the TCG codons in the nucleic acid coding sequence of a microbial Argonaute protein are replaced with an AGU codon. In some embodiments, at least 70%, at least 80%, at least 90%, at least 95%, at least 99%, or 100%, of the TCG codons in the nucleic acid coding sequence of a microbial Argonaute protein are replaced with an AUC codon. In some embodiments, at least 70%, at least 80%, at least 90%, at least 95%, at least 99%, or 100%, of the TCG codons in the nucleic acid coding sequence of a microbial Argonaute protein are replaced with an ACC codon. In some embodiments, at least 70%, at least 80%, at least 90%, at least 95%, at least 99%, or 100%, of the TCG codons in the nucleic acid coding sequence of a microbial Argonaute protein are replaced with an AAC codon. In some embodiments, at least 70%, at least 80%, at least 90%, at least 95%, at least 99%, or 100%, of the TCG codons in the nucleic acid coding sequence of a microbial Argonaute protein are replaced with an AGC codon. In some embodiments, at least 70%, at least 80%, at least 90%, at least 95%, at least 99%, or 100%, of the TCG codons in the nucleic acid coding sequence of a microbial Argonaute protein are replaced with an AUA codon. In some embodiments, at least 70%, at least 80%, at least 90%, at least 95%, at least 99%, or 100%, of the TCG codons in the nucleic acid coding sequence of a microbial Argonaute protein are replaced with an ACA codon. In some embodiments, at least 70%, at least 80%, at least 90%, at least 95%, at least 99%, or 100%, of the TCG codons in the nucleic acid coding sequence of a microbial Argonaute protein are replaced with a AAA codon. In some embodiments, at least 70%, at least 80%, at least 90%, at least 95%, at least 99%, or 100%, of the TCG codons in the nucleic acid coding sequence of a microbial Argonaute protein are replaced with an AGA codon. In some embodiments, at least 70%, at least 80%, at least 90%, at least 95%, at least 99%, or 100%, of the TCG codons in the nucleic acid coding sequence of a microbial Argonaute protein are replaced with an AUG codon. In some embodiments, at least 70%, at least 80%, at least 90%, at least 95%, at least 99%, or 100%, of the TCG codons in the nucleic acid coding sequence of a microbial Argonaute protein are replaced with an ACG codon. In some embodiments, at least 70%, at least 80%, at least 90%, at least 95%, at least 99%, or 100%, of the TCG codons in the nucleic acid coding sequence of a microbial Argonaute protein are replaced with an AAG codon. In some embodiments, at least 70%, at least 80%, at least 90%, at least 95%, at least 99%, or 100%, of the TCG codons in the nucleic acid coding sequence of a microbial Argonaute protein are replaced with an AGG codon. In some embodiments, at least 70%, at least 80%, at least 90%, at least 95%, at least 99%, or 100%, of the TCG codons in the nucleic acid coding sequence of a microbial Argonaute protein are replaced with a GUU codon. In some embodiments, at least 70%, at least 80%, at least 90%, at least 95%, at least 99%, or 100%, of the TCG codons in the nucleic acid coding sequence of a microbial Argonaute protein are replaced with a GCU codon. In some embodiments, at least 70%, at least 80%, at least 90%, at least 95%, at least 99%, or 100%, of the TCG codons in the nucleic acid coding sequence of a microbial Argonaute protein are replaced with a GAU codon. In some embodiments, at least 70%, at least 80%, at least 90%, at least 95%, at least 99%, or 100%, of the TCG codons in the nucleic acid coding sequence of a microbial Argonaute protein are replaced with a GGU codon. In some embodiments, at least 70%, at least 80%, at least 90%, at least 95%, at least 99%, or 100%, of the TCG codons in the nucleic acid coding sequence of a microbial Argonaute protein are replaced with a GUC codon. In some embodiments, at least 70%, at least 80%, at least 90%, at least 95%, at least 99%, or 100%, of the TCG codons in the nucleic acid coding sequence of a microbial Argonaute protein are replaced with a GCC codon. In some embodiments, at least 70%, at least 80%, at least 90%, at least 95%, at least 99%, or 100%, of the TCG codons in the nucleic acid coding sequence of a microbial Argonaute protein are replaced with a GAC codon. In some embodiments, at least 70%, at least 80%, at least 90%, at least 95%, at least 99%, or 100%, of the TCG codons in the nucleic acid coding sequence of a microbial Argonaute protein are replaced with a GGC codon. In some embodiments, at least 70%, at least 80%, at least 90%, at least 95%, at least 99%, or 100%, of the TCG codons in the nucleic acid coding sequence of a microbial Argonaute protein are replaced with a GUA codon. In some embodiments, at least 70%, at least 80%, at least 90%, at least 95%, at least 99%, or 100%, of the TCG codons in the nucleic acid coding sequence of a microbial Argonaute protein are replaced with a GCA codon. In some embodiments, at least 70%, at least 80%, at least 90%, at least 95%, at least 99%, or 100%, of the TCG codons in the nucleic acid coding sequence of a microbial Argonaute protein are replaced with a GAA codon. In some embodiments, at least 70%, at least 80%, at least 90%, at least 95%, at least 99%, or 100%, of the TCG codons in the nucleic acid coding sequence of a microbial Argonaute protein are replaced with a GGA codon. In some embodiments, at least 70%, at least 80%, at least 90%, at least 95%, at least 99%, or 100%, of the TCG codons in the nucleic acid coding sequence of a microbial Argonaute protein are replaced with a GUG codon. In some embodiments, at least 70%, at least 80%, at least 90%, at least 95%, at least 99%, or 100%, of the TCG codons in the nucleic acid coding sequence of a microbial Argonaute protein are replaced with a GCG codon. In some embodiments, at least 70%, at least 80%, at least 90%, at least 95%, at least 99%, or 100%, of the TCG codons in the nucleic acid coding sequence of a microbial Argonaute protein are replaced with a GAG codon. In some embodiments, at least 70%, at least 80%, at least 90%, at least 95%, at least 99%, or 100%, of the TCG codons in the nucleic acid coding sequence of a microbial Argonaute protein are replaced with a GGG codon.

In some embodiments, at least 70%, at least 80%, at least 90%, at least 95%, at least 99%, or 100%, of the GTA codons in the nucleic acid coding sequence of a microbial Argonaute protein are replaced with a human preferred codon. In some embodiments, at least 70%, at least 80%, at least 90%, at least 95%, at least 99%, or 100%, of the GTA codons in the nucleic acid coding sequence of a microbial Argonaute protein are replaced with a UUU codon. In some embodiments, at least 70%, at least 80%, at least 90%, at least 95%, at least 99%, or 100%, of the GTA codons in the nucleic acid coding sequence of a microbial Argonaute protein are replaced with a UCU codon. In some embodiments, at least 70%, at least 80%, at least 90%, at least 95%, at least 99%, or 100%, of the GTA codons in the nucleic acid coding sequence of a microbial Argonaute protein are replaced with a UAU codon. In some embodiments, at least 70%, at least 80%, at least 90%, at least 95%, at least 99%, or 100%, of the GTA codons in the nucleic acid coding sequence of a microbial Argonaute protein are replaced with a UGU codon. In some embodiments, at least 70%, at least 80%, at least 90%, at least 95%, at least 99%, or 100%, of the GTA codons in the nucleic acid coding sequence of a microbial Argonaute protein are replaced with a UUC codon. In some embodiments, at least 70%, at least 80%, at least 90%, at least 95%, at least 99%, or 100%, of the GTA codons in the nucleic acid coding sequence of a microbial Argonaute protein are replaced with a UCC codon. In some embodiments, at least 70%, at least 80%, at least 90%, at least 95%, at least 99%, or 100%, of the GTA codons in the nucleic acid coding sequence of a microbial Argonaute protein are replaced with a UAC codon. In some embodiments, at least 70%, at least 80%, at least 90%, at least 95%, at least 99%, or 100%, of the GTA codons in the nucleic acid coding sequence of a microbial Argonaute protein are replaced with a UGC codon. In some embodiments, at least 70%, at least 80%, at least 90%, at least 95%, at least 99%, or 100%, of the GTA codons in the nucleic acid coding sequence of a microbial Argonaute protein are replaced with a UUA codon. In some embodiments, at least 70%, at least 80%, at least 90%, at least 95%, at least 99%, or 100%, of the GTA codons in the nucleic acid coding sequence of a microbial Argonaute protein are replaced with a UCA codon. In some embodiments, at least 70%, at least 80%, at least 90%, at least 95%, at least 99%, or 100%, of the GTA codons in the nucleic acid coding sequence of a microbial Argonaute protein are replaced with a UUG codon. In some embodiments, at least 70%, at least 80%, at least 90%, at least 95%, at least 99%, or 100%, of the GTA codons in the nucleic acid coding sequence of a microbial Argonaute protein are replaced with a UCG codon. In some embodiments, at least 70%, at least 80%, at least 90%, at least 95%, at least 99%, or 100%, of the GTA codons in the nucleic acid coding sequence of a microbial Argonaute protein are replaced with a UGG codon. In some embodiments, at least 70%, at least 80%, at least 90%, at least 95%, at least 99%, or 100%, of the GTA codons in the nucleic acid coding sequence of a microbial Argonaute protein are replaced with a CUU codon. In some embodiments, at least 70%, at least 80%, at least 90%, at least 95%, at least 99%, or 100%, of the GTA codons in the nucleic acid coding sequence of a microbial Argonaute protein are replaced with a CCU codon. In some embodiments, at least 70%, at least 80%, at least 90%, at least 95%, at least 99%, or 100%, of the GTA codons in the nucleic acid coding sequence of a microbial Argonaute protein are replaced with a CAU codon. In some embodiments, at least 70%, at least 80%, at least 90%, at least 95%, at least 99%, or 100%, of the GTA codons in the nucleic acid coding sequence of a microbial Argonaute protein are replaced with a CGU codon. In some embodiments, at least 70%, at least 80%, at least 90%, at least 95%, at least 99%, or 100%, of the GTA codons in the nucleic acid coding sequence of a microbial Argonaute protein are replaced with a CUC codon. In some embodiments, at least 70%, at least 80%, at least 90%, at least 95%, at least 99%, or 100%, of the GTA codons in the nucleic acid coding sequence of a microbial Argonaute protein are replaced with a CCC codon. In some embodiments, at least 70%, at least 80%, at least 90%, at least 95%, at least 99%, or 100%, of the GTA codons in the nucleic acid coding sequence of a microbial Argonaute protein are replaced with a CAC codon. In some embodiments, at least 70%, at least 80%, at least 90%, at least 95%, at least 99%, or 100%, of the GTA codons in the nucleic acid coding sequence of a microbial Argonaute protein are replaced with a CGC codon. In some embodiments, at least 70%, at least 80%, at least 90%, at least 95%, at least 99%, or 100%, of the GTA codons in the nucleic acid coding sequence of a microbial Argonaute protein are replaced with a CUA codon. In some embodiments, at least 70%, at least 80%, at least 90%, at least 95%, at least 99%, or 100%, of the GTA codons in the nucleic acid coding sequence of a microbial Argonaute protein are replaced with a CCA codon. In some embodiments, at least 70%, at least 80%, at least 90%, at least 95%, at least 99%, or 100%, of the GTA codons in the nucleic acid coding sequence of a microbial Argonaute protein are replaced with a CAA codon. In some embodiments, at least 70%, at least 80%, at least 90%, at least 95%, at least 99%, or 100%, of the GTA codons in the nucleic acid coding sequence of a microbial Argonaute protein are replaced with a CGA codon. In some embodiments, at least 70%, at least 80%, at least 90%, at least 95%, at least 99%, or 100%, of the GTA codons in the nucleic acid coding sequence of a microbial Argonaute protein are replaced with a CUG codon. In some embodiments, at least 70%, at least 80%, at least 90%, at least 95%, at least 99%, or 100%, of the GTA codons in the nucleic acid coding sequence of a microbial Argonaute protein are replaced with a CCG codon. In some embodiments, at least 70%, at least 80%, at least 90%, at least 95%, at least 99%, or 100%, of the GTA codons in the nucleic acid coding sequence of a microbial Argonaute protein are replaced with a CAG codon. In some embodiments, at least 70%, at least 80%, at least 90%, at least 95%, at least 99%, or 100%, of the GTA codons in the nucleic acid coding sequence of a microbial Argonaute protein are replaced with a CGG codon. In some embodiments, at least 70%, at least 80%, at least 90%, at least 95%, at least 99%, or 100%, of the GTA codons in the nucleic acid coding sequence of a microbial Argonaute protein are replaced with an AUU codon. In some embodiments, at least 70%, at least 80%, at least 90%, at least 95%, at least 99%, or 100%, of the GTA codons in the nucleic acid coding sequence of a microbial Argonaute protein are replaced with an ACU codon. In some embodiments, at least 70%, at least 80%, at least 90%, at least 95%, at least 99%, or 100%, of the GTA codons in the nucleic acid coding sequence of a microbial Argonaute protein are replaced with an AAU codon. In some embodiments, at least 70%, at least 80%, at least 90%, at least 95%, at least 99%, or 100%, of the GTA codons in the nucleic acid coding sequence of a microbial Argonaute protein are replaced with an AGU codon. In some embodiments, at least 70%, at least 80%, at least 90%, at least 95%, at least 99%, or 100%, of the GTA codons in the nucleic acid coding sequence of a microbial Argonaute protein are replaced with an AUC codon. In some embodiments, at least 70%, at least 80%, at least 90%, at least 95%, at least 99%, or 100%, of the GTA codons in the nucleic acid coding sequence of a microbial Argonaute protein are replaced with an ACC codon. In some embodiments, at least 70%, at least 80%, at least 90%, at least 95%, at least 99%, or 100%, of the GTA codons in the nucleic acid coding sequence of a microbial Argonaute protein are replaced with an AAC codon. In some embodiments, at least 70%, at least 80%, at least 90%, at least 95%, at least 99%, or 100%, of the GTA codons in the nucleic acid coding sequence of a microbial Argonaute protein are replaced with an AGC codon. In some embodiments, at least 70%, at least 80%, at least 90%, at least 95%, at least 99%, or 100%, of the GTA codons in the nucleic acid coding sequence of a microbial Argonaute protein are replaced with an AUA codon. In some embodiments, at least 70%, at least 80%, at least 90%, at least 95%, at least 99%, or 100%, of the GTA codons in the nucleic acid coding sequence of a microbial Argonaute protein are replaced with an ACA codon. In some embodiments, at least 70%, at least 80%, at least 90%, at least 95%, at least 99%, or 100%, of the GTA codons in the nucleic acid coding sequence of a microbial Argonaute protein are replaced with a AAA codon. In some embodiments, at least 70%, at least 80%, at least 90%, at least 95%, at least 99%, or 100%, of the GTA codons in the nucleic acid coding sequence of a microbial Argonaute protein are replaced with an AGA codon. In some embodiments, at least 70%, at least 80%, at least 90%, at least 95%, at least 99%, or 100%, of the GTA codons in the nucleic acid coding sequence of a microbial Argonaute protein are replaced with an AUG codon. In some embodiments, at least 70%, at least 80%, at least 90%, at least 95%, at least 99%, or 100%, of the GTA codons in the nucleic acid coding sequence of a microbial Argonaute protein are replaced with an ACG codon. In some embodiments, at least 70%, at least 80%, at least 90%, at least 95%, at least 99%, or 100%, of the GTA codons in the nucleic acid coding sequence of a microbial Argonaute protein are replaced with an AAG codon. In some embodiments, at least 70%, at least 80%, at least 90%, at least 95%, at least 99%, or 100%, of the GTA codons in the nucleic acid coding sequence of a microbial Argonaute protein are replaced with an AGG codon. In some embodiments, at least 70%, at least 80%, at least 90%, at least 95%, at least 99%, or 100%, of the GTA codons in the nucleic acid coding sequence of a microbial Argonaute protein are replaced with a GUU codon. In some embodiments, at least 70%, at least 80%, at least 90%, at least 95%, at least 99%, or 100%, of the GTA codons in the nucleic acid coding sequence of a microbial Argonaute protein are replaced with a GCU codon. In some embodiments, at least 70%, at least 80%, at least 90%, at least 95%, at least 99%, or 100%, of the GTA codons in the nucleic acid coding sequence of a microbial Argonaute protein are replaced with a GAU codon. In some embodiments, at least 70%, at least 80%, at least 90%, at least 95%, at least 99%, or 100%, of the GTA codons in the nucleic acid coding sequence of a microbial Argonaute protein are replaced with a GGU codon. In some embodiments, at least 70%, at least 80%, at least 90%, at least 95%, at least 99%, or 100%, of the GTA codons in the nucleic acid coding sequence of a microbial Argonaute protein are replaced with a GUC codon. In some embodiments, at least 70%, at least 80%, at least 90%, at least 95%, at least 99%, or 100%, of the GTA codons in the nucleic acid coding sequence of a microbial Argonaute protein are replaced with a GCC codon. In some embodiments, at least 70%, at least 80%, at least 90%, at least 95%, at least 99%, or 100%, of the GTA codons in the nucleic acid coding sequence of a microbial Argonaute protein are replaced with a GAC codon. In some embodiments, at least 70%, at least 80%, at least 90%, at least 95%, at least 99%, or 100%, of the GTA codons in the nucleic acid coding sequence of a microbial Argonaute protein are replaced with a GGC codon. In some embodiments, at least 70%, at least 80%, at least 90%, at least 95%, at least 99%, or 100%, of the GTA codons in the nucleic acid coding sequence of a microbial Argonaute protein are replaced with a GUA codon. In some embodiments, at least 70%, at least 80%, at least 90%, at least 95%, at least 99%, or 100%, of the GTA codons in the nucleic acid coding sequence of a microbial Argonaute protein are replaced with a GCA codon. In some embodiments, at least 70%, at least 80%, at least 90%, at least 95%, at least 99%, or 100%, of the GTA codons in the nucleic acid coding sequence of a microbial Argonaute protein are replaced with a GAA codon. In some embodiments, at least 70%, at least 80%, at least 90%, at least 95%, at least 99%, or 100%, of the GTA codons in the nucleic acid coding sequence of a microbial Argonaute protein are replaced with a GGA codon. In some embodiments, at least 70%, at least 80%, at least 90%, at least 95%, at least 99%, or 100%, of the GTA codons in the nucleic acid coding sequence of a microbial Argonaute protein are replaced with a GUG codon. In some embodiments, at least 70%, at least 80%, at least 90%, at least 95%, at least 99%, or 100%, of the GTA codons in the nucleic acid coding sequence of a microbial Argonaute protein are replaced with a GCG codon. In some embodiments, at least 70%, at least 80%, at least 90%, at least 95%, at least 99%, or 100%, of the GTA codons in the nucleic acid coding sequence of a microbial Argonaute protein are replaced with a GAG codon. In some embodiments, at least 70%, at least 80%, at least 90%, at least 95%, at least 99%, or 100%, of the GTA codons in the nucleic acid coding sequence of a microbial Argonaute protein are replaced with a GGG codon.

In some embodiments, at least 70%, at least 80%, at least 90%, at least 95%, at least 99%, or 100%, of the CTA codons in the nucleic acid coding sequence of a microbial Argonaute protein are replaced with a human preferred codon. In some embodiments, at least 70%, at least 80%, at least 90%, at least 95%, at least 99%, or 100%, of the CTA codons in the nucleic acid coding sequence of a microbial Argonaute protein are replaced with a UUU codon. In some embodiments, at least 70%, at least 80%, at least 90%, at least 95%, at least 99%, or 100%, of the CTA codons in the nucleic acid coding sequence of a microbial Argonaute protein are replaced with a UCU codon. In some embodiments, at least 70%, at least 80%, at least 90%, at least 95%, at least 99%, or 100%, of the CTA codons in the nucleic acid coding sequence of a microbial Argonaute protein are replaced with a UAU codon. In some embodiments, at least 70%, at least 80%, at least 90%, at least 95%, at least 99%, or 100%, of the CTA codons in the nucleic acid coding sequence of a microbial Argonaute protein are replaced with a UGU codon. In some embodiments, at least 70%, at least 80%, at least 90%, at least 95%, at least 99%, or 100%, of the CTA codons in the nucleic acid coding sequence of a microbial Argonaute protein are replaced with a UUC codon. In some embodiments, at least 70%, at least 80%, at least 90%, at least 95%, at least 99%, or 100%, of the CTA codons in the nucleic acid coding sequence of a microbial Argonaute protein are replaced with a UCC codon. In some embodiments, at least 70%, at least 80%, at least 90%, at least 95%, at least 99%, or 100%, of the CTA codons in the nucleic acid coding sequence of a microbial Argonaute protein are replaced with a UAC codon. In some embodiments, at least 70%, at least 80%, at least 90%, at least 95%, at least 99%, or 100%, of the CTA codons in the nucleic acid coding sequence of a microbial Argonaute protein are replaced with a UGC codon. In some embodiments, at least 70%, at least 80%, at least 90%, at least 95%, at least 99%, or 100%, of the CTA codons in the nucleic acid coding sequence of a microbial Argonaute protein are replaced with a UUA codon. In some embodiments, at least 70%, at least 80%, at least 90%, at least 95%, at least 99%, or 100%, of the CTA codons in the nucleic acid coding sequence of a microbial Argonaute protein are replaced with a UCA codon. In some embodiments, at least 70%, at least 80%, at least 90%, at least 95%, at least 99%, or 100%, of the CTA codons in the nucleic acid coding sequence of a microbial Argonaute protein are replaced with a UUG codon. In some embodiments, at least 70%, at least 80%, at least 90%, at least 95%, at least 99%, or 100%, of the CTA codons in the nucleic acid coding sequence of a microbial Argonaute protein are replaced with a UCG codon. In some embodiments, at least 70%, at least 80%, at least 90%, at least 95%, at least 99%, or 100%, of the CTA codons in the nucleic acid coding sequence of a microbial Argonaute protein are replaced with a UGG codon. In some embodiments, at least 70%, at least 80%, at least 90%, at least 95%, at least 99%, or 100%, of the CTA codons in the nucleic acid coding sequence of a microbial Argonaute protein are replaced with a CUU codon. In some embodiments, at least 70%, at least 80%, at least 90%, at least 95%, at least 99%, or 100%, of the CTA codons in the nucleic acid coding sequence of a microbial Argonaute protein are replaced with a CCU codon. In some embodiments, at least 70%, at least 80%, at least 90%, at least 95%, at least 99%, or 100%, of the CTA codons in the nucleic acid coding sequence of a microbial Argonaute protein are replaced with a CAU codon. In some embodiments, at least 70%, at least 80%, at least 90%, at least 95%, at least 99%, or 100%, of the CTA codons in the nucleic acid coding sequence of a microbial Argonaute protein are replaced with a CGU codon. In some embodiments, at least 70%, at least 80%, at least 90%, at least 95%, at least 99%, or 100%, of the CTA codons in the nucleic acid coding sequence of a microbial Argonaute protein are replaced with a CUC codon. In some embodiments, at least 70%, at least 80%, at least 90%, at least 95%, at least 99%, or 100%, of the CTA codons in the nucleic acid coding sequence of a microbial Argonaute protein are replaced with a CCC codon. In some embodiments, at least 70%, at least 80%, at least 90%, at least 95%, at least 99%, or 100%, of the CTA codons in the nucleic acid coding sequence of a microbial Argonaute protein are replaced with a CAC codon. In some embodiments, at least 70%, at least 80%, at least 90%, at least 95%, at least 99%, or 100%, of the CTA codons in the nucleic acid coding sequence of a microbial Argonaute protein are replaced with a CGC codon. In some embodiments, at least 70%, at least 80%, at least 90%, at least 95%, at least 99%, or 100%, of the CTA codons in the nucleic acid coding sequence of a microbial Argonaute protein are replaced with a CUA codon. In some embodiments, at least 70%, at least 80%, at least 90%, at least 95%, at least 99%, or 100%, of the CTA codons in the nucleic acid coding sequence of a microbial Argonaute protein are replaced with a CCA codon. In some embodiments, at least 70%, at least 80%, at least 90%, at least 95%, at least 99%, or 100%, of the CTA codons in the nucleic acid coding sequence of a microbial Argonaute protein are replaced with a CAA codon. In some embodiments, at least 70%, at least 80%, at least 90%, at least 95%, at least 99%, or 100%, of the CTA codons in the nucleic acid coding sequence of a microbial Argonaute protein are replaced with a CGA codon. In some embodiments, at least 70%, at least 80%, at least 90%, at least 95%, at least 99%, or 100%, of the CTA codons in the nucleic acid coding sequence of a microbial Argonaute protein are replaced with a CUG codon. In some embodiments, at least 70%, at least 80%, at least 90%, at least 95%, at least 99%, or 100%, of the CTA codons in the nucleic acid coding sequence of a microbial Argonaute protein are replaced with a CCG codon. In some embodiments, at least 70%, at least 80%, at least 90%, at least 95%, at least 99%, or 100%, of the CTA codons in the nucleic acid coding sequence of a microbial Argonaute protein are replaced with a CAG codon. In some embodiments, at least 70%, at least 80%, at least 90%, at least 95%, at least 99%, or 100%, of the CTA codons in the nucleic acid coding sequence of a microbial Argonaute protein are replaced with a CGG codon. In some embodiments, at least 70%, at least 80%, at least 90%, at least 95%, at least 99%, or 100%, of the CTA codons in the nucleic acid coding sequence of a microbial Argonaute protein are replaced with an AUU codon. In some embodiments, at least 70%, at least 80%, at least 90%, at least 95%, at least 99%, or 100%, of the CTA codons in the nucleic acid coding sequence of a microbial Argonaute protein are replaced with an ACU codon. In some embodiments, at least 70%, at least 80%, at least 90%, at least 95%, at least 99%, or 100%, of the CTA codons in the nucleic acid coding sequence of a microbial Argonaute protein are replaced with an AAU codon. In some embodiments, at least 70%, at least 80%, at least 90%, at least 95%, at least 99%, or 100%, of the CTA codons in the nucleic acid coding sequence of a microbial Argonaute protein are replaced with an AGU codon. In some embodiments, at least 70%, at least 80%, at least 90%, at least 95%, at least 99%, or 100%, of the CTA codons in the nucleic acid coding sequence of a microbial Argonaute protein are replaced with an AUC codon. In some embodiments, at least 70%, at least 80%, at least 90%, at least 95%, at least 99%, or 100%, of the CTA codons in the nucleic acid coding sequence of a microbial Argonaute protein are replaced with an ACC codon. In some embodiments, at least 70%, at least 80%, at least 90%, at least 95%, at least 99%, or 100%, of the CTA codons in the nucleic acid coding sequence of a microbial Argonaute protein are replaced with an AAC codon. In some embodiments, at least 70%, at least 80%, at least 90%, at least 95%, at least 99%, or 100%, of the CTA codons in the nucleic acid coding sequence of a microbial Argonaute protein are replaced with an AGC codon. In some embodiments, at least 70%, at least 80%, at least 90%, at least 95%, at least 99%, or 100%, of the CTA codons in the nucleic acid coding sequence of a microbial Argonaute protein are replaced with an AUA codon. In some embodiments, at least 70%, at least 80%, at least 90%, at least 95%, at least 99%, or 100%, of the CTA codons in the nucleic acid coding sequence of a microbial Argonaute protein are replaced with an ACA codon. In some embodiments, at least 70%, at least 80%, at least 90%, at least 95%, at least 99%, or 100%, of the CTA codons in the nucleic acid coding sequence of a microbial Argonaute protein are replaced with an AAA codon. In some embodiments, at least 70%, at least 80%, at least 90%, at least 95%, at least 99%, or 100%, of the CTA codons in the nucleic acid coding sequence of a microbial Argonaute protein are replaced with an AGA codon. In some embodiments, at least 70%, at least 80%, at least 90%, at least 95%, at least 99%, or 100%, of the CTA codons in the nucleic acid coding sequence of a microbial Argonaute protein are replaced with an AUG codon. In some embodiments, at least 70%, at least 80%, at least 90%, at least 95%, at least 99%, or 100%, of the CTA codons in the nucleic acid coding sequence of a microbial Argonaute protein are replaced with an ACG codon. In some embodiments, at least 70%, at least 80%, at least 90%, at least 95%, at least 99%, or 100%, of the CTA codons in the nucleic acid coding sequence of a microbial Argonaute protein are replaced with an AAG codon. In some embodiments, at least 70%, at least 80%, at least 90%, at least 95%, at least 99%, or 100%, of the CTA codons in the nucleic acid coding sequence of a microbial Argonaute protein are replaced with an AGG codon. In some embodiments, at least 70%, at least 80%, at least 90%, at least 95%, at least 99%, or 100%, of the CTA codons in the nucleic acid coding sequence of a microbial Argonaute protein are replaced with a GUU codon. In some embodiments, at least 70%, at least 80%, at least 90%, at least 95%, at least 99%, or 100%, of the CTA codons in the nucleic acid coding sequence of a microbial Argonaute protein are replaced with a GCU codon. In some embodiments, at least 70%, at least 80%, at least 90%, at least 95%, at least 99%, or 100%, of the CTA codons in the nucleic acid coding sequence of a microbial Argonaute protein are replaced with a GAU codon. In some embodiments, at least 70%, at least 80%, at least 90%, at least 95%, at least 99%, or 100%, of the CTA codons in the nucleic acid coding sequence of a microbial Argonaute protein are replaced with a GGU codon. In some embodiments, at least 70%, at least 80%, at least 90%, at least 95%, at least 99%, or 100%, of the CTA codons in the nucleic acid coding sequence of a microbial Argonaute protein are replaced with a GUC codon. In some embodiments, at least 70%, at least 80%, at least 90%, at least 95%, at least 99%, or 100%, of the CTA codons in the nucleic acid coding sequence of a microbial Argonaute protein are replaced with a GCC codon. In some embodiments, at least 70%, at least 80%, at least 90%, at least 95%, at least 99%, or 100%, of the CTA codons in the nucleic acid coding sequence of a microbial Argonaute protein are replaced with a GAC codon. In some embodiments, at least 70%, at least 80%, at least 90%, at least 95%, at least 99%, or 100%, of the CTA codons in the nucleic acid coding sequence of a microbial Argonaute protein are replaced with a GGC codon. In some embodiments, at least 70%, at least 80%, at least 90%, at least 95%, at least 99%, or 100%, of the CTA codons in the nucleic acid coding sequence of a microbial Argonaute protein are replaced with a GUA codon. In some embodiments, at least 70%, at least 80%, at least 90%, at least 95%, at least 99%, or 100%, of the CTA codons in the nucleic acid coding sequence of a microbial Argonaute protein are replaced with a GCA codon. In some embodiments, at least 70%, at least 80%, at least 90%, at least 95%, at least 99%, or 100%, of the CTA codons in the nucleic acid coding sequence of a microbial Argonaute protein are replaced with a GAA codon. In some embodiments, at least 70%, at least 80%, at least 90%, at least 95%, at least 99%, or 100%, of the CTA codons in the nucleic acid coding sequence of a microbial Argonaute protein are replaced with a GGA codon. In some embodiments, at least 70%, at least 80%, at least 90%, at least 95%, at least 99%, or 100%, of the CTA codons in the nucleic acid coding sequence of a microbial Argonaute protein are replaced with a GUG codon. In some embodiments, at least 70%, at least 80%, at least 90%, at least 95%, at least 99%, or 100%, of the CTA codons in the nucleic acid coding sequence of a microbial Argonaute protein are replaced with a GCG codon. In some embodiments, at least 70%, at least 80%, at least 90%, at least 95%, at least 99%, or 100%, of the CTA codons in the nucleic acid coding sequence of a microbial Argonaute protein are replaced with a GAG codon. In some embodiments, at least 70%, at least 80%, at least 90%, at least 95%, at least 99%, or 100%, of the CTA codons in the nucleic acid coding sequence of a microbial Argonaute protein are replaced with a GGG codon.

In some embodiments, at least 70%, at least 80%, at least 90%, at least 95%, at least 99%, or 100%, of the TTA codons in the nucleic acid coding sequence of a microbial Argonaute protein are replaced with a human preferred codon. In some embodiments, at least 70%, at least 80%, at least 90%, at least 95%, at least 99%, or 100%, of the TTA codons in the nucleic acid coding sequence of a microbial Argonaute protein are replaced with a UUU codon. In some embodiments, at least 70%, at least 80%, at least 90%, at least 95%, at least 99%, or 100%, of the TTA codons in the nucleic acid coding sequence of a microbial Argonaute protein are replaced with a UCU codon. In some embodiments, at least 70%, at least 80%, at least 90%, at least 95%, at least 99%, or 100%, of the TTA codons in the nucleic acid coding sequence of a microbial Argonaute protein are replaced with a UAU codon. In some embodiments, at least 70%, at least 80%, at least 90%, at least 95%, at least 99%, or 100%, of the TTA codons in the nucleic acid coding sequence of a microbial Argonaute protein are replaced with a UGU codon. In some embodiments, at least 70%, at least 80%, at least 90%, at least 95%, at least 99%, or 100%, of the TTA codons in the nucleic acid coding sequence of a microbial Argonaute protein are replaced with a UUC codon. In some embodiments, at least 70%, at least 80%, at least 90%, at least 95%, at least 99%, or 100%, of the TTA codons in the nucleic acid coding sequence of a microbial Argonaute protein are replaced with a UCC codon. In some embodiments, at least 70%, at least 80%, at least 90%, at least 95%, at least 99%, or 100%, of the TTA codons in the nucleic acid coding sequence of a microbial Argonaute protein are replaced with a UAC codon. In some embodiments, at least 70%, at least 80%, at least 90%, at least 95%, at least 99%, or 100%, of the TTA codons in the nucleic acid coding sequence of a microbial Argonaute protein are replaced with a UGC codon. In some embodiments, at least 70%, at least 80%, at least 90%, at least 95%, at least 99%, or 100%, of the TTA codons in the nucleic acid coding sequence of a microbial Argonaute protein are replaced with a UUA codon. In some embodiments, at least 70%, at least 80%, at least 90%, at least 95%, at least 99%, or 100%, of the TTA codons in the nucleic acid coding sequence of a microbial Argonaute protein are replaced with a UCA codon. In some embodiments, at least 70%, at least 80%, at least 90%, at least 95%, at least 99%, or 100%, of the TTA codons in the nucleic acid coding sequence of a microbial Argonaute protein are replaced with a UUG codon. In some embodiments, at least 70%, at least 80%, at least 90%, at least 95%, at least 99%, or 100%, of the TTA codons in the nucleic acid coding sequence of a microbial Argonaute protein are replaced with a UCG codon. In some embodiments, at least 70%, at least 80%, at least 90%, at least 95%, at least 99%, or 100%, of the TTA codons in the nucleic acid coding sequence of a microbial Argonaute protein are replaced with a UGG codon. In some embodiments, at least 70%, at least 80%, at least 90%, at least 95%, at least 99%, or 100%, of the TTA codons in the nucleic acid coding sequence of a microbial Argonaute protein are replaced with a CUU codon. In some embodiments, at least 70%, at least 80%, at least 90%, at least 95%, at least 99%, or 100%, of the TTA codons in the nucleic acid coding sequence of a microbial Argonaute protein are replaced with a CCU codon. In some embodiments, at least 70%, at least 80%, at least 90%, at least 95%, at least 99%, or 100%, of the TTA codons in the nucleic acid coding sequence of a microbial Argonaute protein are replaced with a CAU codon. In some embodiments, at least 70%, at least 80%, at least 90%, at least 95%, at least 99%, or 100%, of the TTA codons in the nucleic acid coding sequence of a microbial Argonaute protein are replaced with a CGU codon. In some embodiments, at least 70%, at least 80%, at least 90%, at least 95%, at least 99%, or 100%, of the TTA codons in the nucleic acid coding sequence of a microbial Argonaute protein are replaced with a CUC codon. In some embodiments, at least 70%, at least 80%, at least 90%, at least 95%, at least 99%, or 100%, of the TTA codons in the nucleic acid coding sequence of a microbial Argonaute protein are replaced with a CCC codon. In some embodiments, at least 70%, at least 80%, at least 90%, at least 95%, at least 99%, or 100%, of the TTA codons in the nucleic acid coding sequence of a microbial Argonaute protein are replaced with a CAC codon. In some embodiments, at least 70%, at least 80%, at least 90%, at least 95%, at least 99%, or 100%, of the TTA codons in the nucleic acid coding sequence of a microbial Argonaute protein are replaced with a CGC codon. In some embodiments, at least 70%, at least 80%, at least 90%, at least 95%, at least 99%, or 100%, of the TTA codons in the nucleic acid coding sequence of a microbial Argonaute protein are replaced with a CUA codon. In some embodiments, at least 70%, at least 80%, at least 90%, at least 95%, at least 99%, or 100%, of the TTA codons in the nucleic acid coding sequence of a microbial Argonaute protein are replaced with a CCA codon. In some embodiments, at least 70%, at least 80%, at least 90%, at least 95%, at least 99%, or 100%, of the TTA codons in the nucleic acid coding sequence of a microbial Argonaute protein are replaced with a CAA codon. In some embodiments, at least 70%, at least 80%, at least 90%, at least 95%, at least 99%, or 100%, of the TTA codons in the nucleic acid coding sequence of a microbial Argonaute protein are replaced with a CGA codon. In some embodiments, at least 70%, at least 80%, at least 90%, at least 95%, at least 99%, or 100%, of the TTA codons in the nucleic acid coding sequence of a microbial Argonaute protein are replaced with a CUG codon. In some embodiments, at least 70%, at least 80%, at least 90%, at least 95%, at least 99%, or 100%, of the TTA codons in the nucleic acid coding sequence of a microbial Argonaute protein are replaced with a CCG codon. In some embodiments, at least 70%, at least 80%, at least 90%, at least 95%, at least 99%, or 100%, of the TTA codons in the nucleic acid coding sequence of a microbial Argonaute protein are replaced with a CAG codon. In some embodiments, at least 70%, at least 80%, at least 90%, at least 95%, at least 99%, or 100%, of the TTA codons in the nucleic acid coding sequence of a microbial Argonaute protein are replaced with a CGG codon. In some embodiments, at least 70%, at least 80%, at least 90%, at least 95%, at least 99%, or 100%, of the TTA codons in the nucleic acid coding sequence of a microbial Argonaute protein are replaced with an AUU codon. In some embodiments, at least 70%, at least 80%, at least 90%, at least 95%, at least 99%, or 100%, of the TTA codons in the nucleic acid coding sequence of a microbial Argonaute protein are replaced with an ACU codon. In some embodiments, at least 70%, at least 80%, at least 90%, at least 95%, at least 99%, or 100%, of the TTA codons in the nucleic acid coding sequence of a microbial Argonaute protein are replaced with an AAU codon. In some embodiments, at least 70%, at least 80%, at least 90%, at least 95%, at least 99%, or 100%, of the TTA codons in the nucleic acid coding sequence of a microbial Argonaute protein are replaced with an AGU codon. In some embodiments, at least 70%, at least 80%, at least 90%, at least 95%, at least 99%, or 100%, of the TTA codons in the nucleic acid coding sequence of a microbial Argonaute protein are replaced with an AUC codon. In some embodiments, at least 70%, at least 80%, at least 90%, at least 95%, at least 99%, or 100%, of the TTA codons in the nucleic acid coding sequence of a microbial Argonaute protein are replaced with an ACC codon. In some embodiments, at least 70%, at least 80%, at least 90%, at least 95%, at least 99%, or 100%, of the TTA codons in the nucleic acid coding sequence of a microbial Argonaute protein are replaced with an AAC codon. In some embodiments, at least 70%, at least 80%, at least 90%, at least 95%, at least 99%, or 100%, of the TTA codons in the nucleic acid coding sequence of a microbial Argonaute protein are replaced with an AGC codon. In some embodiments, at least 70%, at least 80%, at least 90%, at least 95%, at least 99%, or 100%, of the TTA codons in the nucleic acid coding sequence of a microbial Argonaute protein are replaced with an AUA codon. In some embodiments, at least 70%, at least 80%, at least 90%, at least 95%, at least 99%, or 100%, of the TTA codons in the nucleic acid coding sequence of a microbial Argonaute protein are replaced with an ACA codon. In some embodiments, at least 70%, at least 80%, at least 90%, at least 95%, at least 99%, or 100%, of the TTA codons in the nucleic acid coding sequence of a microbial Argonaute protein are replaced with a AAA codon. In some embodiments, at least 70%, at least 80%, at least 90%, at least 95%, at least 99%, or 100%, of the TTA codons in the nucleic acid coding sequence of a microbial Argonaute protein are replaced with an AGA codon. In some embodiments, at least 70%, at least 80%, at least 90%, at least 95%, at least 99%, or 100%, of the TTA codons in the nucleic acid coding sequence of a microbial Argonaute protein are replaced with an AUG codon. In some embodiments, at least 70%, at least 80%, at least 90%, at least 95%, at least 99%, or 100%, of the TTA codons in the nucleic acid coding sequence of a microbial Argonaute protein are replaced with an ACG codon. In some embodiments, at least 70%, at least 80%, at least 90%, at least 95%, at least 99%, or 100%, of the TTA codons in the nucleic acid coding sequence of a microbial Argonaute protein are replaced with an AAG codon. In some embodiments, at least 70%, at least 80%, at least 90%, at least 95%, at least 99%, or 100%, of the TTA codons in the nucleic acid coding sequence of a microbial Argonaute protein are replaced with an AGG codon. In some embodiments, at least 70%, at least 80%, at least 90%, at least 95%, at least 99%, or 100%, of the TTA codons in the nucleic acid coding sequence of a microbial Argonaute protein are replaced with a GUU codon. In some embodiments, at least 70%, at least 80%, at least 90%, at least 95%, at least 99%, or 100%, of the TTA codons in the nucleic acid coding sequence of a microbial Argonaute protein are replaced with a GCU codon. In some embodiments, at least 70%, at least 80%, at least 90%, at least 95%, at least 99%, or 100%, of the TTA codons in the nucleic acid coding sequence of a microbial Argonaute protein are replaced with a GAU codon. In some embodiments, at least 70%, at least 80%, at least 90%, at least 95%, at least 99%, or 100%, of the TTA codons in the nucleic acid coding sequence of a microbial Argonaute protein are replaced with a GGU codon. In some embodiments, at least 70%, at least 80%, at least 90%, at least 95%, at least 99%, or 100%, of the TTA codons in the nucleic acid coding sequence of a microbial Argonaute protein are replaced with a GUC codon. In some embodiments, at least 70%, at least 80%, at least 90%, at least 95%, at least 99%, or 100%, of the TTA codons in the nucleic acid coding sequence of a microbial Argonaute protein are replaced with a GCC codon. In some embodiments, at least 70%, at least 80%, at least 90%, at least 95%, at least 99%, or 100%, of the TTA codons in the nucleic acid coding sequence of a microbial Argonaute protein are replaced with a GAC codon. In some embodiments, at least 70%, at least 80%, at least 90%, at least 95%, at least 99%, or 100%, of the TTA codons in the nucleic acid coding sequence of a microbial Argonaute protein are replaced with a GGC codon. In some embodiments, at least 70%, at least 80%, at least 90%, at least 95%, at least 99%, or 100%, of the TTA codons in the nucleic acid coding sequence of a microbial Argonaute protein are replaced with a GUA codon. In some embodiments, at least 70%, at least 80%, at least 90%, at least 95%, at least 99%, or 100%, of the TTA codons in the nucleic acid coding sequence of a microbial Argonaute protein are replaced with a GCA codon. In some embodiments, at least 70%, at least 80%, at least 90%, at least 95%, at least 99%, or 100%, of the TTA codons in the nucleic acid coding sequence of a microbial Argonaute protein are replaced with a GAA codon. In some embodiments, at least 70%, at least 80%, at least 90%, at least 95%, at least 99%, or 100%, of the TTA codons in the nucleic acid coding sequence of a microbial Argonaute protein are replaced with a GGA codon. In some embodiments, at least 70%, at least 80%, at least 90%, at least 95%, at least 99%, or 100%, of the TTA codons in the nucleic acid coding sequence of a microbial Argonaute protein are replaced with a GUG codon. In some embodiments, at least 70%, at least 80%, at least 90%, at least 95%, at least 99%, or 100%, of the TTA codons in the nucleic acid coding sequence of a microbial Argonaute protein are replaced with a GCG codon. In some embodiments, at least 70%, at least 80%, at least 90%, at least 95%, at least 99%, or 100%, of the TTA codons in the nucleic acid coding sequence of a microbial Argonaute protein are replaced with a GAG codon. In some embodiments, at least 70%, at least 80%, at least 90%, at least 95%, at least 99%, or 100%, of the TTA codons in the nucleic acid coding sequence of a microbial Argonaute protein are replaced with a GGG codon.

In some embodiments, at least 70%, at least 80%, at least 90%, at least 95%, at least 99%, or 100%, of the GCG codons in the nucleic acid coding sequence of a microbial Argonaute protein are replaced with a human preferred codon. In some embodiments, at least 70%, at least 80%, at least 90%, at least 95%, at least 99%, or 100%, of the GCG codons in the nucleic acid coding sequence of a microbial Argonaute protein are replaced with a UUU codon. In some embodiments, at least 70%, at least 80%, at least 90%, at least 95%, at least 99%, or 100%, of the GCG codons in the nucleic acid coding sequence of a microbial Argonaute protein are replaced with a UCU codon. In some embodiments, at least 70%, at least 80%, at least 90%, at least 95%, at least 99%, or 100%, of the GCG codons in the nucleic acid coding sequence of a microbial Argonaute protein are replaced with a UAU codon. In some embodiments, at least 70%, at least 80%, at least 90%, at least 95%, at least 99%, or 100%, of the GCG codons in the nucleic acid coding sequence of a microbial Argonaute protein are replaced with a UGU codon. In some embodiments, at least 70%, at least 80%, at least 90%, at least 95%, at least 99%, or 100%, of the GCG codons in the nucleic acid coding sequence of a microbial Argonaute protein are replaced with a UUC codon. In some embodiments, at least 70%, at least 80%, at least 90%, at least 95%, at least 99%, or 100%, of the GCG codons in the nucleic acid coding sequence of a microbial Argonaute protein are replaced with a UCC codon. In some embodiments, at least 70%, at least 80%, at least 90%, at least 95%, at least 99%, or 100%, of the GCG codons in the nucleic acid coding sequence of a microbial Argonaute protein are replaced with a UAC codon. In some embodiments, at least 70%, at least 80%, at least 90%, at least 95%, at least 99%, or 100%, of the GCG codons in the nucleic acid coding sequence of a microbial Argonaute protein are replaced with a UGC codon. In some embodiments, at least 70%, at least 80%, at least 90%, at least 95%, at least 99%, or 100%, of the GCG codons in the nucleic acid coding sequence of a microbial Argonaute protein are replaced with a UUA codon. In some embodiments, at least 70%, at least 80%, at least 90%, at least 95%, at least 99%, or 100%, of the GCG codons in the nucleic acid coding sequence of a microbial Argonaute protein are replaced with a UCA codon. In some embodiments, at least 70%, at least 80%, at least 90%, at least 95%, at least 99%, or 100%, of the GCG codons in the nucleic acid coding sequence of a microbial Argonaute protein are replaced with a UUG codon. In some embodiments, at least 70%, at least 80%, at least 90%, at least 95%, at least 99%, or 100%, of the GCG codons in the nucleic acid coding sequence of a microbial Argonaute protein are replaced with a UCG codon. In some embodiments, at least 70%, at least 80%, at least 90%, at least 95%, at least 99%, or 100%, of the GCG codons in the nucleic acid coding sequence of a microbial Argonaute protein are replaced with a UGG codon. In some embodiments, at least 70%, at least 80%, at least 90%, at least 95%, at least 99%, or 100%, of the GCG codons in the nucleic acid coding sequence of a microbial Argonaute protein are replaced with a CUU codon. In some embodiments, at least 70%, at least 80%, at least 90%, at least 95%, at least 99%, or 100%, of the GCG codons in the nucleic acid coding sequence of a microbial Argonaute protein are replaced with a CCU codon. In some embodiments, at least 70%, at least 80%, at least 90%, at least 95%, at least 99%, or 100%, of the GCG codons in the nucleic acid coding sequence of a microbial Argonaute protein are replaced with a CAU codon. In some embodiments, at least 70%, at least 80%, at least 90%, at least 95%, at least 99%, or 100%, of the GCG codons in the nucleic acid coding sequence of a microbial Argonaute protein are replaced with a CGU codon. In some embodiments, at least 70%, at least 80%, at least 90%, at least 95%, at least 99%, or 100%, of the GCG codons in the nucleic acid coding sequence of a microbial Argonaute protein are replaced with a CUC codon. In some embodiments, at least 70%, at least 80%, at least 90%, at least 95%, at least 99%, or 100%, of the GCG codons in the nucleic acid coding sequence of a microbial Argonaute protein are replaced with a CCC codon. In some embodiments, at least 70%, at least 80%, at least 90%, at least 95%, at least 99%, or 100%, of the GCG codons in the nucleic acid coding sequence of a microbial Argonaute protein are replaced with a CAC codon. In some embodiments, at least 70%, at least 80%, at least 90%, at least 95%, at least 99%, or 100%, of the GCG codons in the nucleic acid coding sequence of a microbial Argonaute protein are replaced with a CGC codon. In some embodiments, at least 70%, at least 80%, at least 90%, at least 95%, at least 99%, or 100%, of the GCG codons in the nucleic acid coding sequence of a microbial Argonaute protein are replaced with a CUA codon. In some embodiments, at least 70%, at least 80%, at least 90%, at least 95%, at least 99%, or 100%, of the GCG codons in the nucleic acid coding sequence of a microbial Argonaute protein are replaced with a CCA codon. In some embodiments, at least 70%, at least 80%, at least 90%, at least 95%, at least 99%, or 100%, of the GCG codons in the nucleic acid coding sequence of a microbial Argonaute protein are replaced with a CAA codon. In some embodiments, at least 70%, at least 80%, at least 90%, at least 95%, at least 99%, or 100%, of the GCG codons in the nucleic acid coding sequence of a microbial Argonaute protein are replaced with a CGA codon. In some embodiments, at least 70%, at least 80%, at least 90%, at least 95%, at least 99%, or 100%, of the GCG codons in the nucleic acid coding sequence of a microbial Argonaute protein are replaced with a CUG codon. In some embodiments, at least 70%, at least 80%, at least 90%, at least 95%, at least 99%, or 100%, of the GCG codons in the nucleic acid coding sequence of a microbial Argonaute protein are replaced with a CCG codon. In some embodiments, at least 70%, at least 80%, at least 90%, at least 95%, at least 99%, or 100%, of the GCG codons in the nucleic acid coding sequence of a microbial Argonaute protein are replaced with a CAG codon. In some embodiments, at least 70%, at least 80%, at least 90%, at least 95%, at least 99%, or 100%, of the GCG codons in the nucleic acid coding sequence of a microbial Argonaute protein are replaced with a CGG codon. In some embodiments, at least 70%, at least 80%, at least 90%, at least 95%, at least 99%, or 100%, of the GCG codons in the nucleic acid coding sequence of a microbial Argonaute protein are replaced with an AUU codon. In some embodiments, at least 70%, at least 80%, at least 90%, at least 95%, at least 99%, or 100%, of the GCG codons in the nucleic acid coding sequence of a microbial Argonaute protein are replaced with an ACU codon. In some embodiments, at least 70%, at least 80%, at least 90%, at least 95%, at least 99%, or 100%, of the GCG codons in the nucleic acid coding sequence of a microbial Argonaute protein are replaced with an AAU codon. In some embodiments, at least 70%, at least 80%, at least 90%, at least 95%, at least 99%, or 100%, of the GCG codons in the nucleic acid coding sequence of a microbial Argonaute protein are replaced with an AGU codon. In some embodiments, at least 70%, at least 80%, at least 90%, at least 95%, at least 99%, or 100%, of the GCG codons in the nucleic acid coding sequence of a microbial Argonaute protein are replaced with an AUC codon. In some embodiments, at least 70%, at least 80%, at least 90%, at least 95%, at least 99%, or 100%, of the GCG codons in the nucleic acid coding sequence of a microbial Argonaute protein are replaced with an ACC codon. In some embodiments, at least 70%, at least 80%, at least 90%, at least 95%, at least 99%, or 100%, of the GCG codons in the nucleic acid coding sequence of a microbial Argonaute protein are replaced with an AAC codon. In some embodiments, at least 70%, at least 80%, at least 90%, at least 95%, at least 99%, or 100%, of the GCG codons in the nucleic acid coding sequence of a microbial Argonaute protein are replaced with an AGC codon. In some embodiments, at least 70%, at least 80%, at least 90%, at least 95%, at least 99%, or 100%, of the GCG codons in the nucleic acid coding sequence of a microbial Argonaute protein are replaced with an AUA codon. In some embodiments, at least 70%, at least 80%, at least 90%, at least 95%, at least 99%, or 100%, of the GCG codons in the nucleic acid coding sequence of a microbial Argonaute protein are replaced with an ACA codon. In some embodiments, at least 70%, at least 80%, at least 90%, at least 95%, at least 99%, or 100%, of the GCG codons in the nucleic acid coding sequence of a microbial Argonaute protein are replaced with a AAA codon. In some embodiments, at least 70%, at least 80%, at least 90%, at least 95%, at least 99%, or 100%, of the GCG codons in the nucleic acid coding sequence of a microbial Argonaute protein are replaced with an AGA codon. In some embodiments, at least 70%, at least 80%, at least 90%, at least 95%, at least 99%, or 100%, of the GCG codons in the nucleic acid coding sequence of a microbial Argonaute protein are replaced with an AUG codon. In some embodiments, at least 70%, at least 80%, at least 90%, at least 95%, at least 99%, or 100%, of the GCG codons in the nucleic acid coding sequence of a microbial Argonaute protein are replaced with an ACG codon. In some embodiments, at least 70%, at least 80%, at least 90%, at least 95%, at least 99%, or 100%, of the GCG codons in the nucleic acid coding sequence of a microbial Argonaute protein are replaced with an AAG codon. In some embodiments, at least 70%, at least 80%, at least 90%, at least 95%, at least 99%, or 100%, of the GCG codons in the nucleic acid coding sequence of a microbial Argonaute protein are replaced with an AGG codon. In some embodiments, at least 70%, at least 80%, at least 90%, at least 95%, at least 99%, or 100%, of the GCG codons in the nucleic acid coding sequence of a microbial Argonaute protein are replaced with a GUU codon. In some embodiments, at least 70%, at least 80%, at least 90%, at least 95%, at least 99%, or 100%, of the GCG codons in the nucleic acid coding sequence of a microbial Argonaute protein are replaced with a GCU codon. In some embodiments, at least 70%, at least 80%, at least 90%, at least 95%, at least 99%, or 100%, of the GCG codons in the nucleic acid coding sequence of a microbial Argonaute protein are replaced with a GAU codon. In some embodiments, at least 70%, at least 80%, at least 90%, at least 95%, at least 99%, or 100%, of the GCG codons in the nucleic acid coding sequence of a microbial Argonaute protein are replaced with a GGU codon. In some embodiments, at least 70%, at least 80%, at least 90%, at least 95%, at least 99%, or 100%, of the GCG codons in the nucleic acid coding sequence of a microbial Argonaute protein are replaced with a GUC codon. In some embodiments, at least 70%, at least 80%, at least 90%, at least 95%, at least 99%, or 100%, of the GCG codons in the nucleic acid coding sequence of a microbial Argonaute protein are replaced with a GCC codon. In some embodiments, at least 70%, at least 80%, at least 90%, at least 95%, at least 99%, or 100%, of the GCG codons in the nucleic acid coding sequence of a microbial Argonaute protein are replaced with a GAC codon. In some embodiments, at least 70%, at least 80%, at least 90%, at least 95%, at least 99%, or 100%, of the GCG codons in the nucleic acid coding sequence of a microbial Argonaute protein are replaced with a GGC codon. In some embodiments, at least 70%, at least 80%, at least 90%, at least 95%, at least 99%, or 100%, of the GCG codons in the nucleic acid coding sequence of a microbial Argonaute protein are replaced with a GUA codon. In some embodiments, at least 70%, at least 80%, at least 90%, at least 95%, at least 99%, or 100%, of the GCG codons in the nucleic acid coding sequence of a microbial Argonaute protein are replaced with a GCA codon. In some embodiments, at least 70%, at least 80%, at least 90%, at least 95%, at least 99%, or 100%, of the GCG codons in the nucleic acid coding sequence of a microbial Argonaute protein are replaced with a GAA codon. In some embodiments, at least 70%, at least 80%, at least 90%, at least 95%, at least 99%, or 100%, of the GCG codons in the nucleic acid coding sequence of a microbial Argonaute protein are replaced with a GGA codon. In some embodiments, at least 70%, at least 80%, at least 90%, at least 95%, at least 99%, or 100%, of the GCG codons in the nucleic acid coding sequence of a microbial Argonaute protein are replaced with a GUG codon. In some embodiments, at least 70%, at least 80%, at least 90%, at least 95%, at least 99%, or 100%, of the GCG codons in the nucleic acid coding sequence of a microbial Argonaute protein are replaced with a GCG codon. In some embodiments, at least 70%, at least 80%, at least 90%, at least 95%, at least 99%, or 100%, of the GCG codons in the nucleic acid coding sequence of a microbial Argonaute protein are replaced with a GAG codon. In some embodiments, at least 70%, at least 80%, at least 90%, at least 95%, at least 99%, or 100%, of the GCG codons in the nucleic acid coding sequence of a microbial Argonaute protein are replaced with a GGG codon.

In certain embodiments, a functional fragment of a microbial Argonaute polypeptide comprises a polypeptide sequence comprising at least 30, at least 50, at least 100, at least 200, at least 300, at least 400, at least 500, at least 600, at least 700 or at least 800 amino acids having at least 75%, at least 80%, at least 85%, at least 90%, at least 95%, at least 98%, at least 99%, or 100%, 70% to 100% identity, 80% to 100% identity, 90% to 100% identity or 95% to 100% identity to the sequence of the prokaryotic Argonaute polypeptide.

In certain embodiments, an ANAGO comprises a polypeptide encoded by portion of a nucleotide sequence of SEQ ID NO:1, SEQ ID NO:2, SEQ ID NO:3, or SEQ ID NO:4, wherein the ANAGO, when expressed in a eukaryotic cell, comprises an ability to edit a target nucleic acid sequence within the eukaryotic cell. In certain embodiments, an ANAGO comprises a polypeptide encoded by portion of the nucleotide sequence of SEQ ID NO:2, SEQ ID NO:3 or SEQ ID NO:4, wherein the ANAGO, when expressed in a eukaryotic cell, comprises an ability to edit a target nucleic acid sequence (target site) within the eukaryotic cell.

In some embodiments, a nucleic acid described herein encodes all or a portion of an ANAGO, non-limiting examples of which include a portion that is 1 to 903 amino acids in length, or at least 50, at least 100, at least 200, at least 300, or at least 500 amino acids in length. In some embodiments, an ANAGO derived and reengineered from the DNA coding sequence of all or a portion of an Argonaute protein/polypeptide such as NgAgo, PfAgo, TtAgo, or MjAgo having nuclease activity, conserves or retains the nuclease activity and/or comprises the ability to insert a heterologous nucleic acid sequence into the genome of a living mammalian cell at a specific targeted locus. In some embodiments, a nucleic acid that encodes an ANAGO, is 70-100%, 70-80%, 80-90%, 90-100%, 80-85%, 85-95%, 90-95%, 95-100%, 80% to 100%, at least 70%, at least 80%, at least 81%, at least 82%, at least 85%, at least 90% or at least 95% identical to the nucleic acid having sequence of SEQ ID NO:1, SEQ ID NO:2, SEQ ID NO:3 or SEQ ID NO:4.

In some embodiments, a nucleic acid that encodes all or a portion of an ANAGO has a nucleic acid sequence having 70-100% or 80% to 100% identity to the nucleic acid sequence of SEQ ID NO:1, SEQ ID NO:2, SEQ ID NO:3, or SEQ ID NO:4. In certain embodiments, a nucleic acid is at least 80%, at least 81%, at least 82%, at least 85%, at least 90% or at least 95% identical to the nucleic acid sequence of SEQ ID NO:1, SEQ ID NO:2, SEQ ID NO:3, or SEQ ID NO:4. A nucleic acid described herein is often not a naturally occurring nucleic acid and is often not found in nature. In certain embodiments, a nucleic acid described herein is a synthetic nucleic acid. A synthetic nucleic acid refers to a nucleic acid sequence that is designed by the hand of man and is not found in nature.

In some embodiments, a nucleic acid that encodes all or a portion of an ANAGO is a nucleic acid that comprises or consists of 50 to 2666 contiguous nucleotides (nt) of the nucleic acid sequence of SEQ ID NO:1, SEQ ID NO:2, SEQ ID NO:3, or SEQ ID NO:4. In certain embodiments, a nucleic acid comprises or consists of at least 50, at least 100, at least 500, at least 750, at least 1000, at least 1500, at least 1750 or at least 2000 contiguous nucleotides of the nucleic acid sequence of SEQ ID NO:1, SEQ ID NO:2, SEQ ID NO:3, or SEQ ID NO:4. In some embodiments, a nucleic acid or synthetic nucleic acid described herein consists of, or comprises, the nucleic acid sequence of SEQ ID NO:1, SEQ ID NO:2, SEQ ID NO:3, or SEQ ID NO:4.

In certain embodiments, a nucleic acid or synthetic nucleic acid described herein comprises a nucleic acid sequence that is 100 to 3000 nucleotides in length having 70-100%, or 80% to 100% identity to the nucleic acid sequence of SEQ ID NO:1, SEQ ID NO:2, SEQ ID NO:3, or SEQ ID NO:4. In certain embodiments, a nucleic acid or synthetic nucleic acid described herein comprises a first nucleic acid sequence that is at least 100, at least 500, at least 750, at least 1000, at least 1500, at least 1750 or at least 2000 nucleotides in length, where the first nucleic acid has at least 70%, at least 80%, at least 81%, at least 82%, at least 85%, at least 90% or at least 95% identity to the nucleic acid sequence of SEQ ID NO:1, SEQ ID NO:2, SEQ ID NO:3, or SEQ ID NO:4.

In certain embodiments, a nucleic acid is configured to express a polypeptide in a mammalian cell. A nucleic acid that is configured to express a polypeptide (e.g., an ANAGO) comprises one or more nucleic acid regulatory sequences that direct the expression of a polypeptide in a cell. Accordingly, a nucleic acid that is configured to express a desired polypeptide, such as ANAGO, may include one or more of a coding region that encodes the desired protein, such as ANAGO, one or more suitable promoters operably linked to the coding region, a translation initiation sequence, a start codon, a stop codon, a polyA signal sequence, a leader sequence, a nuclear localization sequence, and the like. In certain embodiments, a nucleic acid comprises a sequence that encodes a nuclear localization signal (NLS) sequence. Any suitable NLS sequence can be used. One non-limiting example of an NLS sequence is SV40 nuclear localization signal (NLS) sequence. In certain embodiments, a nucleic acid is configured to express an ANAGO, or functional fragment thereof.

A target sequence refers to a specific location (a specific nucleic acid sequence) within the genome of an organism or a cell that one intends to modify using a composition or method described herein. In some embodiments, a target sequence is a nucleic acid located within a genome of a cell or an organism. In some embodiments, a target sequence comprises RNA. In certain embodiments, a target sequence comprises DNA. In some embodiments, a target sequence contains 1 or more nucleotides in length. In some embodiments, a target sequence can be as long as a few thousands or even millions base pairs in length, if it is in a linear contiguous DNA sequence in a chromosome. In certain embodiments, a target sequence is 1000 to 10,000, 5000-10,000, 1000 to 5000, 500 to 1000, 700-1000, 500-700, 100 to 900, 100 to 500, 100 to 300, 100 to 200, 50 to 100, 10 to 100, 200-300, 300-400, 400-500, 500-600, 600-700, 700-800, 800-900, 900-1000, 1000-2000, 2000-3000, 3000-4000, 4000-5000, 5000-6000, 6000-7000, 7000-8000, 8000-9000, 9000-10,000, 10-50, 16 to 50, 16 to 30, 16 to 20, 18 to 50, 18 to 30, 18 to 28, 18 to 25, 18 to 26, 18-20, 19-50, 19-30, 19 to 26, 19 to 25, 19-20, 20 to 30, 20 to 25, 20 to 24, 21 to 24, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any number in a range bounded by any of the above values of nucleotides (nt) or base pairs (bp) in length and may be located within a gene, exon, intron or any suitable portion of a genome. Any nucleotide within a target sequence or any portion of a target sequence can be modified by a method described herein. Any number of nucleotides within a target sequence may be deleted, mutated or replaced, for example by a desired sequence (e.g., an insert sequence of a donor sequence). In some embodiments, one or more nucleotides or a desired sequence are inserted into a target sequence by a method described herein. In certain embodiments, a target sequence provides a nucleic acid sequence that is complementary or identical to a guide oligonucleotide, or portion thereof, for example when the guide oligonucleotide is used in an experiment for comparison purpose as described below. In certain embodiments a target sequence provides a nucleic acid sequence that is complementary or identical to a 5' and/or 3' flanking regions of a donor sequence.

Figure 4A:
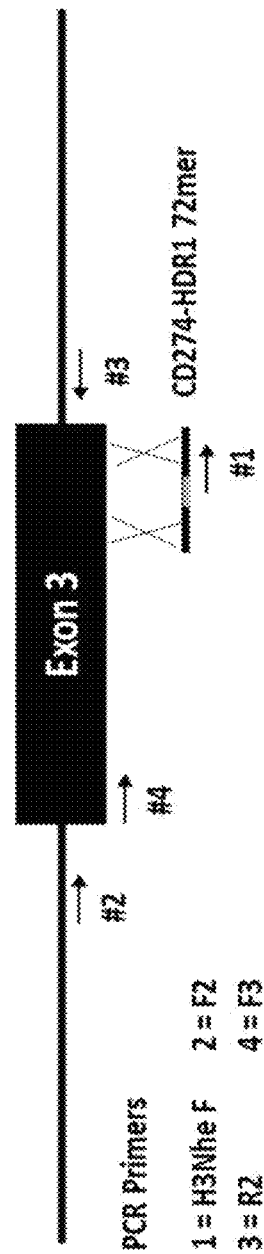
FIG. 4a shows schematically the design of ANAGO directed gene editing with a donor oligo CD274-HDR1 72mer to replace the sequence near the 3' end of exon 3k, for precise gene inactivation.
Figure 4B:
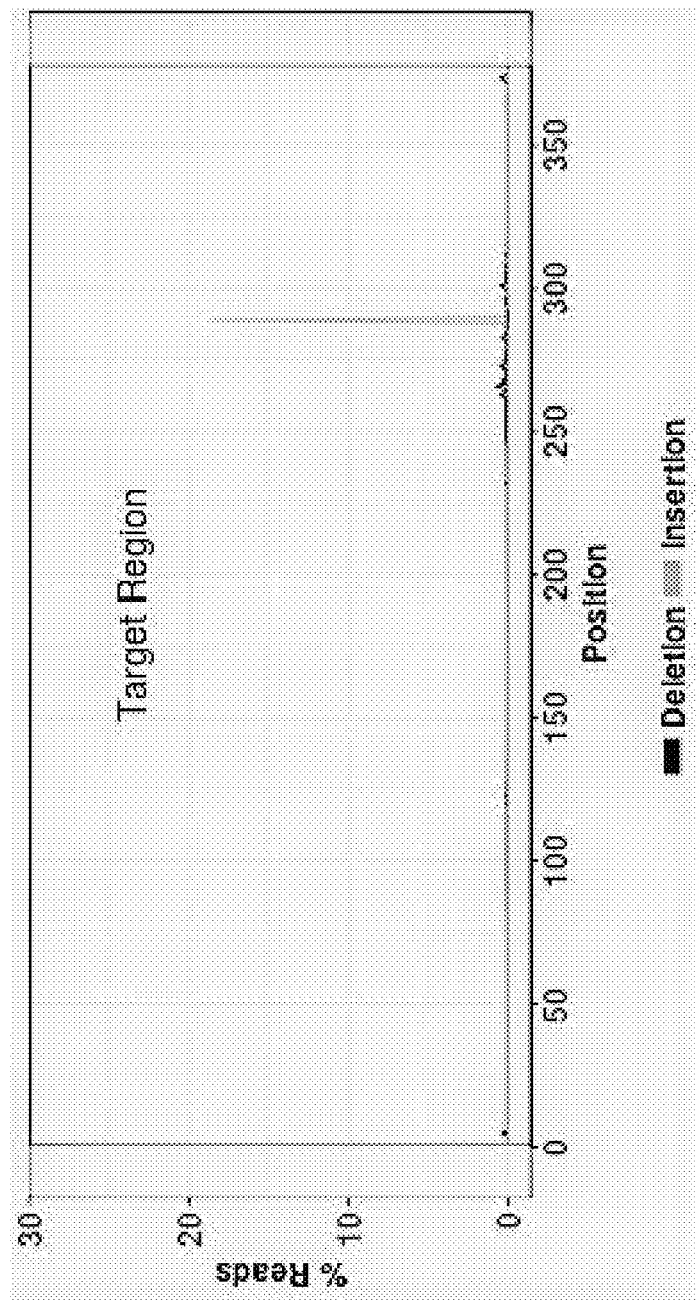
FIG. 4b shows the graphic representation of ultra-deep sequencing result of PCR amplicon products for the target genomic region.

Although a guide oligonucleotide is not needed in the ANAGO induced gene editing technology, a guide molecule was used in some of the experiments described in FIG. 2b and FIG. 4b, solely for comparing the results in the experiment where a guide molecule was not used. A guide oligonucleotide often comprises a nucleic acid sequence that is 80% to 100% identical to the target site. A guide oligonucleotide is sometimes a nucleic acid that is 18 to 30 bases in length. Without being limited to theory, an ANAGO described herein can utilize a guide oligonucleotide to cut the genomic DNA of an organism or cell at a specific target sequence that is defined by the sequence of a guide oligonucleotide. In certain embodiments, an ANAGO cleaves a target nucleic acid sequence anywhere within a sequence defined by a guide oligonucleotide. In some embodiments, an ANAGO cleaves a target site at a location defined by any one of the first 10 nucleotides (5'-nucleotides) of a guide oligonucleotide. When both a guide oligonucleotide and a donor nucleic acid are present, an ANAGO will proceed to replace the targeted sequence with a donor nucleic acid into the genome of a cell at a target site defined by the guide oligonucleotide. If a donor sequence is not present, an ANAGO loaded with a guide oligonucleotide, will often cleave a target site defined by the guide oligonucleotide sequence. This process often results in the introduction of one or more single nucleotide mutations introduced at the target site (e.g., see Example 3).

In some embodiments, there are several advantages to not using a guide molecule in the ANAGO induced precise genomic sequence editing (AISE) technology disclosed herein. First, the percentages of on-target HDR precise editing using the AISE in the presence of a guide molecule and a donor molecule is lower than that of the AISE in the presence of a donor molecule alone without a guide molecule. The difference in the percentages of on-target HDR precise editing between the AISE with a guide molecule and the AISE without a guide molecule can be significant. In some embodiments, the percentages of on-target HDR precise editing using AISE in the presence of a guide molecule and a donor molecule is about 1-10 times, about 1-6 times, about 1-5 times, about 1-4 times, about 1-3 times, about 1 times, about 2 times, about 3 times, about 4 times, about 5 times, about 6 times, about 7 times, about 8 times, about 9 times, about 10 times, about 1%-40%, about 1%-30%, about 1%-20%, about 1%-10%, about 10%-20%, about 20%-30%, about 1%-5%, about 1%-4%, about 1%-3%, about 1%-2%, about 2%-3%, about 3%-4%, about 4%-5%, about 5%-6%, about 6%-7%, about 7%-8%, about 8%-9%, about 9%-10%, about 10%-15%, about 15%-20%, about 20%-25%, about 25%-30%, about 5%-10%, about 1%, about 2%, about 3%, about 3.2%, about 5%, about 10%, about 15%, about 15.3%, or about 20% lower than that of the AISE in the presence of a donor molecule alone without a guide molecule, or any percentage bounded by any of the above values. It is possible that the guide molecule in the AISE described herein may compete with the donor molecule during the sequence editing. Therefore, not only is a guide molecule not required for ANAGO induced precise genomic sequence editing (AISE), but there may also be an advantage in not using a guide molecule in the AISE described herein in achieving precise genomic editing with high yield/percentage.

Furthermore, to prepare a guide molecule that is specific to each given target sequence and to incorporate the guide molecule in AISE requires additional material, synthesis time, purification time, and steps. This may be more time consuming and inconvenient, which would certainly increase overall treatment cost and prolong the overall treatment time when AISE is applied in gene therapy for treating gene related various diseases, disorders, or conditions.

A donor sequence (a donor fragment) is a nucleic acid comprising three parts, a 5' flanking sequence, a desired sequence, and a 3' flanking sequence. In some embodiments, a donor sequence comprises RNA. In certain embodiments, a donor sequence comprises DNA. In some embodiments, a donor sequence is single stranded. In some embodiments, a donor sequence is double stranded. A donor sequence can be short or long in length.

The 5'-flanking sequence and the 3'-flanking sequences are different sequences. In some embodiments, the 5'-flanking sequence and the 3'-flanking sequences do not share more than 10% identity. In some embodiments, the 5'-flanking sequence and the 3'-flanking sequences are located on opposite sides of the desired sequence. Each of 5' flanking sequence and/or each of 3' flanking sequence of a donor sequence, in certain embodiments, is independently about 500 nucleotides (nt) or base pairs (bp) in length, or longer, about 100 nt or bp or longer, 100-200 nt or bp, 10-200 nt or bp, 10-100 nt or bp, 10-75 nt or bp, 75-100 nt or bp, 10-50 nt or bp, 19-50 nt or bp, 19-30 nt or bp, 16-50 nt or bp, 16-30 nt or bp, 10-25 nt or bp, 20-25 nt or bp, 10-20 nt or bp, 20-30 nt or bp, 30-40 nt or bp, 40-50 nt or bp, 50-60 nt or bp, 60-70 nt or bp, 70-80 nt or bp, 80-90 nt or bp, 90-100 nt or bp, 10-15 nt or bp, 15-25 nt or bp, 25-35 nt or bp, 35-45 nt or bp, 45-55 nt or bp, 55-65 nt or bp, 65-75 nt or bp, 75-85 nt or bp, 85-95 nt or bp, 95-100 nt or bp, 16-20 nt or bp, 20-25 nt or bp, 25-30 nt or bp, 30-35 nt or bp, 35-40 nt or bp, 40-45 nt or bp, 45-50 nt or bp, 50-55 nt or bp, 55-60 nt or bp, 60-65 nt or bp, 65-70 nt or bp, 70-75 nt or bp, 75-80 nt or bp, 80-85 nt or bp, 85-90 nt or bp, 90-95 nt or bp, 19-50 nt or bp, 19-30 nt or bp, 16-20 nt or bp, 10 nt or bp, 11 nt or bp, 12 nt or bp, 13 nt or bp, 14 nt or bp, 15 nt or bp, 16 nt or bp, 17 nt or bp, 18 nt or bp, 19 nt or bp, 20 nt or bp, 21 nt or bp, 22 nt or bp, 23 nt or bp, 24 nt or bp, 25 nt or bp, 26 nt or bp, 27 nt or bp, 28 nt or bp, 29 nt or bp, 30 nt or bp, 31 nt or bp, 32 nt or bp, 33 nt or bp, 34 nt or bp, 35 nt or bp, 36 nt or bp, 37 nt or bp, 38 nt or bp, 39 nt or bp, 40 nt or bp, 41 nt or bp, 42 nt or bp, 43 nt or bp, 44 nt or bp, 45 nt or bp, 46 nt or bp, 47 nt or bp, 48 nt or bp, 49 nt or bp, 50 nt or bp, 51 nt or bp, 52 nt or bp, 53 nt or bp, 54 nt or bp, 55 nt or bp, 56 nt or bp, 57 nt or bp, 58 nt or bp, 59 nt or bp, 60 nt or bp, 61 nt or bp, 62 nt or bp, 63 nt or bp, 64 nt or bp, 65 nt or bp, 66 nt or bp, 67 nt or bp, 68 nt or bp, 69 nt or bp, 70 nt or bp, 71 nt or bp, 72 nt or bp, 73 nt or bp, 74 nt or bp, 75 nt or bp, 76 nt or bp, 77 nt or bp, 78 nt or bp, 79 nt or bp, 80 nt or bp, 81 nt or bp, 82 nt or bp, 83 nt or bp, 84 nt or bp, 85 nt or bp, 86 nt or bp, 87 nt or bp, 88 nt or bp, 89 nt or bp, 90 nt or bp, 91 nt or bp, 92 nt or bp, 93 nt or bp, 94 nt or bp, 95 nt or bp, 96 nt or bp, 97 nt or bp, 98 nt or bp, 99 nt or bp, or 100 nt or bp in length, or any number in a range bounded by any of the above values of nucleotides (nt) or base pairs (bp) in length. Each of the 5'-flanking sequence and each of the 3'-flanking sequence independently comprise at least 10 nucleotides that are identical to the target sequence.

A desired sequence refers to a nucleic acid that is to be inserted into a target sequence induced by an ANAGO and/or by a method described herein. The term "desired sequence" is used synonymously with the terms "desired nucleic acid" and "desired nucleic acid sequence". For purposes of clarity, a "desired sequence" may sometimes be referred to as an "insert sequence". In some embodiments, a desired sequence comprises RNA. In certain embodiments, a desired sequence comprises DNA. A desired sequence can be any suitable sequence of any suitable length. In some embodiments, a desired sequence is 1-20,000 nt, 1-10,000 nt, 10,000-20,000 nt, 10,000-15,000 nt, 15,000-20,000 nt, 1-5,000 nt, 1-2500 nt, 2500-5000 nt, 1000-2000 nt, 2000-3000 nt, 3000-4000 nt, 4000-5000 nt, 1-1000 nt, 1-500 nt, 10-5,000 nt, 10-1000 nt, 10-500 nt, 1-100 nt, 100-200 nt, 200-300 nt, 300-400 nt, 400-500 nt, 500-600 nt, 600-700 nt, 700-800 nt, 800-900 nt, 900-1000 nt, 200-400 nt, 400-600 nt, 600-800 nt, 1-50 nt, 50-100 nt, 60-80 nt, 80-100 nt, 18,000 nt, 700 nt, 89 nt, 72 nt, or 70 nucleotides long, or any number in a range bounded by any of the above values of nucleotides in length. In some embodiments, a donor sequence comprises a 5' flanking sequence and a 3' flanking sequence that are each, independently, 80% to 100%, 80%-90%, 90%-100%, 80%-85%, 85%-90%, 90%-95%, 95%-100%, 80%, 81%, 82%, 83%, 84%, 85%, 86%, 87%, 88%, 89%, 90%, 91%, 92%, 93%, 94%, 95%, 96%, 97%, 98%, 99%, or 100% identical to a target site.

Accordingly, in certain embodiments, presented herein is a method of editing a genome of an organism or cell. In certain embodiments, the organism is a subject. In some embodiments, the subject is a human. A cell may be any suitable cell, non-limiting examples of which include a prokaryotic cell, plant cell, eukaryotic cell, mammalian cell or human cell. In certain embodiments, a method of editing a genome comprises removal of a target sequence from a genome, disruption of a target sequence within a genome and/or insertion of a desired sequence into a genome. A desired sequence can be any suitable nucleic acid sequence non-limiting examples of which include a sequence of a heterologous nucleic acid (e.g., from a different species), a modified heterologous nucleic acid, a homologous nucleic acid (e.g., from the same species), a synthetic nucleic acid, a gene or portion thereof (e.g., intron, exon, regulatory sequences, etc.), a modified gene, a marker, a toxin, a single nucleic acid, two or more nucleic acids, the like or a combinations thereof. In some embodiments, a desired nucleic acid encodes a chimeric antigen receptor (CAR).

A desired nucleic acid (desired sequence) or gene can be any suitable mammalian gene, portion thereof, or modified form thereof, non-limiting examples of which include human genes A2M, AACS, AARSD1, ABCA10, ABCA12, ABCA3, ABCA8, ABCA9, ABCB1, ABCB10, ABCB4, ABCC11, ABCC12, ABCC6, ABCD1, ABCE1, ABCF1, ABCF2, ABT1, ACAA2, ACCSL, ACER2, ACO2, ACOT1, ACOT4, ACOT7, ACP1, ACR, ACRC, ACSBG2, ACSM1, ACSM2A, ACSM2B, ACSM4, ACSM5, ACTA1, ACTA2, ACTB, ACTG1, ACTG2, ACTN1, ACTN4, ACTRIA, ACTR2, ACTR3, ACTR3C, ACTRT1, ADAD1, ADAL, ADAM18, ADAM20, ADAM21, ADAM32, ADAMTS7, ADAMTSL2, ADAT2, ADCY5, ADCY6, ADCY7, ADGB, ADH1A, ADH1B, ADH1C, ADH5, ADORA2B, ADRBK2, ADSS, AFF3, AFF4, AFG3L2, AGAP1, AGAP10, AGAP11, AGAP4, AGAP5, AGAP6, AGAP7, AGAP8, AGAP9, AGER, AGGF1, AGK, AGPAT1, AGPAT6, AHCTF1, AHCY, AHNAK2, AHRR, AIDA, AIF1, AIM1L, AIMP2, AK2, AK3, AK4, AKAP13, AKAP17A, AKIP1, AKIRIN, AKIRIN2, AKR1B1, AKR1B10, AKR1B15, AKRC1, AKR1C2, AKR1C3, AKR1C4, AKR7A2, AKR7A3, AKTIP, ALDH3B1, ALDH3B2, ALDH7A1, ALDOA, ALG1, ALG10, ALG10B, ALGL, ALG1L2, ALG3, ALKBH8, ALMS1, ALOX15, ALOX15B, ALOXE3, ALPI, ALPP, ALPPL2, ALYREF, AMD1, AMELX, AMELY, AMMECR1L, AMY1A, AMY1B, AMY1C, AMY2A, AMY2B, AMZ2, ANAPC1, ANAPC10, ANAPC15, ANKRD11, ANKRD18A, ANKRD18B, ANKRD20A1, ANKRD20A19P, ANKRD20A2, ANKRD20A3, ANKRD20A4, ANKRD30A, ANKRD30B, ANKRD36, ANKRD36B, ANKRD49, ANKS1B, ANO10, ANP32A, ANP32B, ANXA2, ANXA2R, ANXA8, ANXA8L1, ANXA8L2, AOC2, AOC3, AP1B1, AP1S2, AP2A1, AP2A2, AP2B1, AP2S1, AP3M2, AP3S1, AP4S1, APBA2, APBB1IP, APH1B, AP15, APIP, APOBEC3A, APOBEC3B, APOBEC3C, APOBEC3D, APOBEC3F, APOBEC3G, APOC1, APOL1, APOL2, APOL4, APOM, APOOL, AQP10, AQP12A, AQP12B, AQP7, AREG, AREGB, ARF1, ARF4, ARF6, ARGFX, ARHGAP11A, ARHGAP11B, ARHGAP20, ARHGAP21, ARHGAP23, ARHGAP27, ARHGAP42, ARHGAP5, ARHGAP8, ARHGEF35, ARHGEF5, ARID2, ARID3B, ARIH2, ARL14EP, ARL16, ARL17A, ARL17B, ARL2BP, ARL4A, ARL5A, ARL61P1, ARL61P6, ARL8B, ARMC1, ARMC10, ARMC4, ARMC8, ARMCX6, ARPC1A, ARPC2, ARPC3, ARPP19, ARSD, ARSE, ARSF, ART3, ASAH2, ASAH2B, ASB9, ASL, ASMT, ASMTL, ASNS, ASS1, ATAD1, ATAD3A, ATAD3B, ATAD3C, ATAT1, ATF4, ATF6B, ATF71P2, ATG4A, ATM, ATMIN, ATP13A4, ATP13A5, ATP1A2, ATP1A4, ATP1B1, ATP1B3, ATP2B2, ATP2B3, ATP5A1, ATP5C1, ATP5F1, ATP5G1, ATP5G2, ATP5G3, ATP5H, ATP5J, ATP5J2, ATP5J2-PTCD1, ATP5O, ATP6AP2, ATP6VOC, ATP6V1E1, ATP6V1F, ATP6V1G1, ATP6V1G2, ATP7B, ATP8A2, ATP9B, ATXN1L, ATXN2L, ATXN7L3, AURKA, AURKAIP1, AVP, AZGP1, AZI2, B3GALNT1, B3GALT4, B3GAT3, B3GNT2, BAG4, BAG6, BAGE2, BAK1, BANF1, BANP, BCAP31, BCAR1, BCAS2, BCL2A1, BCL2L12, BCL2L2-PABPN1, BCLAF1, BCOR, BCR, BDH2, BDP1, BEND3, BET1, BEX1, BHLHB9, BHLHE22, BHLHE23, BHMT, BHMT2, BIN2, BIRC2, BIRC3, BLOC1S6, BLZF1, BMP2K, BMP8A, BMP8B, BMPR1A, BMS1, BNIP3, BOD1, BOD1L2, BOLA2, BOLA2B, BOLA3, BOP1, BPTF, BPY2, BPY2B, BPY2C, BRAF, BRCA1, BRCC3, BRD2, BRD7, BRDT, BRI3, BRK1, BRPF1, BRPF3, BRWD1, BTBD10, BTBD6, BTBD7, BTF3, BTF3L4, BTG1, BTN2A1, BTN2A2, BTN3A1, BTN3A2, BTN3A3, BTNL2, BTNL3, BTNL8, BUB3, BZW1, C10orf129, C10orf88, C11orf48, C11orf58, C11orf74, C11orf75, C12orf29, C12orf42, C12orf49, C12orf71, C12orf76, C14orf119, C14orf166, C14orf178, C15orf39, C15orf40, C15orf43, C16orf52, C16orf88, C17orf51, C17orf58, C17orf61, C17orf89, C17orf98, C18orf21, C18orf25, C1D, C1GALT1, C1QBP, C1QL1, C1QL4, C1QTNF9, C1QTNF9B, C1QTNF9B-AS1, C1orf100, C1orf106, C1orf114, C2, C22orf42, C22orf43, C2CD4A, C2orf16, C2orf27A, C2orf27B, C2orf69, C2orf78, C2orf81, C4A, C4B, C4BPA, C4orf27, C4orf34, C4orf46, C5orf15, C5orf43, C5orf52, C5orf60, C5orf63, C6orf10, C6orf106, C6orf136, C6orf15, C6orf203, C6orf25, C6orf47, C6orf48, C7orf63, C7orf73, C8orf46, C9orf123, C9orf129, C9orf172, C9orf57, C9orf69, C9orf78, CA14, CA15P3, CA5A, CA5B, CABYR, CACNA1C, CACNA1G, CACNA1H, CACNA1I, CACYBP, CALCA, CALCB, CALM1, CALM2, CAMSAP1, CAP1, CAPN8, CAPZA1, CAPZA2, CARD16, CARD17, CASC4, CASP1, CASP3, CASP4, CASP5, CATSPER2, CBR1, CBR3, CBWD1, CBWD2, CBWD3, CBWD5, CBWD6, CBWD7, CBX1, CBX3, CCDC101, CCDC111, CCDC121, CCDC127, CCDC14, CCDC144A, CCDC144NL, CCDC146, CCDC150, CCDC174, CCDC25, CCDC58, CCDC7, CCDC74A, CCDC74B, CCDC75, CCDC86, CCHCR1, CCL15, CCL23, CCL3, CCL3L1, CCL3L3, CCL4, CCL4L1, CCL4L2, CCNB1IP1, CCNB2, CCND2, CCNG1, CCNJ, CCNT2, CCNYL1, CCR2, CCR5, CCRL1, CCRN4L, CCT4, CCT5, CCT6A, CCT7, CCT8, CCT8L2, CCZ1, CCZ1B, CD177, CD1A, CD1B, CD1C, CD1D, CD1E, CD200R1, CD200R1L, CD209, CD276, CD2BP2, CD300A, CD300C, CD300LD, CD300LF, CD33, CD46, CD83, CD8B, CD97, CD99, CDC14B, CDC20, CDC26, CDC27, CDC37, CDC42, CDC42EP3, CDCA4, CDCA7L, CDH12, CDK11A, CDK11B, CDK2AP2, CDK5RAP3, CDK7, CDK8, CDKN2A, CDKN2AIPNL, CDKN2B, CDON, CDPF1, CDRT1, CDRT15, CDRT15L2, CDSN, CDV3, CDY1, CDY2A, CDY2B, CEACAM1, CEACAM18, CEACAM21, CEACAM3, CEACAM4, CEACAM5, CEACAM6, CEACAM7, CEACAM8, CEL, CELA2A, CELA2B, CELA3A, CELA3B, CELSR1, CEND1, CENPC1, CENPI, CENPJ, CENPO, CEP170, CEP19, CEP192, CEP290, CEP57L1, CES1, CES2, CES5A, CFB, CFC1, CFC1B, CFH, CFHR1, CFHR2, CFHR3, CFHR4, CFHR5, CFL1, CFTR, CGB, CGB1, CGB2, CGB5, CGB7, CGB8, CHAF1B, CHCHD10, CHCHD2, CHCHD3, CHCHD4, CHD2, CHEK2, CHIA, CHMP4B, CHMP5, CHORDC1, CHP1, CHRAC1, CHRFAM7A, CHRNA2, CHRNA4, CHRNB2, CHRNB4, CHRNE, CHST5, CHST6, CHSY1, CHTF8, CIAPIN1, CIC, CIDEC, CIR1, CISD1, CISD2, CKAP2, CKMT1A, CKMT1B, CKS2, CLC, CLCN3, CLCNKA, CLCNKB, CLDN22, CLDN24, CLDN3, CLDN4, CLDN6, CLDN7, CLEC17A, CLEC18A, CLEC18B, CLEC18C, CLEC1A, CLEC1B, CLEC4G, CLEC4M, CLIC1, CLIC4, CLK2, CLK3, CLK4, CLNS1A, CMPK1, CMYA5, CNEP1R1, CNN2, CNN3, CNNM3, CNNM4, CNOT6L, CNOT7, CNTNAP3, CNTNAP3B, CNTNAP4, COA5, COBL, COIL, COL11A2, COL12A1, COL19A1, COL25A1, COL28A1, COL4A5, COL6A5, COL6A6, COMMD4, COMMD5, COPRS, COPS5, COPS8, COQ10B, CORO1A, COX10, COX17, COX20, COX5A, COX6A1, COX6B1, COX7B, COX7C, COX8C, CP, CPAMD8, CPD, CPEB1, CPSF6, CR1, CR1L, CRADD, CRB3, CRCP, CREBBP, CRHR1, CRLF2, CRLF3, CRNN, CROCC, CRTC1, CRYBB2, CRYGB, CRYGC, CRYGD, CS, CSAG1, CSAG2, CSAG3, CSDA, CSDE1, CSF2RA, CSF2RB, CSGALNACT2, CSH1, CSH2, CSHL1, CSNK1A1, CSNK1D, CSNK1E, CSNK1G2, CSNK2A1, CSNK2B, CSPG4, CSRP2, CST1, CST2, CST3, CST4, CST5, CST9, CT45A1, CT45A2, CT45A3, CT45A4, CT45A5, CT45A6, CT47A1, CT47A10, CT47A11, CT47A12, CT47A2, CT47A3, CT47A4, CT47A5, CT47A6, CT47A7, CT47A8, CT47A9, CT47B1, CTAG1A, CTAG1B, CTAG2, CTAGE1, CTAGE5, CTAGE6P, CTAGE9, CTBP2, CTDNEP1, CTDSP2, CTDSPL2, CTLA4, CTNNA1, CTNND1, CTRB1, CTRB2, CTSL1, CTU1, CUBN, CUL1, CUL7, CUL9, CUTA, CUX1, CXADR, CXCL1, CXCL17, CXCL2, CXCL3, CXCL5, CXCL6, CXCR1, CXCR2, CXorf40A, CXorf40B, CXorf48, CXorf49, CXorf49B, CXorf56, CXorf61, CYB5A, CYCS, CYP11B1, CYP11B2, CYP1A1, CYP1A2, CYP21A2, CYP2A13, CYP2A6, CYP2A7, CYP2B6, CYP2C18, CYP2C19, CYP2C8, CYP2C9, CYP2D6, CYP2F1, CYP3A4, CYP3A43, CYP3A5, CYP3A7, CYP3A7-CYP3AP1, CYP46A1, CYP4A11, CYP4A22, CYP4F11, CYP4F12, CYP4F2, CYP4F3, CYP4F8, CYP4Z1, CYP51A1, CYorf17, DAP3, DAPK1, DAXX, DAZ1, DAZ2, DAZ3, DAZ4, DAZAP2, DAZL, DBF4, DCAF12L1, DCAF12L2, DCAF13, DCAF4, DCAF4L1, DCAF4L2, DCAF6, DCAF8L1, DCAF8L2, DCLRE1C, DCTN6, DCUN1D1, DCUN1D3, DDA1, DDAH2, DDB2, DDR1, DDT, DDTL, DDX10, DDX11, DDX18, DDX19A, DDX19B, DDX23, DDX26B, DDX39B, DDX3X, DDX3Y, DDX50, DDX55, DDX56, DDX6, DDX60, DDX60L, DEF8, DEFB103A, DEFB103B, DEFB104A, DEFB104B, DEFB105A, DEFB105B, DEFB106A, DEFB106B, DEFB107A, DEFB107B, DEFB108B, DEFB130, DEFB131, DEFB4A, DEFB4B, DENND1C, DENR, DEPDC1, DERL2, DES12, DEXI, DGCR6, DGCR6L, DGKZ, DHFR, DHFRL1, DHRS2, DHRS4, DHRS4L1, DHRS4L2, DHRSX, DHX16, DHX29, DHX34, DHX40, DICER1, DIMT1, DIS3L2, DKKL1, DLEC1, DLST, DMBT1, DMRTC1, DMRTC1B, DNAH11, DNAJA1, DNAJA2, DNAJB1, DNAJB14, DNAJB3, DNAJB6, DNAJC1, DNAJC19, DNAJC24, DNAJC25-GNG10, DNAJC5, DNAJC7, DNAJC8, DNAJC9, DND1, DNM1, DOCK1, DOCK11, DOCK9, DOK1, DOM3Z, DONSON, DPCR1, DPEP2, DPEP3, DPF2, DPH3, DPM3, DPP3, DPPA2, DPPA3, DPPA4, DPPA5, DPRX, DPY19L1, DPY19L2, DPY19L3, DPY19L4, DPY30, DRAXIN, DRD5, DRG1, DSC2, DSC3, DSE, DSTN, DTD2, DTWD1, DTWD2, DTX2, DUOX1, DUOX2, DUSP12, DUSP5, DUSP8, DUT, DUXA, DYNC1I2, DYNC1L1, DYNLT1, DYNLT3, E2F3, EBLN1, EBLN2, EBPL, ECEL1, EDDM3A, EDDM3B, EED, EEF1A1, EEF1B2, EEF1D, EEF1E1, EEF1G, EFCAB3, EFEMP1, EFTUD1, EGFL8, EGLN1, EHD1, EHD3, EHMT2, EI24, EIF1, EIF1AX, EIF2A, EIF2C1, EIF2C3, EIF2S2, EIF2S3, EIF3A, EIF3C, EIF3CL, EIF3E, EIF3F, EIF3J, EIF3L, EIF3M, EIF4A1, EIF4A2, EIF4B, EIF4E, EIF4E2, EIF4EBP1, EIF4EBP2, EIF4H, EIF5, EIF5A, EIF5A2, EIF5AL1, ELF2, ELK1, ELL2, ELMO2, EMB, EMC3, EMR1, EMR2, EMR3, ENAH, ENDOD1, ENO1, ENO3, ENPEP, ENPP7, ENSA, EP300, EP400, EPB41L4B, EPB41L5, EPCAM, EPHA2, EPHB2, EPHB3, EPN2, EPN3, EPPK1, EPX, ERCC3, ERF, ERP29, ERP44, ERVV-1, ERVV-2, ESCO1, ESF1, ESPL1, ESPN, ESRRA, ETF1, ETS2, ETV3, ETV3L, EVA1C, EVPL, EVPLL, EWSR1, EXOC5, EXOC8, EXOG, EXOSC3, EXOSC6, EXTL2, EYS, EZR, F5, F8A1, F8A2, F8A3, FABP3, FABP5, FAF2, FAHD1, FAHD2A, FAHD2B, FAM103A1, FAM104B, FAM108A1, FAM108C1, FAM111B, FAM115A, FAM115C, FAM120A, FAM120B, FAM127A, FAM127B, FAM127C, FAM131C, FAM133B, FAM136A, FAM149B1, FAM151A, FAM153A, FAM153B, FAM154B, FAM156A, FAM156B, FAM157A, FAM157B, FAM163B, FAM165B, FAM175A, FAM177A1, FAM185A, FAM186A, FAM18B1, FAM18B2, FAM190B, FAM192A, FAM197Y1, FAM197Y3, FAM197Y4, FAM197Y6, FAM197Y7, FAM197Y8, FAM197Y9, FAM203A, FAM203B, FAM204A, FAM205A, FAM206A, FAM207A, FAM209A, FAM209B, FAM20B, FAM210B, FAM213A, FAM214B, FAM218A, FAM21A, FAM21B, FAM21C, FAM220A, FAM22A, FAM22D, FAM22F, FAM22G, FAM25A, FAM25B, FAM25C, FAM25G, FAM27E4P, FAM32A, FAM35A, FAM3C, FAM45A, FAM47A, FAM47B, FAM47C, FAM47E-STBD1, FAM58A, FAM60A, FAM64A, FAM72A, FAM72B, FAM72D, FAM76A, FAM83G, FAM86A, FAM86B2, FAM86C1, FAM89B, FAM8A1, FAM90A1, FAM91A1, FAM92A1, FAM96A, FAM98B, FAM9A, FAM9B, FAM9C, FANCD2, FANK1, FAR1, FAR2, FARP1, FARSB, FASN, FASTKD1, FAT1, FAU, FBLIM1, FBP2, FBRSL1, FBXL12, FBXO25, FBXO3, FBXO36, FBXO44, FBX06, FBXW10, FBXW11, FBXW2, FBXW4, FCF1, FCGBP, FCGRA, FCGR2A, FCGR2B, FCGR3A, FCGR3B, FCN1, FCN2, FCRL1, FCRL2, FCRL3, FCRL4, FCRL5, FCRL6, FDPS, FDX1, FEM1A, FEN1, FER, FFAR3, FGD5, FGF7, FGFR10P2, FH, FHL1, FIGLA, FKBP1A, FKBP4, FKBP6, FKBP8, FKBP9, FKBPL, FLG, FLG2, FL11, FLJ44635, FLNA, FLNB, FLNC, FLOT1, FLT1, FLYWCH1, FMN2, FN3K, FOLH1, FOLH1B, FOLR1, FOLR2, FOLR3, FOSL1, FOXA1, FOXA2, FOXA3, FOXD1, FOXD2, FOXD3, FOXD4L2, FOXD4L3, FOXD4L6, FOXF1, FOXF2, FOXH1, FOXN3, FOXO1, FOXO3, FPR2, FPR3, FRAT2, FREM2, FRG1, FRG2, FRG2B, FRG2C, FRMD6, FRMD7, FRMD8, FRMPD2, FSCN1, FSIP2, FTH1, FTHL17, FTL, FTO, FUNDC1, FUNDC2, FUT2, FUT3, FUT5, FUT6, FXN, FXR1, FZD2, FZD5, FZD8, G2E3, G3BP1, GABARAP, GABARAPL, GABBR, GABPA, GABRP, GABRR1, GABRR2, GAGE1, GAGE10, GAGE12C, GAGE12D, GAGE12E, GAGE12F, GAGE12G, GAGE12H, GAGE121, GAGE12J, GAGE13, GAGE2A, GAGE2B, GAGE2C, GAGE2D, GAGE2E, GAPDH, GAR1, GATS, GATSL1, GATSL2, GBA, GBP1, GBP2, GBP3, GBP4, GBP5, GBP6, GBP7, GCAT, GCDH, GCNT1, GCOM1, GCSH, GD2, GEMIN7, GEMIN8, GFRA2, GGCT, GGT1, GGT2, GGT5, GGTLC1, GGTLC2, GH1, GH2, GINS2, GJA1, GJC3, GK, GK2, GLB1L2, GLB1L3, GLDC, GLOD4, GLRA1, GLRA4, GLRX, GLRX3, GLRX5, GLTP, GLTSCR2, GLUD1, GLUL, GLYATL1, GLYATL2, GLYR1, GM2A, GMCL1, GMFB, GMPS, GNA11, GNAQ, GNAT2, GNG10, GNG5, GNGT1, GNL1, GNL3, GNL3L, GNPNAT1, GOLGA2, GOLGA4, GOLGA5, GOLGA6A, GOLGA6B, GOLGA6C, GOLGA6D, GOLGA6L1, GOLGA6L10, GOLGA6L2, GOLGA6L3, GOLGA6L4, GOLGA6L6, GOLGA6L9, GOLGA7, GOLGA8H, GOLGA8J, GOLGA8K, GOLGA80, GON4L, GOSR1, GOSR2, GOT2, GPAA1, GPANK1, GPAT2, GPATCH8, GPC5, GPCPD1, GPD2, GPHN, GPN1, GPR116, GPR125, GPR143, GPR32, GPR89A, GPR89B, GPR89C, GPS2, GPSM3, GPX1, GPX5, GPX6, GRAP, GRAPL, GRIA2, GRIA3, GRIA4, GRK6, GRM5, GRM8, GRPEL2, GSPT1, GSTA1, GSTA2, GSTA3, GSTA5, GSTM1, GSTM2, GSTM4, GSTM5, GSTO1, GSTT1, GSTT2, GSTT2B, GTF2A1L, GTF2H1, GTF2H2, GTF2H2C, GTF2H4, GTF21, GTF21RD1, GTF21RD2, GTF21RD2B, GTF3C6, GTPBP6, GUSB, GXYLT, GYG1, GYG2, GYPA, GYPB, GYPE, GZMB, GZMH, H1FOO, H2AFB1, H2AFB2, H2AFB3, H2AFV, H2AFX, H2AFZ, H2BFM, H2BFWT, H3F3A, H3F3B, H3F3C, HADHA, HADHB, HARS, HARS2, HAS3, HAUS1, HAUS4, HAUS6, HAVCR1, HAX1, HBA1, HBA2, HBB, HBD, HBG1, HBG2, HBS1L, HBZ, HCAR2, HCAR3, HCN2, HCN3, HCN4, HDAC1, HDGF, HDHD1, HEATR7A, HECTD4, HERC2, HIATL1, HIBCH, HIC1, HIC2, HIGD1A, HIGD2A, HINT1, HIST1H1B, HIST1H1C, HIST1H1D, HIST1H2AA, HIST1H2AB, HIST1H2AC, HIST1H2AD, HIST1H2AE, HIST1H2AG, HIST1H2AH, HIST1H2A1, HIST1H2AL, HIST1H2BB, HIST1H2BD, HIST1H2BE, HIST1H2BF, HIST1H2BH, HIST1H2BI, HIST1H2BK, HIST1H2BM, HIST1H2BN, HIST1H2BO, HIST1H3A, HIST1H3B, HIST1H3C, HIST1H3D, HIST1H3E, HIST1H3F, HIST1H3G, HIST1H3H, HIST1H31, HIST1H3J, HIST1H4A, HIST1H4B, HIST1H4C, HIST1H4D, HIST1H4E, HIST1H4F, HIST1H4G, HIST1H4H, HIST1H41, HIST1H4J, HIST1H4K, HIST1H4L, HIST2H2AA3, HIST2H2AB, HIST2H2AC, HIST2H2BE, HIST2H2BF, HIST2H3A, HIST2H3D, HIST2H4A, HIST2H4B, HIST3H2BB, HIST3H3, HIST4H4, HK2, HLA-A, HLA-B, HLA-C, HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB5, HLA-E, HLA-F, HLA-G, HMGA1, HMGB1, HMGB2, HMGB3, HMGCS1, HMGN1, HMGN2, HMGN3, HMGN4, HMX1, HMX3, HNRNPA1, HNRNPA3, HNRNPAB, HNRNPC, HNRNPCL, HNRNPD, HNRNPF, HNRNPH1, HNRNPH2, HNRNPH3, HNRNPK, HNRNPL, HNRNPM, HNRNPR, HNRNPU, HNRPDL, HOMER2, HORMAD1, HOXA2, HOXA3, HOXA6, HOXA7, HOXB2, HOXB3, HOXB6, HOXB7, HOXD3, HP, HPR, HPS1, HRG, HS3ST3A1, HS3ST3B1, HS6ST1, HSD17B1, HSD17B12, HSD17B4, HSD17B6, HSD17B7, HSD17B8, HSD3B1, HSD3B2, HSF2, HSFX1, HSFX2, HSP90AA1, HSP90AB1, HSP90B1, HSPA14, HSPA1A, HSPA1B, HSPA1L, HSPA2, HSPA5, HSPA6, HSPA8, HSPA9, HSPB1, HSPD1, HSPE1, HSPE1-MOB4, HSPG2, HTN1, HTN3, HTR3C, HTR3D, HTR3E, HTR7, HYDIN, HYPK, ARS, ID2, IDH1, ID1, IDS, IER3, IF16, IFIH1, IFIT1, IFIT1B, IFIT2, IFIT3, IFITM3, IFNA1, IFNA10, IFNA14, IFNA16, IFNA17, IFNA2, IFNA21, IFNA4, IFNA5, IFNA6, IFNA7, IFNA8, IFT122, IFT80, IGBP1, IGF2BP2, IGF2BP3, IGFL1, IGFL2, IGFN1, IGLL1, IGLL5, IGLON5, IGSF3, IHH, IK, IKBKG, IL17RE, IL18, IL28A, IL28B, IL29, IL32, IL3RA, IL6ST, IL9R, IMMP1L, IMMT, IMPA1, IMPACT, IMPDH1, ING5, INIP, INTS4, INTS6, IPMK, IPO7, IPPK, IQCB1, IREB2, IRX2, IRX3, IRX4, IRX5, IRX6, ISCA1, ISCA2, ISG20L2, ISL1, ISL2, IST1, ISY1-RAB43, ITFG2, ITGAD, ITGAM, ITGAX, ITGB1, ITGB6, ITIH6, ITLN1, ITLN2, ITSN1, KAL1, KANK1, KANSL1, KARS, KAT7, KATNBL1, KBTBD6, KBTBD7, KCNA1, KCNA5, KCNA6, KCNC1, KCNC2, KCNC3, KCNH2, KCNH6, KCNJ12, KCNJ4, KCNMB3, KCTD1, KCTD5, KCTD9, KDELC1, KDM5C, KDM5D, KDM6A, KHDC1, KHDC1L, KHSRP, KIAA0020, KIAA0146, KIAA0494, KIAA0754, KIAA0895L, KIAA1143, KIAA1191, KIAA1328, KIAA1377, KIAA1462, KIAA1549L, KIAA1551, KIAA1586, KIAA1644, KIAA1671, KIAA2013, KIF1C, KIF27, KIF4A, KIF4B, KIFC1, KIR2DL1, KIR2DL3, KIR2DL4, KIR2DS4, KIR3DL1, KIR3DL2, KIR3DL3, KLF17, KLF3, KLF4, KLF7, KLF8, KLHL12, KLHL13, KLHL15, KLHL2, KLHL5, KLHL9, KLK2, KLK3, KLRC1, KLRC2, KLRC3, KLRC4, KNTC1, KPNA2, KPNA4, KPNA7, KPNB1, KRAS, KRT13, KRT14, KRT15, KRT16, KRT17, KRT18, KRT19, KRT25, KRT27, KRT28, KRT3, KRT31, KRT32, KRT33A, KRT33B, KRT34, KRT35, KRT36, KRT37, KRT38, KRT4, KRT5, KRT6A, KRT6B, KRT6C, KRT71, KRT72, KRT73, KRT74, KRT75, KRT76, KRT8, KRT80, KRT81, KRT82, KRT83, KRT85, KRT86, KRTAP1-1, KRTAP1-3, KRTAP1-5, KRTAP10-10, KRTAP10-11, KRTAP10-12, KRTAP10-2, KRTAP10-3, KRTAP10-4, KRTAP10-7, KRTAP10-9, KRTAP12-1, KRTAP12-2, KRTAP12-3, KRTAP13-1, KRTAP13-2, KRTAP13-3, KRTAP13-4, KRTAP19-1, KRTAP19-5, KRTAP2-1, KRTAP2-2, KRTAP2-3, KRTAP2-4, KRTAP21-1, KRTAP21-2, KRTAP23-1, KRTAP3-2, KRTAP3-3, KRTAP4-12, KRTAP4-4, KRTAP4-6, KRTAP4-7, KRTAP4-9, KRTAP5-1, KRTAP5-10, KRTAP5-3, KRTAP5-4, KRTAP5-6, KRTAP5-8, KRTAP5-9, KRTAP6-1, KRTAP6-2, KRTAP6-3, KRTAP9-2, KRTAP9-3, KRTAP9-6, KRTAP9-8, KRTAP9-9, L1TD1, LAGE3, LAIR1, LAIR2, LAMTOR3, LANCL3, LAP3, LAPTM4B, LARP1, LARP1B, LARP4, LARP7, LCE1A, LCE1B, LCE1C, LCE1D, LCE1E, LCE1F, LCE2A, LCE2B, LCE2C, LCE2D, LCE3C, LCE3D, LCE3E, LCMT1, LCN1, LDHA, LDHAL6B, LDHB, LEFTY1, LEFTY2, LETM1, LGALS13, LGALS14, LGALS16, LGALS7, LGALS7B, LGALS9, LGALS9B, LGALS9C, LGMN, LGR6, LHB, LILRA1, LILRA2, LILRA3, LILRA4, LILRA5, LILRA6, LILRB1, LILRB2, LILRB3, LILRB4, LILRB5, LIMK2, LIMS1, LIN28A, LIN28B, LIN54, LLPH, LMLN, LNX1, LOC100129083, LOC100129216, LOC100129307, LOC100129636, LOC100130539, LOC100131107, LOC100131608, LOC100132154, LOC100132202, LOC100132247, LOC100132705, LOC100132858, LOC100132859, LOC100132900, LOC100133251, LOC100133267, LOC100133301, LOC100286914, LOC100287294, LOC100287368, LOC100287633, LOC100287852, LOC100288332, LOC100288646, LOC100288807, LOC100289151, LOC100289375, LOC100289561, LOC100505679, LOC100505767, LOC100505781, LOC100506248, LOC100506533, LOC100506562, LOC100507369, LOC100507607, LOC100652777, LOC100652871, LOC100652953, LOC100996256, LOC100996259, LOC100996274, LOC100996301, LOC100996312, LOC100996318, LOC100996337, LOC100996356, LOC100996369, LOC100996394, LOC100996401, LOC100996413, LOC100996433, LOC100996451, LOC100996470, LOC100996489, LOC100996541, LOC100996547, LOC100996567, LOC100996574, LOC100996594, LOC100996610, LOC100996612, LOC100996625, LOC100996631, LOC100996643, LOC100996644, LOC100996648, LOC100996675, LOC100996689, LOC100996701, LOC100996702, LOC377711, LOC388849, LOC391322, LOC391722, LOC401052, LOC402269, LOC440243, LOC440292, LOC440563, LOC554223, LOC642441, LOC642643, LOC642778, LOC642799, LOC643802, LOC644634, LOC645202, LOC645359, LOC646021, LOC646670, LOC649238, LOC728026, LOC728715, LOC728728, LOC728734, LOC728741, LOC728888, LOC729020, LOC729159, LOC729162, LOC729264, LOC729458, LOC729574, LOC729587, LOC729974, LOC730058, LOC730587, LOC731932, LOC732265, LONRF2, LPA, LPCAT3, LPGAT1, LRP5, LRPSL, LRRC16B, LRRC28, LRRC37A1, LRRC37A2, LRRC37A3, LRRC37B, LRRC57, LRRC59, LRRC8B, LRRFIP1, LSM12, LSM14A, LSM2, LSM3, LSP1, LTA, LTB, LUZP6, LY6G5B, LY6G5C, LY6G6C, LY6G6D, LY6G6F, LYPLA1, LYPLA2, LYRM2, LYRM5, LYST, LYZL1, LYZL2, LYZL6, MAD1L1, MAD2L1, MAGEA10-MAGEA5, MAGEA11, MAGEA12, MAGEA2B, MAGEA4, MAGEA5, MAGEA6, MAGEA9, MAGEB2, MAGEB4, MAGEB6, MAGEC1, MAGEC3, MAGED1, MAGED2, MAGED4, MAGED4B, MAGIX, MALL, MAMDC2, MAN1A1, MAN1A2, MANBAL, MANEAL, MAP1LC3B, MAP1LC3B2, MAP2K1, MAP2K2, MAP2K4, MAP3K13, MAP7, MAPK11P1L, MAPK6, MAPK81P1, MAPRE1, MAPT, MARC1, MARC2, MAS1L, MASP1, MAST1, MAST2, MAST3, MAT2A, MATR3, MBD3L2, MBD3L3, MBD3L4, MBD3L5, MBLAC2, MCCD1, MCF2L2, MCFD2, MCTS1, MDC1, ME1, ME2, MEAF6, MED13, MED15, MED25, MED27, MED28, MEF2A, MEF2BNB, MEIS3, MEMO1, MEP1A, MESP1, MEST, METAP2, METTL1, METTL15, METTL21A, METTL21D, METTL2A, METTL2B, METTL5, METTL7A, METTL8, MEX3B, MEX3D, MFAP2, MFF, MFN1, MFSD2B, MGAM, MICA, MICB, MINOS1, MIPEP, MK167, MK1671P, MKNK1, MKRN1, MLF11P, MLL3, MLLT10, MLLT6, MMADHC, MMP10, MMP23B, MMP3, MOB4, MOCS1, MOCS3, MOG, MORF4L1, MORF4L2, MPEG1, MPHOSPH10, MPHOSPH8, MPO, MPP7, MPPE1, MPRIP, MPV17L, MPZL1, MR1, MRC1, MRE11A, MRFAP1, MRFAPL1, MRGPRX2, MRGPRX3, MRGPRX4, MRPL10, MRPL11, MRPL19, MRPL3, MRPL32, MRPL35, MRPL36, MRPL45, MRPL48, MRPL50, MRPL51, MRPS10, MRPS16, MRPS17, MRPS18A, MRPS18B, MRPS18C, MRPS21, MRPS24, MRPS31, MRPS33, MRPS36, MRPS5, MRRF, MRS2, MRTO4, MS4A4A, MS4A4E, MS4A6A, MS4A6E, MSANTD2, MSANTD3, MSANTD3-TMEFF1, MSH5, MSL3, MSN, MST1, MSTO1, MSX2, MT1A, MT1B, MT1E, MT1F, MT1G, MT1H, MT1M, MT1X, MT2A, MTAP, MTCH1, MTFR1, MTHFD1, MTHFD1L, MTHFD2, MTIF2, MTIF3, MTMR12, MTMR9, MTRF1L, MTRNR2L1, MTRNR2L5, MTRNR2L6, MTRNR2L8, MTX1, MUC12, MUC16, MUC19, MUC20, MUC21, MUC22, MUC5B, MUC6, MX1, MX2, MXRA5, MXRA7, MYADM, MYEOV2, MYH1, MYH11, MYH13, MYH2, MYH3, MYH4, MYH6, MYH7, MYH8, MYH9, MYL12A, MYL12B, MYL6, MYL6B, MYLK, MYO5B, MZT1, MZT2A, MZT2B, NAA40, NAALAD2, NAB1, NACA, NACA2, NACAD, NACC2, NAGK, NAIP, NAMPT, NANOG, NANOGNB, NANP, NAP1L1, NAP1L4, NAPEPLD, NAPSA, NARG2, NARS, NASP, NAT1, NAT2, NAT8, NAT8B, NBAS, NBEA, NBEAL1, NBPF1, NBPF10, NBPF11, NBPF14, NBPF15, NBPF16, NBPF4, NBPF6, NBPF7, NBPF9, NBR1, NCAPD2, NCF1, NCOA4, NCOA6, NCOR1, NCR3, NDEL1, NDST3, NDST4, NDUFA4, NDUFA5, NDUFA9, NDUFAF2, NDUFAF4, NDUFB1, NDUFB3, NDUFB4, NDUFB6, NDUFB8, NDUFB9, NDUFS5, NDUFV2, NEB, NEDD8, NEDD8-MDP1, NEFH, NEFM, NEIL2, NEK2, NETO2, NEU1, NEUROD1, NEUROD2, NF1, NFE2L3, NFIC, NFIX, NFKBIL1, NFYB, NFYC, NHLH1, NHLH2, NHP2, NHP2L1, NICN1, NIF3L1, NIP7, NIPA2, NIPAL1, NIPSNAP3A, NIPSNAP3B, NKAP, NKX1-2, NLGN4X, NLGN4Y, NLRP2, NLRP5, NLRP7, NLRP9, NMD3, NME2, NMNAT1, NOB1, NOC2L, NOL11, NOLC1, NOMO1, NOMO2, NOMO3, NONO, NOP10, NOP56, NOS2, NOTCH2, NOTCH2NL, NOTCH4, NOX4, NPAP1, NPEPPS, NPIP, NPIPL3, NPM1, NPSR1, NR2F1, NR2F2, NR3C1, NRBF2, NREP, NRM, NSA2, NSF, NSFL1C, NSMAF, NSRP1, NSUN5, NT5C3, NT5DC1, NTM, NTPCR, NUBP1, NUDC, NUDT10, NUDT11, NUDT15, NUDT16, NUDT19, NUDT4, NUDT5, NUFIP1, NUP210, NUP35, NUP50, NUS1, NUTF2, NXF2, NXF2B, NXF3, NXF5, NXPE1, NXPE2, NXT1, OAT, OBP2A, OBP2B, OBSCN, OCLN, OCM, OCM2, ODC1, OFD1, OGDH, OGDHL, OGFOD1, OGFR, OLA1, ONECUT1, ONECUT2, ONECUT3, OPCML, OPN1LW, OPN1MW, OPN1MW2, OR10A2, OR10A3, OR10A5, OR10A6, OR10C1, OR10G2, OR10G3, OR10G4, OR10G7, OR10G8, OR10G9, OR10H1, OR10H2, OR10H3, OR10H4, OR10H5, OR10J3, OR10J5, OR10K1, OR10K2, OR10Q1, OR11A1, OR11G2, OR11H1, OR11H12, OR11H2, OR12D2, OR12D3, OR13C2, OR13C4, OR13C5, OR13C9, OR13D1, OR14J1, OR1A1, OR1A2, OR1D2, OR1D5, OR1E1, OR1E2, OR1F1, OR1J1, OR1J2, OR1J4, OR1L4, OR1L6, OR1M1, OR1S1, OR1S2, OR2A1, OR2A12, OR2A14, OR2A2, OR2A25, OR2A4, OR2A42, OR2A5, OR2A7, OR2AG1, OR2AG2, OR2B2, OR2B3, OR2B6, OR2F1, OR2F2, OR2H1, OR2H2, OR2J2, OR2J3, OR2L2, OR2L3, OR2L5, OR2L8, OR2M2, OR2M5, OR2M7, OR2S2, OR2T10, OR2T2, OR2T27, OR2T29, OR2T3, OR2T33, OR2T34, OR2T35, OR2T4, OR2T5, OR2T8, OR2V, OR2V2, OR2W1, OR3A1, OR3A2, OR3A3, OR4A15, OR4A47, OR4C12, OR4C13, OR4C46, OR4D1, OR4D10, OR4D11, OR4D2, OR4D9, OR4F16, OR4F21, OR4F29, OR4F3, OR4K15, OR4M1, OR4M2, OR4N2, OR4N4, OR4N5, OR4P4, OR4Q3, OR51A2, OR51A4, OR52E2, OR52E6, OR52E8, OR52H1, OR52I1, OR52I2, OR52J3, OR52K1, OR52K2, OR52L1, OR56A1, OR56A3, OR56A4, OR56A5, OR56B4, OR5AK2, OR5B2, OR5B3, OR5D16, OR5F1, OR5H14, OR5H2, OR5H6, OR5J2, OR5L1, OR5L2, OR5M1, OR5M10, OR5M3, OR5M8, OR5P3, OR5T1, OR5T2, OR5T3, OR5V1, OR6B2, OR6B3, OR6C6, OR7A10, OR7A5, OR7C1, OR7C2, OR7G3, OR8A1, OR8B12, OR8B2, OR8B3, OR8B8, OR8G2, OR8G5, OR8H1, OR8H2, OR8H3, OR8J1, OR8J3, OR9A2, OR9A4, OR9G1, ORC3, ORM1, ORM2, OSTC, OSTCP2, OTOA, OTOP1, OTUD4, OTUD7A, OTX2, OVOS, OXCT2, OXR1, OXT, P2RX6, P2RX7, P2RY8, PA2G4, PAAF1, PABPC1, PABPC1L2A, PABPC1L2B, PABPC3, PABPC4, PABPN1, PAEP, PAFAH1B1, PAFAH1B2, PAGE1, PAGE2, PAGE2B, PAGE5, PAICS, PAIP1, PAK2, PAM, PANK3, PARG, PARL, PARN, PARP1, PARP4, PARP8, PATL1, PBX1, PBX2, PCBD2, PCBP1, PCBP2, PCDH11X, PCDH11Y, PCDH8, PCDHA1, PCDHA11, PCDHA12, PCDHA13, PCDHA2, PCDHA3, PCDHA5, PCDHA6, PCDHA7, PCDHA8, PCDHA9, PCDHB10, PCDHB11, PCDHB12, PCDHB13, PCDHB15, PCDHB16, PCDHB4, PCDHB8, PCDHGA1, PCDHGA11, PCDHGA12, PCDHGA2, PCDHGA3, PCDHGA4, PCDHGA5, PCDHGA7, PCDHGA8, PCDHGA9, PCDHGB1, PCDHGB2, PCDHGB3, PCDHGB5, PCDHGB7, PCGF6, PCMTD1, PCNA, PCNP, PCNT, PCSK5, PCSK7, PDAP1, PDCD2, PDCD5, PDCD6, PDCD6IP, PDCL2, PDCL3, PDE4DIP, PDIA3, PDLIM1, PDPK1, PDPR, PDSS1, PDXDC1, PDZD11, PDZK1, PEBP1, PEF1, PEPD, PERP, PEX12, PEX2, PF4, PF4V1, PFDN1, PFDN4, PFDN6, PFKFB1, PFN1, PGA3, PGA4, PGA5, PGAM1, PGAM4, PGBD3, PGBD4, PGD, PGGT1B, PGK1, PGK2, PGM5, PHAX, PHB, PHC1, PHF1, PHF10, PHF2, PHF5A, PHKA1, PHLPP2, PHOSPHO1, PI3, PI4K2A, PI4KA, PIEZO2, PIGA, PIGF, PIGH, PIGN, PIGY, PIK3CA, PIK3CD, PILRA, PIN1, PIN4, PIP5KA, PITPNB, PKD1, PKM, PKP2, PKP4, PLA2G10, PLA2G12A, PLA2G4C, PLAC8, PLAC9, PLAGL2, PLD5, PLEC, PLEKHA3, PLEKHA8, PLEKHM1, PLG, PLGLB1, PLGLB2, PLIN2, PLIN4, PLK1, PLLP, PLSCR1, PLSCR2, PLXNA1, PLXNA2, PLXNA3, PLXNA4, PM20D1, PMCH, PMM2, PMPCA, PMS2, PNKD, PNLIP, PNLIPRP2, PNMA6A, PNMA6B, PNMA6C, PNMA6D, PNO1, PNPLA4, PNPT1, POLD2, POLE3, POLH, POLR2E, POLR2J, POLR2J2, POLR2J3, POLR2M, POLR3D, POLR3G, POLR3K, POLRMT, POM121, POM121C, POMZP3, POTEA, POTEC, POTED, POTEE, POTEF, POTEH, POTEI, POTEJ, POTEM, POU3F1, POU3F2, POU3F3, POU3F4, POU4F2, POU4F3, POU5F1, PPA1, PPAT, PPBP, PPCS, PPEF2, PPFIBP1, PPIA, PPIAL4C, PPIAL4D, PPIAL4E, PPIAL4F, PPIE, PPIG, PPIL1, PPIP5K1, PPIP5K2, PPM1A, PPP1R11, PPP1R12B, PPP1R14B, PPP1R18, PPP1R2, PPP1R26, PPP1R8, PPP2CA, PPP2CB, PPP2R2D, PPP2R3B, PPP2R5C, PPP2R5E, PPP4R2, PPP5C, PPP5D1, PPP6R2, PPP6R3, PPT2, PPY, PRADC1, PRAMEF1, PRAMEF10, PRAMEF11, PRAMEF12, PRAMEF13, PRAMEF14, PRAMEF15, PRAMEF16, PRAMEF17, PRAMEF18, PRAMEF19, PRAMEF20, PRAMEF21, PRAMEF22, PRAMEF23, PRAMEF25, PRAMEF3, PRAMEF4, PRAMEF5, PRAMEF6, PRAMEF7, PRAMEF8, PRAMEF9, PRB1, PRB2, PRB3, PRB4, PRDM7, PRDM9, PRDX1, PRDX2, PRDX3, PRDX6, PRELID1, PRG4, PRH1, PRH2, PRKAR1A, PRKCI, PRKRA, PRKRIR, PRKX, PRMT1, PRMT5, PRODH, PROKR1, PROKR2, PROS1, PRPF3, PRPF38A, PRPF4B, PRPS1, PRR12, PRR13, PRR20A, PRR20B, PRR20C, PRR20D, PRR20E, PRR21, PRR23A, PRR23B, PRR23C, PRR3, PRR5-ARHGAP8, PRRC2A, PRRC2C, PRRT1, PRSS1, PRSS21, PRSS3, PRSS41, PRSS42, PRSS48, PRUNE, PRY, PRY2, PSAT1, PSG1, PSG11, PSG2, PSG3, PSG4, PSG5, PSG6, PSG8, PSG9, PSIP1, PSMA6, PSMB3, PSMB5, PSMB8, PSMB9, PSMC1, PSMC2, PSMC3, PSMC5, PSMC6, PSMD10, PSMD12, PSMD2, PSMD4, PSMD7, PSMD8, PSME2, PSORS1C1, PSORS1C2, PSPH, PTBP1, PTCD2, PTCH1, PTCHD3, PTCHD4, PTEN, PTGES3, PTGES3L-AARSD, PTGR1, PTMA, PTMS, PTOV1, PTP4A1, PTP4A2, PTPN11, PTPN2, PTPN20A, PTPN20B, PTPRD, PTPRH, PTPRM, PTPRN2, PTPRU, PTTG1, PTTG2, PVRIG, PVRL2, PWWP2A, PYGB, PYGL, PYHIN, PYROXD1, PYURF, PYY, PZP, QRSL1, R3HDM2, RAB11A, RAB11FIP1, RAB13, RAB18, RAB1A, RAB1B, RAB28, RAB31, RAB40AL, RAB40B, RAB42, RAB43, RAB5A, RAB5C, RAB6A, RAB6C, RAB9A, RABGEF1, RABGGTB, RABL2A, RABL2B, RABL6, RAC1, RACGAP1, RAD1, RAD17, RAD21, RAD23B, RAD51AP1, RAD54L2, RAET1G, RAET1L, RALA, RALBP1, RALGAPA1, RAN, RANBP1, RANBP17, RANBP2, RANBP6, RAP1A, RAP1B, RAP1GDS1, RAP2A, RAP2B, RARS, RASA4, RASA4B, RASGRP2, RBAK, RBAK-LOC389458, RBBP4, RBBP6, RBM14-RBM4, RBM15, RBM17, RBM39, RBM4, RBM43, RBM48, RBM4B, RBM7, RBM8A, RBMS1, RBMS2, RBMX, RBMX2, RBMXL1, RBMXL2, RBMY1A1, RBMY1B, RBMY1D, RBMY1E, RBMY1F, RBMY1J, RBPJ, RCBTB1, RCBTB2, RCC2, RCN1, RCOR2, RDBP, RDH16, RDM1, RDX, RECQL, REG1A, REG1B, REG3A, REG3G, RELA, RERE, RETSAT, REV1, REXO4, RFC3, RFESD, RFK, RFPL1, RFPL2, RFPL3, RFPL4A, RFTN1, RFWD2, RGL2, RGPD1, RGPD2, RGPD3, RGPD4, RGPD5, RGPD6, RGPD8, RGS17, RGS19, RGS9, RHBDF1, RHCE, RHD, RHEB, RHOQ, RHOT1, RHOXF2, RHOXF2B, RHPN2, RIMBP3, RIMBP3B, RIMBP3C, RIMKLB, RING1, RLIM, RLN1, RLN2, RLTPR, RMND1, RMND5A, RNASE2, RNASE3, RNASE7, RNASE8, RNASEH1, RNASET2, RNF11, RNF123, RNF126, RNF13, RNF138, RNF14, RNF141, RNF145, RNF152, RNF181, RNF2, RNF216, RNF39, RNF4, RNF5, RNF6, RNFT1, RNMTL1, RNPC3, RNPS1, ROB02, ROCK1, ROCK2, ROPN1, ROPN1B, RORA, RP9, RPA2, RPA3, RPAP2, RPE, RPF2, RPGR, RPL10, RPL10A, RPL10L, RPL12, RPL13, RPL14, RPL15, RPL17, RPL17-C180RF32, RPL18A, RPL19, RPL21, RPL22, RPL23, RPL23A, RPL24, RPL26, RPL26L1, RPL27, RPL27A, RPL29, RPL3, RPL30, RPL31, RPL32, RPL35, RPL35A, RPL36, RPL36A, RPL36A-HNRNPH2, RPL36AL, RPL37, RPL37A, RPL39, RPL4, RPL41, RPL5, RPL6, RPL7, RPL7A, RPL7L1, RPL8, RPL9, RPLP0, RPLP1, RPP21, RPS10, RPS10-NUDT3, RPS11, RPS13, RPS14, RPS15, RPS15A, RPS16, RPS17, RPS17L, RPS18, RPS19, RPS2, RPS20, RPS23, RPS24, RPS25, RPS26, RPS27, RPS27A, RPS28, RPS3, RPS3A, RPS4X, RPS4Y1, RPS4Y2, RPS5, RPS6, RPS6KB1, RPS7, RPS8, RPS9, RPSA, RPTN, RRAGA, RRAGB, RRAS2, RRM2, RRN3, RRP7A, RSL24D1, RSPH10B, RSPH10B2, RSPO2, RSRC1, RSU1, RTEL1, RTN3, RTN41P1, RTN4R, RTP1, RTP2, RUFY3, RUNDC1, RUVBL2, RWDD1, RWDD4, RXRB, RYK, S100A11, S100A7L2, SAA1, SAA2, SAA2-SAA4, SAE1, SAFB, SAFB2, SAGE1, SALL1, SALL4, SAMD12, SAMD9, SAMD9L, SAP18, SAP25, SAP30, SAPCD1, SAPCD2, SAR1A, SATL1, SAV1, SAYSD1, SBDS, SBF1, SCAMP1, SCAND3, SCD, SCGB1D1, SCGB1D2, SCGB1D4, SCGB2A1, SCGB2A2, SCGB2B2, SCN10A, SCN1A, SCN2A, SCN3A, SCN4A, SCN5A, SCN9A, SCOC, SCXA, SCXB, SCYL2, SDAD1, SDCBP, SDCCAG3, SDHA, SDHB, SDHC, SDHD, SDR42E1, SEC11A, SEC14L1, SEC14L4, SEC14L6, SEC61B, SEC63, SELT, SEMA3E, SEMG1, SEMG2, SEPHS1, SEPHS2, SEPT14, SEPT7, SERBP1, SERF1A, SERF1B, SERF2, SERHL2, SERPINB3, SERPINB4, SERPINH, SET, SETD8, SF3A2, SF3A3, SF3B14, SF3B4, SFR1, SFRP4, SFTA2, SFTPA1, SFTPA2, SH2D1B, SH3BGRL3, SH3GL1, SHANK2, SHC1, SHCBP1, SHFM1, SHH, SHISA5, SHMT1, SHOX, SHQ1, SHROOM2, SIGLEC10, SIGLEC11, SIGLEC12, SIGLEC14, SIGLEC5, SIGLEC6, SIGLEC7, SIGLEC8, SIGLEC9, SIMC1, SIN3A, SIRPA, SIRPB1, SIRPG, SIX1, SIX2, SKA2, SKIV2L, SKOR2, SKP1, SKP2, SLAIN2, SLAMF6, SLC10A5, SLC16A14, SLC16A6, SLC19A3, SLC22A10, SLC22A11, SLC22A12, SLC22A24, SLC22A25, SLC22A3, SLC22A4, SLC22A5, SLC22A9, SLC25A13, SLC25A14, SLC25A15, SLC25A20, SLC25A29, SLC25A3, SLC25A33, SLC25A38, SLC25A47, SLC25A5, SLC25A52, SLC25A53, SLC25A6, SLC29A4, SLC2A13, SLC2A14, SLC2A3, SLC31A1, SLC33A1, SLC35A4, SLC35E1, SLC35E2, SLC35E2B, SLC35G3, SLC35G4, SLC35G5, SLC35G6, SLC36A1, SLC36A2, SLC39A1, SLC39A7, SLC44A4, SLC4A1AP, SLC52A1, SLC52A2, SLC5A6, SLC5A8, SLC6A14, SLC6A6, SLC6A8, SLC7A5, SLC8A2, SLC8A3, SLC9A2, SLC9A4, SLC9A7, SLCO1B1, SLCO1B3, SLCO1B7, SLFN11, SLFN12, SLFN12L, SLFN13, SLFN5, SLIRP, SLMO2, SLX1A, SLX1B, SMARCE1, SMC3, SMC5, SMEK2, SMG1, SMN1, SMN2, SMR3A, SMR3B, SMS, SMU1, SMURF2, SNAI1, SNAPC4, SNAPC5, SNF8, SNRNP200, SNRPA1, SNRPB2, SNRPC, SNRPD1, SNRPD2, SNRPE, SNRPG, SNRPN, SNW1, SNX19, SNX25, SNX29, SNX5, SNX6, SOCS5, SOCS6, SOGA1, SOGA2, SON, SOX1, SOX10, SOX14, SOX2, SOX30, SOX5, SOX9, SP100, SP140, SP140L, SP3, SP5, SP8, SP9, SPACA5, SPACA5B, SPACA7, SPAG11A, SPAG11B, SPANXA1, SPANXB1, SPANXD, SPANXN2, SPANXN5, SPATA16, SPATA20, SPATA31A1, SPATA31A2, SPATA31A3, SPATA31A4, SPATA31A5, SPATA31A6, SPATA31A7, SPATA31C1, SPATA31C2, SPATA31D1, SPATA31D3, SPATA31D4, SPATA31E1, SPCS2, SPDYE1, SPDYE2, SPDYE2L, SPDYE3, SPDYE4, SPDYE5, SPDYE6, SPECC1, SPECC1L, SPHAR, SPIC, SPIN1, SPIN2A, SPIN2B, SPOPL, SPPL2A, SPPL2C, SPR, SPRR1A, SPRR1B, SPRR2A, SPRR2B, SPRR2D, SPRR2E, SPRR2F, SPRY3, SPRYD4, SPTLC, SRD5A1, SRD5A3, SREK1IP1, SRGAP2, SRP14, SRP19, SRP68, SRP72, SRP9, SRPK1, SRPK2, SRRM1, SRSF1, SRSF10, SRSF11, SRSF3, SRSF6, SRSF9, SRXN1, SS18L2, SSB, SSBP2, SSBP3, SSBP4, SSNA1, SSR3, SSX1, SSX2, SSX2B, SSX3, SSX4, SSX4B, SSX5, SSX7, ST13, ST3GAL1, STAG3, STAR, STAT5A, STAT5B, STAU1, STAU2, STBD1, STEAP1, STEAP1B, STH, STIP1, STK19, STK24, STK32A, STMN1, STMN2, STMN3, STRADB, STRAP, STRC, STRN, STS, STUB1, STX18, SUB1, SUCLA2, SUCLG2, SUDS3, SUGP1, SUGT1, SULT1A1, SULT1A2, SULT1A3, SULT1A4, SUMF2, SUMO1, SUMO2, SUPT16H, SUPT4H1, SUSD2, SUZ12, SVIL, SW15, SYCE2, SYNCRIP, SYNGAP, SYNGR2, SYT14, SYT15, SYT2, SYT3, SZRD1, TAAR6, TAAR8, TACC1, TADA1, TAF1, TAF15, TAFL, TAF4B, TAF5L, TAF9, TAF9B, TAGLN2, TALDO1, TANC2, TAP1, TAP2, TAPBP, TARBP2, TARDBP, TARP, TAS2R19, TAS2R20, TAS2R30, TAS2R39, TAS2R40, TAS2R43, TAS2R46, TAS2R50, TASP1, TATDN1, TATDN2, TBC1D26, TBC1D27, TBC1D28, TBC1D29, TBC1D2B, TBC1D3, TBC1D3B, TBC1D3C, TBC1D3F, TBC1D3G, TBC1D3H, TBCA, TBCCD1, TBL1X, TBL1XR1, TBL1Y, TBPL1, TBX20, TC2N, TCEA1, TCEAL2, TCEAL3, TCEAL5, TCEB1, TCEB2, TCEB3B, TCEB3C, TCEB3CL, TCEB3CL2, TCERG1L, TCF19, TCF3, TCHH, TCL1B, TCOF1, TCP1, TCP10, TCP10L, TCP10L2, TDG, TDGF1, TDRD1, TEAD1, TEC, TECR, TEKT4, TERF1, TERF2IP, TET1, TEX13A, TEX13B, TEX28, TF, TFB2M, TFDP3, TFG, TGIF1, TGIF2, TGIF2LX, TGIF2LY, THAP3, THAP5, THEM4, THOC3, THRAP3, THSD1, THUMPD1, TIMM17B, TIMM23B, TIMM8A, TIMM8B, TIMP4, TIPIN, TJAP1, TJP3, TLE1, TLE4, TLK1, TLK2, TLL1, TLR1, TLR6, TMA16, TMA7, TMC6, TMCC1, TMED10, TMED2, TMEM126A, TMEM128, TMEM132B, TMEM132C, TMEM14B, TMEM14C, TMEM161B, TMEM167A, TMEM183A, TMEM183B, TMEM185A, TMEM185B, TMEM189-UBE2V1, TMEM191B, TMEM191C, TMEM230, TMEM231, TMEM236, TMEM242, TMEM251, TMEM254, TMEM30B, TMEM47, TMEM69, TMEM80, TMEM92, TMEM97, TMEM98, TMLHE, TMPRSS11E, TMSB10, TMSB15A, TMSB15B, TMSB4X, TMSB4Y, TMTC1, TMTC4, TMX1, TMX2, TNC, TNF, TNFRSF10A, TNFRSF10B, TNFRSF10C, TNFRSF10D, TNFRSF13B, TNFRSF14, TNIP2, TNN, TNPO1, TNRC18, TNXB, TOB2, TOE1, TOMM20, TOMM40, TOMM6, TOMM7, TOP1, TOP3B, TOR1B, TOR3A, TOX4, TP53TG3, TP53TG3B, TP53TG3C, TPD52L2, TP11, TPM3, TPM4, TPMT, TPRKB, TPRX1, TPSAB1, TPSB2, TPSD1, TPT1, TPTE, TPTE2, TRA2A, TRAF6, TRAPPC2, TRAPPC2L, TREH, TREML2, TREML4, TRIM10, TRIM15, TRIM16, TRIM16L, TRIM26, TRIM27, TRIM31, TRIM38, TRIM39, TRIM39-RPP21, TRIM40, TRIM43, TRIM43B, TRIM48, TRIM49, TRIM49B, TRIM49C, TRIM49DP, TRIM49L1, TRIM50, TRIM51, TRIM51GP, TRIM60, TRIM61, TRIM64, TRIM64B, TRIM64C, TRIM73, TRIM74, TRIM77P, TRIP11, TRMT1, TRMT11, TRMT112, TRMT2B, TRNT1, TRO, TRPA1, TRPC6, TRPV5, TRPV6, TSC22D3, TSEN15, TSEN2, TSPAN11, TSPY1, TSPY10, TSPY2, TSPY3, TSPY4, TSPY8, TSPYL1, TSPYL6, TSR1, TSSK1B, TSSK2, TTC28, TTC3, TTC30A, TTC30B, TTC4, TTL, TTLL12, TTLL2, TTN, TUBA1A, TUBA1B, TUBA1C, TUBA3C, TUBA3D, TUBA3E, TUBA4A, TUBA8, TUBB, TUBB2A, TUBB2B, TUBB3, TUBB4A, TUBB4B, TUBB6, TUBB8, TUBE1, TUBG1, TUBG2, TUBGCP3, TUBGCP6, TUFM, TWF1, TWIST2, TXLNG, TXN2, TXNDC2, TXNDC9, TYR, TYRO3, TYW1, TYW1B, U2AF1, UAP1, UBA2, UBA5, UBD, UBE2C, UBE2D2, UBE2D3, UBE2D4, UBE2E3, UBE2F, UBE2H, UBE2L3, UBE2M, UBE2N, UBE2Q2, UBE2S, UBE2V1, UBE2V2, UBE2W, UBE3A, UBFD1, UBQLN1, UBQLN4, UBTFL1, UBXN2B, UFD1L, UFM1, UGT1A10, UGT1A3, UGT1A4, UGT1A5, UGT1A7, UGT1A8, UGT1A9, UGT2A1, UGT2A2, UGT2A3, UGT2B10, UGT2B11, UGT2B15, UGT2B17, UGT2B28, UGT2B4, UGT2B7, UGT3A2, UHRF1, UHRF2, ULBP1, ULBP2, ULBP3, ULK4, UNC93A, UNC93B1, UPF3A, UPK3B, UPK3BL, UQCR10, UQCRB, UQCRFS1, UQCRH, UQCRQ, USP10, USP12, USP13, USP17L10, USP17L11, USP17L12, USP17L13, USP17L15, USP17L17, USP17L18, USP17L19, USP17L1P, USP17L2, USP17L20, USP17L21, USP17L22, USP17L24, USP17L25, USP17L26, USP17L27, USP17L28, USP17L29, USP17L3, USP17L30, USP17L4, USP17L5, USP17L7, USP17L8, USP18, USP22, USP32, USP34, USP6, USP8, USP9X, USP9Y, UTP14A, UTP14C, UTP18, UTP6, VAMP5, VAMP7, VAPA, VARS, VARS2, VCX, VCX2, VCX3A, VCX3B, VCY, VCY1B, VDAC1, VDAC2, VDAC3, VENTX, VEZF1, VKORC1, VKORC1L1, VMA21, VN1R4, VNN1, VOPP1, VPS26A, VPS35, VPS37A, VPS51, VPS52, VSIG10, VTCN1, VT11B, VWA5B2, VWA7, VWA8, VWF, WARS, WASF2, WASF3, WASH1, WBP1, WBP11, WBP1L, WBSCR16, WDR12, WDR45, WDR45L, WDR46, WDR49, WDR59, WDR70, WDR82, WDR89, WFDC10A, WFDC10B, WHAMM, WHSC1L1, WIP12, WIZ, WNT3, WNT3A, WNT5A, WNT5B, WNT9B, WRN, WTAP, WWC2, WWC3, WWP1, XAGE1A, XAGE1B, XAGE1C, XAGE1D, XAGE1E, XAGE2, XAGE3, XAGE5, XBP1, XCL1, XCL2, XG, XIAP, XKR3, XKR8, XKRY, XKRY2, XPO6, XPOT, XRCC6, YAP1, YBX1, YBX2, YES1, YME1L1, YPEL5, YTHDC1, YTHDF1, YTHDF2, YWHAB, YWHAE, YWHAQ, YWHAZ, YY1, YY1AP1, ZAN, ZBED1, ZBTB10, ZBTB12, ZBTB22, ZBTB44, ZBTB45, ZBTB8OS, ZBTB9, ZC3H11A, ZC3H12A, ZCCHC10, ZCCHC12, ZCCHC17, ZCCHC18, ZCCHC2, ZCCHC7, ZCCHC9, ZCRB1, ZDHHC11, ZDHHC20, ZDHHC3, ZDHHC8, ZEB2, ZFAND5, ZFAND6, ZFP106, ZFP112, ZFP14, ZFP57, ZFP64, ZFP82, ZFR, ZFX, ZFY, ZFYVE1, ZFYVE9, ZIC1, ZIC2, ZIC3, ZIC4, ZIK1, ZKSCAN3, ZKSCAN4, ZMIZ1, ZMIZ2, ZMYM2, ZMYM5, ZNF100, ZNF101, ZNF107, ZNF114, ZNF117, ZNF12, ZNF124, ZNF131, ZNF135, ZNF14, ZNF140, ZNF141, ZNF146, ZNF155, ZNF160, ZNF167, ZNF17, ZNF181, ZNF185, ZNF20, ZNF207, ZNF208, ZNF212, ZNF221, ZNF222, ZNF223, ZNF224, ZNF225, ZNF226, ZNF229, ZNF230, ZNF233, ZNF234, ZNF235, ZNF248, ZNF253, ZNF254, ZNF257, ZNF259, ZNF26, ZNF264, ZNF266, ZNF267, ZNF280A, ZNF280B, ZNF282, ZNF283, ZNF284, ZNF285, ZNF286A, ZNF286B, ZNF300, ZNF302, ZNF311, ZNF317, ZNF320, ZNF322, ZNF323, ZNF324, ZNF324B, ZNF33A, ZNF33B, ZNF341, ZNF347, ZNF35, ZNF350, ZNF354A, ZNF354B, ZNF354C, ZNF366, ZNF37A, ZNF383, ZNF396, ZNF41, ZNF415, ZNF416, ZNF417, ZNF418, ZNF419, ZNF426, ZNF429, ZNF43, ZNF430, ZNF431, ZNF433, ZNF439, ZNF44, ZNF440, ZNF441, ZNF442, ZNF443, ZNF444, ZNF451, ZNF460, ZNF468, ZNF470, ZNF479, ZNF480, ZNF484, ZNF486, ZNF491, ZNF492, ZNF506, ZNF528, ZNF532, ZNF534, ZNF543, ZNF546, ZNF547, ZNF548, ZNF552, ZNF555, ZNF557, ZNF558, ZNF561, ZNF562, ZNF563, ZNF564, ZNF57, ZNF570, ZNF578, ZNF583, ZNF585A, ZNF585B, ZNF586, ZNF587, ZNF587B, ZNF589, ZNF592, ZNF594, ZNF595, ZNF598, ZNF605, ZNF607, ZNF610, ZNF613, ZNF614, ZNF615, ZNF616, ZNF620, ZNF621, ZNF622, ZNF625, ZNF626, ZNF627, ZNF628, ZNF646, ZNF649, ZNF652, ZNF655, ZNF658, ZNF665, ZNF673, ZNF674, ZNF675, ZNF676, ZNF678, ZNF679, ZNF680, ZNF681, ZNF682, ZNF69, ZNF700, ZNF701, ZNF705A, ZNF705B, ZNF705D, ZNF705E, ZNF705G, ZNF706, ZNF708, ZNF709, ZNF710, ZNF714, ZNF716, ZNF717, ZNF718, ZNF720, ZNF721, ZNF726, ZNF727, ZNF728, ZNF729, ZNF732, ZNF735, ZNF736, ZNF737, ZNF746, ZNF747, ZNF749, ZNF75A, ZNF75D, ZNF761, ZNF763, ZNF764, ZNF765, ZNF766, ZNF770, ZNF773, ZNF775, ZNF776, ZNF777, ZNF780A, ZNF780B, ZNF782, ZNF783, ZNF791, ZNF792, ZNF799, ZNF805, ZNF806, ZNF808, ZNF812, ZNF813, ZNF814, ZNF816, ZNF816-ZNF321P, ZNF823, ZNF829, ZNF83, ZNF836, ZNF84, ZNF841, ZNF844, ZNF845, ZNF850, ZNF852, ZNF878, ZNF879, ZNF880, ZNF90, ZNF91, ZNF92, ZNF93, ZNF98, ZNF99, ZNRD1, ZNRF2, ZP3, ZRSR2, ZSCAN5A, ZSCAN5B, ZSCAN5D, ZSWIM5, ZXDA, ZXDB, ZXDC, portions thereof, modified forms thereof or combinations thereof. In certain embodiments, a desired nucleic acid or gene is selected from one ormore of ABL1, ANGPTL4, APOB, APOC3, ASGR1, BRCA1, BRCA2, BRAF, CD19, CD36, CFTR, DMD, FMR1, HTT, TCF4, CEP290, G6PC, PCSK9, EYA4, GJB2, SLC26A4, ABCA4, CNGA3, CNGB3, MERTK, MYO7A, REP1, RHO, RPE65, RS1, USH2A, PD1, PD-L1 (or CD274), EGFR, RAF, RAS, portions thereof, and modified forms thereof.

In certain embodiments a method of editing a genome of an organism or a cell comprises introducing one or more ANAGO, or a composition thereof described herein, into one or more cells. In certain embodiments a method of editing a genome of an organism or cell is a method of modifying a target sequence in a genome of a cell, organism or subject. In certain embodiments a method of editing a genome of an organism or cell comprises introducing one or more ANAGO described herein into one or more cells. One or more nucleic acid can be introduced into one or more cells by any suitable method.

In some embodiments, a method described herein comprises introducing into a eukaryotic cell, (i) an ANAGO in a form of protein or in vitro transcribed messenger RNA; and (ii) one or more nucleic acid donors (one or more donor sequences). In some embodiments, a donor nucleic acid comprises a desired nucleic acid flanked by a 5'-flanking sequence and a 3' flanking sequence. In some embodiments, a method described herein comprises introducing into a human cell, (i) an ANAGO having a sequence encoded by e.g., a nucleic acid of SEQ ID NO:1, nucleic acid of SEQ ID NO:2, nucleic acid of SEQ ID NO:3, or nucleic acid of SEQ ID NO:4, and (ii) a donor nucleic acid described herein. In certain embodiments the donor nucleic acid sequence comprises a desired nucleic acid. In some embodiments, the method induces, results in, or provides a modification of a target sequence. A modification of a target sequence may comprise an insertion, deletion, or replacement of one or more nucleotides of the target sequence. In some embodiments, a modification of a target sequence comprises an insertion, deletion or replacement of a single nucleotide of the target sequence. In certain embodiments, the method results in integration or insertion of a desired nucleic acid into the genome of the cell. In certain embodiments, the method results in replacement of a dysfunctional or mutated endogenous gene, or portion thereof, in the genome of a cell, with a wild-type, modified and/or a more functional gene. In certain embodiments, the method results in targeted disruption of an endogenous or wild type gene in the genome of the cell.

A cell may be contacted with ANAGO, and a donor sequence at the same time, or at different times. For example, a cell may be contacted with an ANAGO, followed by contacting the cell with a donor sequence within a time range of a week, 0 to 72 hours, 0 to 24 hours, 0 to 12 hours, 0 to 6 hours or 0 to 4 hours. A cell may be contacted with the nucleic acids described herein in any order.

Pharmaceutical Compositions

In some embodiments a pharmaceutical composition comprises one or more nucleic acids described herein.

In some embodiments, a pharmaceutical composition comprises one or more species-specific ANAGO described herein.

In some embodiments, a composition comprises one or more species-specific ANAGO, one or more nucleic acid donors, one or more NLS, one or more short peptide tag sequence (TAG) described herein. In some embodiments, a composition comprises one or more human ANAGO, one or more nucleic acid donors, one or more NLS, one or more TAG described herein. In some embodiments, a composition comprises one or more human ANAGO encoded with nucleic acid sequence of SEQ ID NO:1, SEQ ID NO:2, SEQ ID NO:3, or SEQ ID NO:4, one or more nucleic acid donors, one or more NLS, one or more TAG described herein. In some embodiments, a composition comprises one or more human ANAGO encoded with nucleic acid sequence of SEQ ID NO:1, one or more nucleic acid donors, one or more NLS, one or more TAG described herein. In some embodiments, a composition comprises one or more human ANAGO encoded with nucleic acid sequence of SEQ ID NO:2, one or more nucleic acid donors, one or more NLS, one or more TAG described herein. In some embodiments, a composition comprises one or more human ANAGO encoded with nucleic acid sequence of SEQ ID NO:3, one or more nucleic acid donors, one or more NLS, one or more TAG described herein. In some embodiments, a composition comprises one or more human ANAGO encoded with nucleic acid sequence of SEQ ID NO:4, one or more nucleic acid donors, one or more NLS, one or more TAG described herein.

An ANAGO, including the protein or the nucleic acid encoding the protein, may be in a pharmaceutical composition. The exact formulation and route of administration can be chosen by the individual physician in view of the patient's condition. See, e.g., Fingl et al. 1975, in "The Pharmacological Basis of Therapeutics," Ch. 1, p. 1; which is incorporated herein by reference in its entirety. The pharmaceutical composition or formulation may be administered by any suitable route of delivery including, but not limited to, topical or local (e.g., transdermally or cutaneously, (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranially, intra-articular, into a joint space, intracardiac (into the heart), intracavernous injection, intralesional (into a skin lesion), intraosseous infusion (into the bone marrow), intrathecal (into the spinal canal), intrauterine, intravaginal, intravesical infusion, intravitreal), the like or combinations thereof.

Appropriate excipients for use in a pharmaceutical composition comprising an ANAGO, including the protein or the nucleic acid encoding the protein, may include, for example, one or more carriers, binders, fillers, vehicles, tonicity agents, buffers, disintegrates, surfactants, dispersion or suspension aids, thickening or emulsifying agents, preservatives, lubricants and the like or combinations thereof, as suited to a particular dosage from desired. Remington's Pharmaceutical Sciences, 18th Ed., A. R. Gennaro, ed., Mack Publishing Company (1995) discloses various carriers used in formulating pharmaceutically acceptable compositions and known techniques for the preparation thereof. This document is incorporated herein by reference in its entirety.

In addition to water or another solvent, a liquid dosage form for IV, injection, topical, or oral administration to a mammal, including a human being, may contain excipients such as bulking agents (such as mannitol, lactose, sucrose, trehalose, sorbitol, glucose, raffinose, glycine, histidine, polyvinylpyrrolidone, etc.), tonicity agents (e.g. dextrose, glycerin, mannitol, sodium chloride, etc.), buffers (e.g. acetate, e.g. sodium acetate, acetic acid, ammonium acetate, ammonium sulfate, ammonium hydroxide, citrate, tartrate, phosphate, triethanolamine, arginine, aspartate, benzenesulfonic acid, benzoate, bicarbonate, borate, carbonate, succinate, sulfate, tartrate, tromethamine, diethanolamine etc.), preservatives (e.g. phenol, m-cresol, a paraben, such as methylparaben, propylparaben, butylparaben, myristyl gamma-picolinium chloride, benzalkonium chloride, benzethonium chloride, benzyl alcohol, 2-penoxyethanol, chlorobutanol, thimerosal, phenymercuric salts, etc.), surfactants (e.g. polyoxyethylene sorbitan monooleate or Tween 80, sorbitan monooleate polyoxyethylene sorbitan monolaurate or Tween 20, lecithin, a polyoxyethylene-polyoxypropylen copolymer, etc.), additional solvents (e.g. propylene glycol, glycerin, ethanol, polyethylene glycol, sorbitol, dimethylacetamide, Cremophor EL, benzyl benzoate, castor oil, cottonseed oil, N-methyl-2-pyrrolidone, PEG, PEG 300, PEG 400, PEG 600, PEG 600, PEG 3350, PEG 400, poppyseed oil, propylene glycol, safflower oil, vegetable oil, etc.) chelating agents (such as calcium disodium EDTA, disodium EDTA, sodium EDTA, calcium versetamide Na, calteridol, DTPA), or other excipients.

In certain embodiments, the amount of a nucleic acid described herein can be any sufficient amount to prevent, treat, reduce the severity of, delay the onset of, or alleviate a symptom of a disease as contemplated herein or a specific indication as described herein.

Certain embodiments provide pharmaceutical compositions suitable for use in the technology, which include compositions where the active ingredients are contained in an amount effective to achieve its intended purpose. A "therapeutically effective amount" means an amount sufficient to prevent, treat, reduce the severity of, delay the onset of, or inhibit a symptom of a disease. The symptom can be a symptom already occurring or expected to occur. Determination of a therapeutically effective amount is well within the capability of those skilled in the art, especially in light of the detailed disclosure provided herein.

The term "an amount sufficient" as used herein refers to the amount or quantity of an active agent (e.g., a nucleic acid described herein, an ANAGO described herein, an antibacterial medication, and/or a combination of these active agents) presents in a pharmaceutical composition that is determined to be high enough to prevent, treat, reduce the severity of, delay the onset of, or inhibit a symptom of a disease and low enough to minimize unwanted adverse reactions.

The ANAGO, in a form of protein or nucleic acid, and compositions comprising ANAGO as described herein can be administered at a suitable dose, e.g., at a suitable volume and concentration depending on the route of administration. Within certain embodiments, dosages of administered ANAGO can be from 0.01-500 mg/kg (e.g., per kg body weight of a subject), such as 0.01-0.02 mg/kg, 0.02-0.03 mg/kg, 0.03-0.04 mg/kg, 0.04-0.05 mg/kg, 0.05-0.06 mg/kg, 0.06-0.07 mg/kg, 0.07-0.08 mg/kg, 0.08-0.09 mg/kg, 0.09-0.1 mg/kg, 0.1-0.2 mg/kg, 0.2-0.3 mg/kg, 0.3-0.4 mg/kg, 0.4-0.5 mg/kg, 0.5-0.6 mg/kg, 0.6-0.7 mg/kg, 0.7-0.8 mg/kg, 0.8-0.9 mg/kg, 0.9-1 mg/kg, 1-2 mg/kg, 2-3 mg/kg, 3-4 mg/kg, 4-5 mg/kg, 5-6 mg/kg, 6-7 mg/kg, 7-8 mg/kg, 8-9 mg/kg, 9-10 mg/kg, 10-20 mg/kg, 20-30 mg/kg, 30-40 mg/kg, 40-50 mg/kg, 50-60 mg/kg, 60-70 mg/kg, 70-80 mg/kg, 80-90 mg/kg, 90-100 mg/kg, 100-200 mg/kg, 200-

300 mg/kg, 300-400 mg/kg, 400-500 mg/kg, 0.01-0.1 mg/kg, 0.1-1 mg/kg, 1-10 mg/kg, 10-100 mg/kg, or 100-500 mg/kg.

In some embodiments a nucleic acid described herein comprises one or more distinguishable identifiers. Any suitable distinguishable identifier and/or detectable identifier can be used for a composition or method described herein. In certain embodiments a distinguishable identifier can be directly or indirectly associated with (e.g., bound to) a nucleic acid described herein. For example, a distinguishable identifier can be covalently or non-covalently bound to a nucleic acid described herein. In some embodiments a distinguishable identifier is bound to or associated with a nucleic acid described herein and/or a member of binding pair that is covalently or non-covalently bound to a nucleic acid described herein. In some embodiments a distinguishable identifier is reversibly associated with a nucleic acid described herein. In certain embodiments a distinguishable identifier that is reversibly associated with a nucleic acid described herein can be removed from a nucleic acid described herein using a suitable method (e.g., by increasing salt concentration, denaturing, washing, adding a suitable solvent and/or salt, adding a suitable competitor, and/or by heating).

In some embodiments a distinguishable identifier is a label. In some embodiments a nucleic acid described herein comprises a detectable label, non-limiting examples of which include a radiolabel (e.g., an isotope), a metallic label, a fluorescent label, a chromophore, a chemiluminescent label, an electrochemiluminescent label (e.g., Origen™), aphosphorescent label, a quencher (e.g., a fluorophore quencher), a fluorescence resonance energy transfer (FRET) pair (e.g., donor and acceptor), a dye, a protein (e.g., an enzyme (e.g., alkaline phosphatase and horseradish peroxidase), an antibody, an antigen or part thereof, a linker, a member of a binding pair), an enzyme substrate, a small molecule (e.g., biotin, avidin), a mass tag, quantum dots, nanoparticles, the like or combinations thereof. Any suitable fluorophore or light emitting material can be used as a label. A light emitting label can be detected and/or quantitated by a variety of suitable techniques such as, for example, flow cytometry, gel electrophoresis, protein-chip analysis (e.g., any chip methodology), microarray, mass spectrometry, cytofluorimetric analysis, fluorescence microscopy, confocal laser scanning microscopy, laser scanning cytometry, the like and combinations thereof.

Binding Pairs

In some embodiments a nucleic acid, or composition described herein comprises one or more binding pairs. In some embodiments a binding pair comprises at least two members (e.g., molecules) that bind non-covalently to (e.g., associate with) each other. Members of a binding pair often bind specifically to each other. Members of a binding pair often bind reversibly to each other, for example where the association of two members of a binding pair can be dissociated by a suitable method. Any suitable binding pair, or members thereof, can be utilized for a composition or method described herein. Non-limiting examples of a binding pair includes antibody/antigen, antibody/antibody, antibody/antibody fragment, antibody/antibody receptor, antibody/protein A or protein G, hapten/anti-hapten, sulfhydryl/maleimide, sulfhydryl/haloacetyl derivative, amine/isotriocyanate, amine/succinimidyl ester, amine/sulfonyl halides, biotin/avidin, biotin/streptavidin, folic acid/folate binding protein, receptor/ligand, vitamin B12/intrinsic factor, analogues thereof, derivatives thereof, binding portions thereof, the like or combinations thereof. Non-limiting examples of a binding pair member include an antibody, antibody fragment, reduced antibody, chemically modified antibody, antibody receptor, an antigen, a hapten, anti-hapten, a peptide, protein, nucleic acid (e.g., double-stranded DNA (dsDNA), single-stranded DNA (ssDNA), or RNA), a nucleotide, a nucleotide analog or derivative (e.g., bromodeoxyuridine (BrdU)), an alkyl moiety (e.g., methyl moiety on methylated DNA or methylated histone), an alkanoyl moiety (e.g., an acetyl group of an acetylated protein (e.g., an acetylated histone)), an alkanoic acid or alkanoate moiety (e.g., a fatty acid), a glyceryl moiety (e.g., a lipid), a phosphoryl moiety, a glycosyl moiety, a ubiquitin moiety, lectin, aptamer, receptor, ligand, metal ion, avidin, neutravidin, biotin, B12, intrinsic factor, analogues thereof, derivatives thereof, binding portions thereof, the like or combinations thereof. In some embodiments, a member of a binding pair comprises a distinguishable identifier.

In some embodiments the nucleic acids, compositions, formulations, combination products and materials described herein can be included as part of kits, which kits can include one or more of pharmaceutical compositions, nucleic acids, and formulations of the same, combination drugs and products and other materials described herein. In some embodiments the products, compositions, kits, formulations, etc. can come in an amount, package, product format with enough medication to treat a patient for 1 day to 1 year, 1 day to 180 days, 1 day to 120 days, 1 day to 90 days, 1 day to 60 days, 1 day to 30 days, or any day or number of days there between, 1-3 months, 1-2 months, about 3 months, about 2 months, about one month, 3-4 weeks, 3-2 weeks, about 4 weeks, about 3 weeks, about 2 weeks, about 1 week, 1-4 hours, 1-12 hours, or 1-24 hours.

In some embodiments, a kit comprises one or more species-specific ANAGO, such as human ANAGO.

In some embodiments, a kit comprises one or more species-specific ANAGO, such as human ANAGO, and one or more nucleic acid donors.

In some embodiments, a kit comprises one or more species-specific ANAGO, one or more nucleic acid donors, one or more NLS, one or more TAG described herein, or one or more compositions thereof. In some embodiments, a kit comprises one or more human ANAGO, one or more nucleic acid donors, one or more NLS, one or more TAG described herein, or one or more compositions thereof. In some embodiments, a kit comprises one or more human ANAGO encoded with nucleic acid sequence of SEQ ID NO:1, SEQ ID NO:2, SEQ ID NO:3, or SEQ ID NO:4, one or more nucleic acid donors, one or more NLS, one or more TAG described herein, or one or more compositions thereof. In some embodiments, a kit comprises one or more human ANAGO encoded with nucleic acid sequence of SEQ ID NO:1, one or more nucleic acid donors, one or more NLS, one or more TAG described herein, or one or more compositions thereof. In some embodiments, a kit comprises one or more human ANAGO encoded with nucleic acid sequence of SEQ ID NO:2, one or more nucleic acid donors, one or more NLS, one or more TAG described herein, or one or more compositions thereof. In some embodiments, a kit comprises one or more human ANAGO encoded with nucleic acid sequence of SEQ ID NO:3, one or more nucleic acid donors, one or more NLS, one or more TAG described herein, or one or more compositions thereof. In some embodiments, a kit comprises one or more human ANAGO encoded with nucleic acid sequence of SEQ ID NO:4, one or more nucleic acid donors, one or more NLS, one or more TAG described herein, or one or more compositions thereof.

In some embodiments, the kits described herein are used in genome editing in eukaryotic cells. Such a gene editing is for gene therapy in the treatment of disease or conditions.

Some embodiments include kits including pharmaceutical compositions described herein, combination compositions and pharmaceutical formulations thereof, packaged into suitable packaging material. A kit optionally includes a label or packaging insert, or any form of written material, in print or electronic media, including a description of any ANAGO, composition, formulation, or method described herein, or any combination thereof.

Vehicles for Delivery

The ANAGO described herein is small enough that it can be introduced into eukaryotic cells via numerous mechanisms and tools, and examples of which, but not limited to, are shown below. An ANAGO can be delivered into a mammalian cell directly in a complete protein form or in a form of nucleic acid after the ANAGO is cloned to an expression vector, such as a mammalian expression vector.

(i) Viral Vector

ANAGO in a form of DNA or RNA can be housed in the capsid of a virus that is known to successfully, or preferentially, or selectively infect a specific cell type under ordinary or laboratory conditions. Injection of the ANAGO-loaded viral particles leads to infection of the target cells and injection of the desired ANAGO into the host cell. The translational machinery and ribosomes proceed to translate the ANAGO into functional argonaute proteins ready for gene-editing. As the virus spreads, more cells become infected and the quantity of argonaute protein produced increases proportionally. The argonaute complex produced can proceed to execute the pre-programmed gene-editing process it was designed for in the target tissues or cells in an organism. This is a preferred method for non-clinical settings, research settings, and for large quantities of cells in vivo or in vitro.

(ii) Electroporation

Target cells are placed in a dish or plate for in vitro exposure to the ANAGO in a form of RNA. Electric pulses are sent through the plate in order to render the membranes of the target cell porous. ANAGO of interest can flow through these pores into the target cells and reach the translational machinery. The ANAGO and donor nucleic acid are then assembled and ready for editing.

(iii) Lipofection

Nucleic acids can be packaged in spherical molecules composed of lipids. These lipids can fuse with lipophilic cellular membranes and dump the nucleic acid payload into the cell. The component parts can then be assembled into the ANAGO for genome editing.

(iv) Nucleofection

A variation of many electroporation protocols used to allow nucleic acids to reach the nucleus, can be used to transport ANAGO into the cell/nucleus for transcription and/or translation into the ultimate active protein product.

(v) Nanoparticle

New formulations of nanoparticles are constantly being developed that can deliver payloads such as the ANAGO into a cell/nucleus. Colloidal gold nanoparticles for example can be used for this purpose safely and efficiently.

(vi) Microinjection

In larger cell types, direct injection of the ANAGO is possible. This method can be used when only a few cells are targeted.

Some of the embodiments contemplated by the inventors are listed below:

Embodiment 1

A synthetic nucleic acid comprising:
a first nucleic acid sequence comprising about 1000 or more contiguous nucleotides, or portion thereof,
wherein the first nucleic acid sequence encodes an ANAGO that is a polypeptide, capable of editing a target nucleic acid sequence within a eukaryotic cell, wherein the ANAGO is a species-specific to the eukaryote;
wherein the first nucleic acid sequence is modified from a second nucleic acid sequence of a microbial species, and wherein the second nucleic acid sequence comprises a coding region that is capable of encoding a microbial Argonaute protein that has endonuclease activities in a microbial cell; and
wherein the first nucleic acid sequence is modified so that the microbial preferred codons of the second nucleic acid sequence are replaced with codons that have preferential usage in the target eukaryotic species.

Embodiment 2

The synthetic nucleic acid of embodiment 1, wherein the ANAGO is a human ANAGO, an animal ANAGO, or a plant ANAGO.

Embodiment 3

The synthetic nucleic acid of embodiment 1, wherein the first nucleic acid sequence comprises at least 70% identity to the nucleic acid sequence of SEQ ID NO:1; SEQ ID NO:2; SEQ ID NO:3, or SEQ ID NO:4, or portion thereof, and wherein the ANAGO is a human ANAGO.

Embodiment 4

The synthetic nucleic acid of embodiment 1, wherein the first nucleic acid sequence comprises the nucleic acid sequence of SEQ ID NO:2.

Embodiment 5

The synthetic nucleic acid of embodiment 1, wherein the first nucleic acid sequence comprises the nucleic acid sequence of SEQ ID NO:3.

Embodiment 6

The synthetic nucleic acid of embodiment 1, wherein the first nucleic acid sequence comprises the nucleic acid sequence of SEQ ID NO:4.

Embodiment 7

The synthetic nucleic acid of any one of embodiments 1 to 6, further comprising a promoter operably linked to the coding region.

Embodiment 8

The synthetic nucleic acid of any one of embodiments 1 to 7, wherein the ANAGO is further attached to a coding sequence of a nuclear localization signal peptide (NLS).

Embodiment 9

A composition comprising the synthetic nucleic acid or the ANAGO of any one of embodiments 1 to 8.

Embodiment 10

The composition of embodiment 9, further comprising a donor nucleic acid comprising:
(i) a desired nucleic acid sequence;
(ii) a 5'-flanking sequence; and
(iii) a 3'-flanking sequence,
wherein each of the 5'-flanking sequence and the 3'-flanking sequence independently comprise at least 10 consecutive nucleotides that are at least 90% identical to a target sequence located in the genome of a eukaryotic cell.

Embodiment 11

The composition of any one of embodiments 9 to 10, wherein the synthetic nucleic acid, and the donor nucleic acid are separate nucleic acid fragments.

Embodiment 12

The composition of any one of embodiments 9 to 11, wherein the synthetic nucleic acid, and the donor nucleic acid are linked via a spacer sequence.

Embodiment 13

The composition of any one of embodiments 9 to 12, wherein the composition is a pharmaceutical composition comprising a pharmaceutical acceptable excipient.

Embodiment 14

A kit comprising the synthetic nucleic acid of any one of embodiments 1 to 8, or the composition of any one of embodiments 9 to 13, or the ANAGO of any one of the embodiments 1-13, or a combination thereof.

Embodiment 15

A method of editing a genome of a eukaryotic cell comprising:
introducing into the cell
(i) a species-specific ANAGO encoded by the first synthetic nucleic acid sequence of any one of embodiments 1 to 14, or an in vitro messenger RNA transcribed by the first synthetic nucleic acid sequence of any one of embodiments 1 to 14; and
(ii) a donor nucleic acid comprising:
a desired nucleic acid sequence,
a 5'-flanking sequence, and
a 3'-flanking sequence,
wherein each of the 5'-flanking sequence and the 3'-flanking sequence are located on opposite sides of the desired nucleic acid sequence and independently comprise at least 10 consecutive nucleotides that are at least 90% identical to a target sequence located in the genome of the eukaryotic cell.

Embodiment 16

The method of embodiment 15, wherein the eukaryotic cell is a human cell, an animal cell, or a plant cell.

Embodiment 17

The method of embodiment 15 or 16, wherein the eukaryotic cell is a human cell.

Embodiment 18

The method of embodiment 17, wherein the first synthetic nucleic acid sequence comprises at least 70% identity to the nucleic acid sequence of SEQ ID NO:1, SEQ ID NO:2, SEQ ID NO:3, or SEQ ID NO:4, or portion thereof, wherein the ANAGO is a human ANAGO.

Embodiment 19

The method of embodiment 17, wherein the first synthetic nucleic acid sequence comprises at least 70% identity to the nucleic acid sequence of SEQ ID NO:2, SEQ ID NO:3, or SEQ ID NO:4, or portion thereof, and wherein the ANAGO is a human ANAGO.

Embodiment 20

The method of embodiment 18 or 19, wherein the human ANAGO in a protein form or the in vitro transcribed messenger RNA is cloned into a mammalian expression vector before being introduced into the human cell.

Embodiment 21

The method of embodiment 20, wherein the expression vector is a plasmid vector, a lentiviral vector, an adeno-associated viral vector, or any viral vector.

Embodiment 22

The method of embodiment 18 or 19, wherein the human ANAGO is stably expressed after being introduced into the genome of a human cell.

Embodiment 23

The method of any one of embodiments 15 to 22, wherein the donor nucleic acid is a single-strand molecule.

Embodiment 24

The method of any one of embodiments 15 to 22, wherein the donor nucleic acid is a double-strand molecule.

Embodiment 25

The method of any one of embodiments 15 to 24, wherein the 5'-flanking sequence and the 3'-flanking sequence contain 10 to 50 nucleotides in length.

Embodiment 26

The method of any one of embodiments 15 to 24, the 5'-flanking sequence and the 3'-flanking sequence have 20 to 30 nucleotides in length.

Embodiment 27

The method of any one of embodiments 15 to 26, wherein each of the 5'-flanking sequence and the 3'-flanking sequence comprise at least 10 nucleotides that are identical to the target sequence.

Embodiment 28

The method of any one of embodiments 15 to 27, wherein the 5' and the 3' flanking sequences are different.

Embodiment 29

The method of any one of embodiments 15 to 28, wherein the target sequence contains 1 or more nucleotides in length.

Embodiment 30

The method of embodiment 15, wherein the ANAGO is cloned into a eukaryotic expression vector before the ANAGO is introduced into the cell.

Embodiment 31

The method of embodiment 15, wherein the desired nucleic acid sequence of the donor nucleic acid comprises a human gene or portion thereof.

Embodiment 32

The method of any one of embodiments 15 to 31, wherein the target sequence is modified.

Embodiment 33

The method of embodiment 32, wherein the modification comprises a deletion, an insertion, replacement of one or more nucleotides, or a combination thereof.

Embodiment 34

The method of embodiment 33, wherein the modification comprises a single nucleotide deletion, a single nucleotide insertion, or a single nucleotide replacement.

Embodiment 35

The method of any one of embodiments 15 to 34, wherein the editing of the genome of the eukaryotic cell occurs in a homologous sequence-dependent manner.

Embodiment 36

The method of any one of embodiments 15 to 34, wherein the eukaryotic cell is a human cell, and wherein the editing of the genome of the human cell occurs in a homologous sequence-dependent manner.

Embodiment 37

The method of any one of embodiments 15 to 36, wherein the ANAGO is introduced into the cell via viral vector, electroporation, lipofection, nucleofection, nanoparticle, or microinjection.

Embodiment 38

The method of any one of embodiments 15 to 37, wherein a single or multiple donor molecules targeting different sites are introduced into a eukaryotic cell at same time for multiplex genome editing at same time.

Embodiment 39

The synthetic nucleic acid or the ANAGO of any one of embodiments 1 to 8, the compositions of any one of embodiments 9 to 13, or the kit of embodiment 14 for use in gene therapy or genome editing.

Embodiment 40

A method of treating a disease, a disorder, or a condition treatable with genome editing in eukaryotic cells comprising, introducing an ANAGO of any one of embodiment 1-38 to a eukaryotic cell.

Embodiment 41

The method of embodiment 40, wherein genome editing in eukaryotic cells is for chronic myelogenous leukemia; lowering LDL levels in blood stream; or enhancing the effectiveness of immune therapy against tumor cells.

EXAMPLES

A. Construction of Human ANAGO

The ability to introduce a nucleic acid (e.g., a gene, heterologous DNA or modified nucleic acid) into a genome of an organism at a specific targeted locus is a powerful tool for therapeutic and research purposes. The user-friendly CRISPR-Cas9 is very efficient in making mutations via non-homologous end joining (NHEJ) in human cancer cell lines such as 293T cells. However, it can mediate homologous recombination (HR) only at a much low efficiency (2-5%) in 293T cells and even lower in other biologically relevant cells such as human induced pluripotent stem cells (iPSCs). Gao et al. in a retracted publication (Gao F, et al., (2016) Nat. Biotechnol. 34(7):768-73) reported that it is feasible to achieve genome editing in human cells by using *Natronobacterium gregoryi* Argonaute (NgAgo) with a guide DNA oligo. However, multiple labs have failed to reproduce this phenomenon claimed by Gao et al. thus far, which led to the withdrawal of this publication later by Gao et al. Gao et al. use the sequence of the NgAgo in their publication.

To investigate whether the ANAGO described herein could be used as a novel and practical gene editing tool in mammalian cells, we reasoned that it is plausible for microbial argonaute proteins to mediate gene editing in human cells, but at a very low efficiency to be detectable. Particularly, since most of reported DNA targeting argonaute proteins are the products of either bacterial or archaeal microorganisms, their preference of codon usage is significantly different from the ones used in the translation machinery of human cells. It is known that codon usage is a rate-limiting factor for efficient translation and proper folding of a protein in an organism-specific manner. Therefore, we reengineered and adapted the DNA coding sequences of microbial argonaute proteins that have DNA endonuclease activities in microbial cells, such as NgAgo, PfAgo, TtAgo and MjAgo, with the codons that are most frequently used in human cells (as described above), to generate humanized argonaute variants, that comprises, conserves, and/or retains an ability to edit a target nucleic acid sequence within a human cell when expressed in the human cell. We name this type of reengineered and adapted argonaute variant "ANAGO". ANAGO is species-specific. When ANAGO comprises the codons that are preferentially used in human cells, we call it human ANAGO.

In order to introduce the ANAGO into the nucleus of mammalian cells, we fused a SV40 nuclear localization signal peptide sequence (NLS) to the N-terminus of the protein in ANAGO. A small Human influenza hemagglutinin (HA) tag was also included for protein detection purposes. The DNA coding sequences of the human ANAGO, attached to a NLS and a HA tag and derived from (a) NgAgo, (b) PfAgo, (c) TtAgo, and (d) MjAgo, are shown below, wherein the HA epitope tag sequence is framed; and the SV40 nuclear localization signal (NLS) sequence is underlined.

(a) Nucleic Acid Sequence of SEQ ID NO: 1 - DNA sequence of a human ANAGO of NLS-NgAgo ORF
ATGGTGCCAAAAAAGAAGAGAAAGGTAGCCACCGTGATCGACCTGGACTCCACCACCACCGCCGACG

AGCTGACCTCCGGCCACACCTACGACATCTCCGTGACCCTGACCGGCGTGTACGACAACACCGACGAGC

AGCACCCCCGGATGTCCCTGGCCTTCGAGCAGGACAACGGCGAGCGGCGGTACATCACCCTGTGGAAG

AACACCACCCCCAAGGACGTGTTCACCTACGACTACGCCACCGGCTCCACCTACATCTTCACCAACATCG

ACTACGAGGTGAAGGACGGCTACGAGAACCTGACCGCCACCTACCAGACCACCGTGGAGAACGCCACC

GCCCAGGAGGTGGGCACCACCGACGAGGACGAGACCTTCGCCGGCGGCGAGCCCCTGGACCACCACCT

GGACGACGCCCTGAACGAGACCCCCGACGACGCCGAGACCGAGTCCGACTCCGGCCACGTGATGACCT

CCTTCGCCTCCCGGGACCAGCTGCCCGAGTGGACCCTGCACACCTACACCCTGACCGCCACCGACGGCG

CCAAGACCGACACCGAGTACGCCCGGCGGACCCTGGCCTACACCGTGCGGCAGGAGCTGTACACCGAC

CACGACGCCGCCCCCGTGGCCACCGACGGCCTGATGCTGCTGACCCCCGAGCCCCTGGGCGAGACCCCC

CTGGACCTGGACTGCGGCGTGCGGGTGGAGGCCGACGAGACCCGGACCCTGGACTACACCACCGCCAA

GGACCGGCTGCTGGCCCGGGAGCTGGTGGAGGAGGGCCTGAAGCGGTCCCTGTGGGACGACTACCTG

GTGCGGGGCATCGACGAGGTGCTGTCCAAGGAGCCCGTGCTGACCTGCGACGAGTTCGACCTGCACGA

GCGGTACGACCTGTCCGTGGAGGTGGGCCACTCCGGCCGGGCCTACCTGCACATCAACTTCCGGCACCG

GTTCGTGCCCAAGCTGACCCTGGCCGACATCGACGACGACAACATCTACCCCGGCCTGCGGGTGAAGAC

CACCTACCGGCCCCGGCGGGGCCACATCGTGTGGGGCCTGCGGGACGAGTGCGCCACCGACTCCCTGA

ACACCCTGGGCAACCAGTCCGTGGTGGCCTACCACCGGAACAACCAGACCCCCATCAACACCGACCTGC

TGGACGCCATCGAGGCCGCCGACCGGCGGGTGGTGGAGACCCGGCGGCAGGGCCACGGCGACGACGC

CGTGTCCTTCCCCCAGGAGCTGCTGGCCGTGGAGCCCAACACCCACCAGATCAAGCAGTTCGCCTCCGA

CGGCTTCCACCAGCAGGCCCGGTCCAAGACCCGGCTGTCCGCCTCCCGGTGCTCCGAGAAGGCCCAGGC

CTTCGCCGAGCGGCTGGACCCCGTGCGGCTGAACGGCTCCACCGTGGAGTTCTCCTCCGAGTTCTTCACC

GGCAACAACGAGCAGCAGCTGCGGCTGCTGTACGAGAACGGCGAGTCCGTGCTGACCTTCCGGGACGG

CGCCCGGGGCGCCCACCCCGACGAGACCTTCTCCAAGGGCATCGTGAACCCCCCCGAGTCCTTCGAGGT

GGCCGTGGTGCTGCCCGAGCAGCAGGCCGACACCTGCAAGGCCCAGTGGGACACCATGGCCGACCTGC

TGAACCAGGCCGGCGCCCCCCCCACCCGGTCCGAGACCGTGCAGTACGACGCCTTCTCCTCCCCCGAGT

CCATCTCCCTGAACGTGGCCGGCGCCATCGACCCCTCCGAGGTGGACGCCGCCTTCGTGGTGCTGCCCC

CCGACCAGGAGGGCTTCGCCGACCTGGCCTCCCCCACCGAGACCTACGACGAGCTGAAGAAGGCCCTG

GCCAACATGGGCATCTACTCCCAGATGGCCTACTTCGACCGGTTCCGGGACGCCAAGATCTTCTACACCC

GGAACGTGGCCCTGGGCCTGCTGGCCGCCGCCGGCGGCGTGGCCTTCACCACCGAGCACGCCATGCCC

GGCGACGCCGACATGTTCATCGGCATCGACGTGTCCCGGTCCTACCCCGAGGACGGCGCCTCCGGCCAG

ATCAACATCGCCGCCACCGCCACCGCCGTGTACAAGGACGGCACCATCCTGGGCCACTCCTCCACCCGG

CCCCAGCTGGGCGAGAAGCTGCAGTCCACCGACGTGCGGGACATCATGAAGAACGCCATCCTGGGCTA

CCAGCAGGTGACCGGCGAGTCCCCCACCCACATCGTGATCCACCGGGACGGCTTCATGAACGAGGACCT

GGACCCCGCCACCGAGTTCCTGAACGAGCAGGGCGTGGAGTACGACATCGTGGAGATCCGGAAGCAGC

CCCAGACCCGGCTGCTGGCCGTGTCCGACGTGCAGTACGACACCCCCGTGAAGTCCATCGCCGCCATCA

ACCAGAACGAGCCCCGGGCCACCGTGGCCACCTTCGGCGCCCCCGAGTACCTGGCCACCCGGGACGGC

GGCGGCCTGCCCCGGCCCATCCAGATCGAGCGGGTGGCCGGCGAGACCGACATCGAGACCCTGACCCG

GCAGGTGTACCTGCTGTCCCAGTCCCACATCCAGGTGCACAACTCCACCGCCCGGCTGCCCATCACCACC

GCCTACGCCGACCAGGCCTCCACCCACGCCACCAAGGGCTACCTGGTGCAGACCGGCGCCTTCGAGTCC

AACGTGGGCTTCCTG (b) Nucleic Acid Sequence of SEQ ID NO: 2 - DNA sequence of a human ANAGO of HA-NLS-PfAgo ORF

ATGGTCTACCCCTACGACGTGCCCGACTACGCCCCAAAAAAGAAGAGAAAGGTAGCCAAGGCCAAGG

TGGTGATCAACCTGGTGAAGATCAACAAGAAGATCATCCCCGACAAGATCTACGTGTACAGACTGTTCA

ACGACCCCGAGGAGGAGCTGCAGAAGGAGGGCTACAGCATCTACAGACTGGCCTACGAGAACGTGGG

CATCGTGATCGACCCCGAGAACCTGATCATCGCCACCACCAAGGAGCTGGAGTACGAGGGCGAGTTCAT

CCCCGAGGGCGAGATCAGCTTCAGCGAGCTGAGAAACGACTACCAGAGCAAGCTGGTGCTGAGACTGC

TGAAGGAGAACGGCATCGGCGAGTACGAGCTGAGCAAGCTGCTGAGAAAGTTCAGAAAGCCCAAGAC

CTTCGGCGACTACAAGGTGATCCCCAGCGTGGAGATGAGCGTGATCAAGCACGACGAGGACTTCTACCT

GGTGATCCACATCATCCACCAGATCCAGAGCATGAAGACCCTGTGGGAGCTGGTGAACAAGGACCCCA

AGGAGCTGGAGGAGTTCCTGATGACCCACAAGGAGAACCTGATGCTGAAGGACATCGCCAGCCCCCTG

AAGACCGTGTACAAGCCCTGCTTCGAGGAGTACACCAAGAAGCCCAAGCTGGACCACAACCAGGAGAT

CGTGAAGTACTGGTACAACTACCACATCGAGAGATACTGGAACACCCCCGAGGCCAAGCTGGAGTTCTA

CAGAAAGTTCGGCCAGGTGGACCTGAAGCAGCCCGCCATCCTGGCCAAGTTCGCCAGCAAGATCAAGA

AGAACAAGAACTACAAGATCTACCTGCTGCCCCAGCTGGTGGTGCCCACCTACAACGCCGAGCAGCTGG

AGAGCGACGTGGCCAAGGAGATCCTGGAGTACACCAAGCTGATGCCCGAGGAGAGAAAGGAGCTGCT

GGAGAACATCCTGGCCGAGGTGGACAGCGACATCATCGACAAGAGCCTGAGCGAGATCGAGGTGGAG

AAGATCGCCCAGGAGCTGGAGAACAAGATCAGAGTGAGAGACGACAAGGGCAACAGCGTGCCCATCA

GCCAGCTGAACGTGCAGAAGAGCCAGCTGCTGCTGTGGACCAACTACAGCAGAAAGTACCCCGTGATC

CTGCCCTACGAGGTGCCCGAGAAGTTCAGAAAGATCAGAGAGATCCCCATGTTCATCATCCTGGACAGC

GGCCTGCTGGCCGACATCCAGAACTTCGCCACCAACGAGTTCAGAGAGCTGGTGAAGAGCATGTACTAC

AGCCTGGCCAAGAAGTACAACAGCCTGGCCAAGAAGGCCAGAAGCACCAACGAGATCGGCCTGCCCTT

CCTGGACTTCAGAGGCAAGGAGAAGGTGATCACCGAGGACCTGAACAGCGACAAGGGCATCATCGAG

GTGGTGGAGCAGGTGACAGCTTCATGAAGGGCAAGGAGCTGGGCCTGGCCTTCATCGCCGCCAGAAA

CAAGCTGAGCAGCGAGAAGTTCGAGGAGATCAAGAGAAGACTGTTCAACCTGAACGTGATCAGCCAGG

TGGTGAACGAGGACACCCTGAAGAACAAGAGAGACAAGTACGACAGAAACAGACTGGACCTGTTCGTG

AGACACAACCTGCTGTTCCAGGTGCTGAGCAAGCTGGGCGTGAAGTACTACGTGCTGGACTACAGATTC

AACTACGACTACATCATCGGCATCGACGTGGCCCCCATGAAGAGAAGCGAGGGCTACATCGGCGGCAG

CGCCGTGATGTTCGACAGCCAGGGCTACATCAGAAAGATCGTGCCCATCAAGATCGGCGAGCAGAGAG

GCGAGAGCGTGGACATGAACGAGTTCTTCAAGGAGATGGTGGACAAGTTCAAGGAGTTCAACATCAAG

CTGGACAACAAGAAGATCCTGCTGCTGAGAGACGGCAGAATCACCAACAACGAGGAGGAGGGCCTGA

AGTACATCAGCGAGATGTTCGACATCGAGGTGGTGACCATGGACGTGATCAAGAACCACCCCGTGAGA

GCCTTCGCCAACATGAAGATGTACTTCAACCTGGGCGGCGCCATCTACCTGATCCCCCACAAGCTGAAGC

AGGCCAAGGGCACCCCCATCCCCATCAAGCTGGCCAAGAAGAGAATCATCAAGAACGGCAAGGTGGAG

AAGCAGAGCATCACCAGACAGGACGTGCTGGACATCTTCATCCTGACCAGACTGAACTACGGCAGCATC

AGCGCCGACATGAGACTGCCCGCCCCCGTGCACTACGCCCACAAGTTCGCCAACGCCATCAGAAACGAG

TGGAAGATCAAGGAGGAGTTCCTGGCCGAGGGCTTCCTGTACTTCGTG (c) Nucleic Acid Sequence of SEQ ID NO: 3 - DNA sequence of a human
ANAGO of HA-NLS-TtAgo ORF

ATGGTCTACCCCTACGACGTGCCCGACTACGCCCCTAAGAAAAAGCGGAAGGTGGCCAACCACCTGGG

CAAGACAGAGGTGTTCCTGAACAGATTCGCCCTGCGGCCTCTGAACCCTGAGGAACTCAGACCTTGGCG

GCTGGAAGTGGTGCTGGATCCTCCACCTGGACGCGAGGAAGTGTATCCTCTGCTGGCTCAAGTGGCTCG

GAGAGCTGGCGGAGTGACAGTTAGAATGGGAGATGGCCTGGCCAGCTGGTCCCCACCTGAAGTTCTTG

TGCTGGAAGGCACCCTGGCCAGAATGGGCCAGACATACGCCTACCGGCTGTACCCCAAAGGCAGAAGG

CCTCTGGATCCCAAGGATCCCGGCGAGAGATCTGTGCTGTCTGCCCTGGCTAGACGGCTGCTGCAAGAG

AGACTGAGAAGGCTCGAAGGCGTGTGGGTGGAAGGACTGGCCGTGTACAGAAGAGAGCACGCCAGAG

GACCTGGCTGGCGAGTTCTTGGCGGAGCTGTTCTGGATCTGTGGGTGTCAGATAGCGGCGCCTTTCTGC

TGGAAGTCGACCCCGCCTATAGAATCCTGTGCGAGATGAGCCTGGAAGCTTGGCTGGCTCAGGGACAC

CCTCTGCCTAAAAGAGTGCGGAACGCCTACGACAGACGGACCTGGGAACTGCTGAGACTGGGCGAAGA

GGACCCCAAAGAACTTCCTCTGCCTGGCGGACTGAGCCTGCTGGATTACCACGCCTCTAAGGGCAGACT

GCAGGGCAGAGAAGGTGGAAGAGTGGCCTGGGTTGCCGATCCTAAGGACCCCAGAAAGCCCATTCCTC

ACCTGACAGGACTGCTGGTGCCTGTGCTGACCCTGGAAGATCTGCACGAGGAAGAGGGATCTCTGGCC

CTGTCTCTGCCTTGGGAAGAGAGAAGAAGGCGGACCAGAGAGATCGCCAGCTGGATCGGAAGAAGGC

TTGGCCTGGGAACACCTGAGGCTGTTAGAGCCCAGGCCTACAGACTGAGCATCCCCAAGCTGATGGGCC

GCAGAGCCGTGTCTAAACCTGCCGATGCTCTGAGAGTGGGCTTCTACAGAGCCCAAGAGACAGCCCTG

GCTCTGCTCAGACTTGATGGCGCTCAAGGCTGGCCCGAGTTTCTGAGAAGGGCTCTGCTGAGAGCCTTT

GGAGCCTCTGGCGCTTCTCTGAGACTGCACACACTGCACGCCCATCCTTCTCAGGGCCTCGCCTTTAGAG

AGGCTCTGAGAAAGGCCAAAGAAGAGGGCGTTCAGGCCGTGCTGGTTCTGACACCTCCTATGGCATGG

GAAGATCGGAACCGGCTGAAAGCCCTGCTGCTCAGAGAGGGACTGCCTAGCCAGATCCTGAACGTGCC

CCTGAGAGAAGAGGAACGGCACAGATGGGAGAATGCCCTGCTGGGCCTGCTGGCCAAAGCTGGACTTC

AAGTGGTTGCCCTGTCCGGCGCCTATCCTGCTGAACTGGCTGTGGGATTTGACGCTGGCGGCAGAGAGA

GCTTCAGATTTGGAGGCGCTGCTTGTGCCGTTGGCGGAGATGGTGGACATCTGCTGTGGACACTGCCTG

AAGCTCAGGCCGGCGAAAGAATCCCTCAAGAGGTCGTGTGGGACCTGCTCGAAGAAACCCTGTGGGCC

TTCAGAAGAAAGGCCGGCAGGCTGCCTTCAAGAGTGCTGCTCCTGAGAGATGGCAGAGTGCCCCAGGA

TGAGTTTGCCCTGGCACTGGAAGCCCTGGCAAGAGAGGGAATTGCCTACGACCTGGTGTCCGTGCGGA

AATCTGGTGGCGGAAGAGTGTACCCCGTGCAAGGCAGACTGGCCGATGGACTGTATGTGCCTCTGGAA

GATAAGACCTTCCTGCTGCTGACCGTGCACCGGGACTTTAGAGGCACACCCAGACCTCTGAAGCTGGTG

CATGAAGCCGGCGACACACCTCTCGAAGCTCTGGCCCACCAGATCTTTCACCTGACCAGACTGTACCCCG

CCAGCGGCTTTGCCTTTCCTAGACTGCCTGCTCCTCTGCACCTGGCCGACAGACTGGTCAAAGAAGTGGG

CCGCCTGGGCATCAGACACCTGAAAGAGGTGGACCGCGAGAAGCTGTTCTTCGTG (d) Nucleic Acid Sequence of SEQ ID NO: 4 - DNA sequence of a human
ANAGO of HA-NLS-MjAgo ORF

ATGGTCTACCCCTACGACGTGCCCGACTACGCCCCTAAGAAAAAGCGGAAGGTGGCCTTTACCATGGT

-continued

```
GCTGAACAAAGTGACCTACAAGATCAACGCCTATAAGATCAAAGAGGAATTCATCCCCAAAGAGGTGCA

CTTCTACCGGATCAAGAGCTTCGTGAACGAGGCCTTCAACTTCTACAGATTCGTGAACTTCTACGGCGGC

ATGATCATCAACAAGAAAGACAAGTCCTTCGTGCTGCCCTACAAGGTGGACAACAAGGTGCTGAAGTAC

AAGGACGGCAACAACGAGATCCCCATCGACATCGAGTACATCAAGAGCCTGAAGCTCGAGTACGTGAA

GCCCGAGATCGCCGAGAAGCTTGTGCGGGGCTATCTGAAGTCCGTGCACAAGATCGAGCCCGAGCTGA

GCCGGATCATCAAGAACATCCGGAAGCACAAGGTGGTGGAAAACATCAAGGTGGAAAGCTACTGCGAG

TACGAAGTGAAGAAGCACGACGGCGACTACTACCTGATCCTGAACTTCAGACACACCGCCAGCATCACC

AAGCACCTGTGGGACTTCGTGAATAGAGACAAGGCCCTGCTGGAAGAGTACGTGGGCAAGAAGATCAT

CTTCAAGCCCAATCCTAAAGTGCGGTACACCATCAGCCTGGTGGACGCCCCAAATCCTCAGAAAATCGA

GGAAATCATGAGCCACATCATCAAGTACTACAAGTGGAGCGAGGACATGGTCAAGAGCACCTTCGGCG

AGATCGACTACAACCAGCCTATCATGTACTGCGAGGAAATTCTGGAACCCTTCGCACCCCAGTTCTGCAA

CCTGGTGTTCTACATGGACGAGCTGGACAGCTACATCCTGAAAGAGCTGCAGAGCTACTGGCGGCTGA

GCAACGAGAACAAGGGCAAGATCATTAACGAGATTGCCAAGAAACTGCGGTTCATCGACAACACGCCC

AAAGAACTGGAATTCATGAAGTTCAACAACACCCCGCTGCTGGTCAAGGACGTGAACAAGAACCCCACC

AAGATCTACAGCACCAACACACTGTTCACCTGGATCTACAATCAGAACGCCAAAATCTACCTGCCTTACG

ACGTCCCCGAGATCATCCGGAACAAGAATCTGCTGACCTACATCCTCATCGACGAAGAGATCAAGGATG

AGCTGAAGGCCATCAAGGACAAAGTCAACAAGATGTTCCGCAACTACAACAAGATCGCCAACAAGACC

GAGCTGCCCAAGTTCAACTACGCCAACCGGTGGAAGTACTTTAGCACCGACGACATCCGGGGCATCATC

AAAGAGATTAAGAGCGAGTTCAACGACGAGATCTGCTTCGCCCTGATCATCGGCAAAGAGAAGTATAA

GGACAACGATTACTACGAGATCCTCAAGAAGCAGCTGTTCGACCTGAAGATTATCAGCCAGAACATCCT

GTGGGAGAACTGGCGGAAGGACGACAAGGGCTACATGACCAACAACCTGCTGATCCAGATCATGGGCA

AGCTGGGCATCAAGTATTTCATCCTGGACAGCAAGACCCCGTACGACTACATCATGGGCCTCGATACAG

GCCTGGGCATCTTCGGCAATCACAGAGTCGGCGGCTGTACCGTGGTGTACGATAGCGAGGGAAAGATC

CGGCGGATCCAGCCAATCGAGACACCAGCTCCAGGCGAGAGACTGCATCTGCCCTACGTGATCGAGTAC

CTGGAAAACAAGGCCAACATCGACATGGAAAACAAAAACATCCTGTTCCTCCGCGACGGCTTCATCCAG

AACAGCGAGCGGAACGATCTGAAAGAGATCAGCAAAGAGCTGAACAGCAATATCGAAGTGATCTCTAT

TCGGAAGAACAACAAGTACAAAGTGTTCACCAGCGACTACAGGATCGGCAGCGTGTTCGGCAACGACG

GCATCTTCCTGCCTCACAAGACCCCTTTCGGCAGCAACCCTGTGAAGCTGAGCACCTGGCTGAGATTCAA

CTGCGGCAACGAGGAAGGCCTGAAAATCAACGAGAGCATCATGCAGCTGCTGTACGATCTGACCAAGA

TGAACTACAGCGCCCTGTACGGCGAGGGCAGATACCTGAGAATCCCCGCTCCTATCCACTACGCCGACA

AGTTCGTGAAGGCCCTGGGCAAAAACTGGAAGATCGACGAGGAACTGCTGAAGCACGGCTTTCTGTAC

TTCATC
```

B. ANAGO Induced Homologous Recombination Directed Genome Editing in Eukaryotes

Materials and Methods

Constructs of ANAGO expression cassette: The ANAGO encoded with the humanized DNA sequence of NLS-NgAgo ORF, or HA-NLS-PfAgo ORF, or HA-NLS-TtAgo ORF, or HA-NLS-MjAgo ORF was chemically synthesized and fused to the P2A-YFP cDNA cassette. The expression of fusion open reading frame was driven by EF1alpha promoter in a mammalian expression vector (SynBio Tech, New Jersey).

Cell culture and transfection. HEK293 (ATCC catalog # CRL-1573) cells were maintained in a DMEM high glucose medium supplemented with 10% fetal bovine serum and 100 U/ml penicillin and 100 ug/ml streptomycin. Cells were seeded into 12-well plates one day before transfection. Cells were transfected at about 50% confluence using LIPOFECTAMINE™ 3000 (Thermo Scientific). Specifically, HEK293 were transfected with 1000 ng of a human ANAGO-expressing plasmid plus certain amount of donor DNA fragment that is dependent on its size (for examples, 240 ng of 1.8 kb PCSK9-mCherry knock-in fragment or 200 nM of single-stranded oligonucleotide PCSK9 R104C-V114A 70mer for PCSK9 gene in example 1, see FIG. 1a). Cells were harvested for genomic DNA extraction 72 hours post transfection. The donor fragment directed genomic editing event was identified and confirmed by PCR. Subsequently, the genomic PCR products are sequenced and analyzed.

We have used a few human ANAGO described herein to induce homologous recombination directed genome editing in human cells successfully. We have discovered that the use of the human ANAGO to induce genome editing in human cells does not require the presence of a guide DNA molecule. ANAGO induced genome editing is highly precise and produces very low numbers of associated indel events in the target site in all cases tested. Selected examples of using an ANAGO-induced sequence editing (AISE) technology to modify genes in human cells are shown below.

Example 1. Human PCSK9

Proprotein convertase subtilisin/kexin type9 (PCSK9), acts in lipoprotein homeostasis. It binds and removes low-density lipoprotein receptors (LDLR). If not binding PCSK9, LDLR will return to the cell surface and can continue to remove LDL-particles from the bloodstream. Agents which block PCSK9 can lower LDL particle concentrations. Significantly, individuals with complete naturally occurring heterozygous loss-of-function (LOF) mutations of PCSK9 gene have a near 88% reduced risk of developing cardiovascular complications over a 15-year follow-up period [Cohen J C, Boerwinkle E, et al, 2006, NEJM 354:1264-1272]. Moreover, carriers of LOF mutations such as deltaR97+Y142X, C679X, and R104C+V114A were found to lack PCSK9 expression. These individuals with natural occurring LOF mutations have very low LDL levels in their blood stream without association with any obvious deleterious effects. This supports the clinical utility of introducing LOF mutations to PCSK9 through gene editing to treat hypercholesterolemia.

Figure 1B:
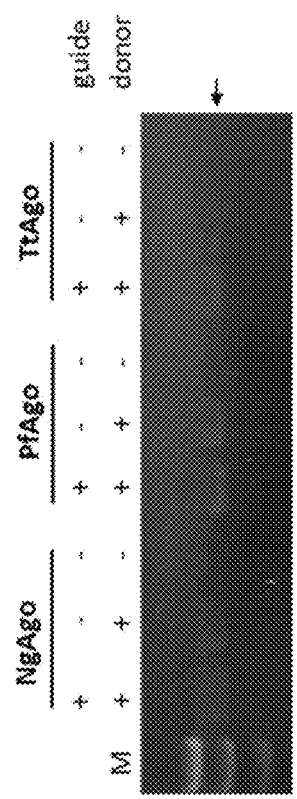
FIG. 1b shows genomic PCR screening to identify mCherry knock-in event.

To test if ANAGO induced sequence editing (AISE) technology described herein could be used to introduce specific PCSK9 LOF mutations in mammalian cells, we first constructed a donor molecule via fusion PCR, which contains the mCherry coding sequence flanked by the homology regions to the exon 1 and intron 1 sequence of PCSK9 gene on the left and right sides respectively. The homology directed replacement (HDR) of the mCherry fragment removes the entire exon 1 as well as 88 bps of the intron 1 sequence of PCSK9 (FIG. 1a). The protein expression constructs of human ANAGO (NLS-NgAgo ORF, HA-NLS-PfAgo ORF, and HA-NLS-TtAgo ORF) and the donor molecule were co-transfected into HEK293 either with or without a guide oligo PCSK9-GD8S (5'-TGGGTC-CCGCGGGCGCCCGTGCGC-3' (SEQ ID NO: 7)) that targets exon 1 by using LIPOFECTAMINE™ 3000. The cellular genomic DNA was harvested at 72 hours post transfection. PCR of genomic DNA samples was carried out to identify the mCherry knock-in event by pairing a donor mCherry specific primer (mCherry-For: 5'-CCTTTCCCA-CAACGAGGACT-3' (SEQ ID NO: 8)) with a flanking region of PCSK9 specific primer (PCSK9-in1-R3: 5'-CGA-GAATACCTCCGCCCTT-3' (SEQ ID NO: 9)), which is located outside of the right homology arm (FIG. 1b). The genomic PCR product was only detectable from the cell samples that were transfected with an ANAGO expression construct and the 1.8 kb of mCherry KI donor fragment either with or without the guide oligo, but not in the absence of the donor fragment (FIG. 1b).

In a separate experimental setting, instead of using an over 500 bps long and double stranded homologous sequence as a flanking arm to facilitate HDR, we tested whether a short and single-stranded oligodeoxynucleotide, PCSK9 R104C-V114A 70mer (5'-CCTGCAGGCCCAGGCTGCC T̄GCCGGGGATACCTCACCAAGATCCTG

CATG C̄CTTCCATGGCCTTCTTCCT-3' (SEQ ID NO: 5)), which mimics R104C (CGC>TGC)+V114A (GTC>GCC) LOF mutant allele sequence of human PCSK9 gene, could be used as a donor template. The mutated bases are located at the 20th and 40th positions of the 70mer respectively. To estimate the relative frequency of sequence exchanging in the transfected cells, a pair of primers (PCSK9 F9: 5'-GCTTTTTGGTCCGCATTTGG-3' (SEQ ID NO: 10) and PCSK9 R9: 5'-GGCTCTACCCCTAGCTGTCT-3' (SEQ ID NO: 11)) located outside of the donor target region was used to generate the genomic PCR product for Sanger sequencing analysis. The results indicated that about 7.1% of genomic PCR products contained the intended R104C+V114A mutation incorporated into the PCSK9 allele in HEK293 cells (FIG. 1c). This result also validates the notion that a short homologous region of 19 bases on each side of modified bases is long enough to generate a desired HDR. In addition, we tested another single-stranded oligo 89mer, PCSK9 Y142X-E144X_donor89_Bgl2

(5'-TCTCTGGCTTCTGCAGGCCTTGAAGTTGCCCCATGTCGACT

AG̱ATCT̄AGGAGGACTCCTCTGTCTTTGCCCAGAGCATCCCGTGGAACC-

3' (SEQ ID NO: 12)), which introduces LOF mutations Y142X (TAC>TAG) and E144X (GAG>TAG) as well as a Bgl2 site (underlined bases) into the exon 3 sequence of PCSK9 gene (FIG. 1a). The Y142X LOF mutation of PCSK9 was found naturally in an African American woman, who has no detectable PCSK9 expression but apparently in good health. Her circulating LDL level is at 0.36 mM, which is about 8-fold lower than normal (Zhao Z, et al., Am J Hum Genet. 2006; 79:514-523). A pair of specific PCR primers (PCSK9 F8 primer 5'-CCGT-GTTGCAGGGATATGGG-3' (SEQ ID NO: 13) and PCSK9 R8 primer 5'-CATTTGTGGGGCAACAGGAAG-3' (SEQ ID NO: 14)) located in the flanking introns were used to generate a 541 bp PCR amplicon for sequencing analysis. In this case, 3% of amplicon were the HDR product, meanwhile, the non-HDR indel incidence was nearly undetectable (FIG. 1d). These studies suggest that AISE technology could be used to specifically inactivate PCSK9 gene and thus to reduce the circulating LDL level in patients with hypercholesterolemia.

Example 2. Human ABL1

The Philadelphia (Ph) translocation t(9;22)(q34;q11) leads ABL1 to fuse with BCR. The resulting BCR-ABL fusion gene is the main reason causing chronic myelogenous leukemia (CML) and Ph+ acute lymphoblastic leukemia (ALL). BCR-ABL encodes a constitutively active cytoplasmic tyrosine kinase that is necessary and sufficient to induce and maintain leukemic transformation. The age-adjusted incidence is 1.6 per 100,000 population members. Small molecular inhibitors have been developed to inhibit BCR-ABL activity. However, drug resistance often occurs in many patients receiving treatment.

Since the main cause of disease is the hyper kinase activity of the fusion protein, an insertion of a premature stop codon in the front of the coding region of kinase domain should result in a truncated product that lacks the kinase domain and thereby inactivates the BCR-ABL fusion gene. A precise gene editing with an AISE approach described herein to inactivate the fusion gene could be done ex vivo with a patient's bone marrow hematopoietic stem cells (HSCs). This approach may cure the disease permanently for CML and Ph+ ALL patients.

BCR-ABLex6stop-H3, a single-stranded oligodeoxy-nucleotides 70mer (5'-GGCAGGGGTCTGCACCCGGGAGCCCCCGTTCTAAGCTTTCACTGAG

TTCATGACCTACGGGAACCTCCTG-3' (SEQ ID NO: 6)), which changed ABL1 residue Tyr312 codon TAT to a stop codon TAA as well as introduced a Hind III site, which was designed and synthesized. The engineered site is flanked by 32 nucleotides of short homology sequence on each side of the 70mer donor oligo (FIG. 2a). To test whether the 70mer of single-stranded oligo harboring 5 altered bases could be used as a donor molecule to introduce the compound stop codon/Hind III site into the precise target site of ABL1 exon 6 of human genome, we co-transfected a human ANAGO expression construct together with the donor oligo BCR-ABLex6stop-H3 70mer into HEK293 cells. The genomic DNA of transfected cells was harvested at 96 hours post transfection. The genomic region containing the target site was amplified by PCR with a pair of specific primers (ABL-F1: 5'-GCGTCTGAATTCTGTGGCAG-3' (SEQ ID NO: 15) and ABL-R1: 5'-CTTTGCCAGGAGCCTAGTGT-3' (SEQ ID NO: 16)) and the PCR products were subsequently sequenced. The result indicated that highly efficient and precise editing was achieved. The on-target integration of donor sequence was detected in 43% of genomic PCR products of the cells transfected with the ANAGO expression construct based on NgAgo, meanwhile the non-HDR indel incidence was less than 1% (FIG. 2b). The integration of TAAGCTT (stop/Hind III) mutation sequence was further confirmed (FIG. 2c). In order to have a comprehensive assessment of editing events, a 429 bp of PCR amplicon of target site was generated by using a pair of primers (ABL-F2: 5'-TTGGGACCATGTTGGAAGTT-3' (SEQ ID NO: 17) and ABL-R2: 5'-AGCACTGAGGTTAGAAGCTG-3' (SEQ ID NO: 18)). The amplicon product was subjected to the Next Generation Sequencing (NGS) (Amplicon-EZ NGS service was provided by GeneWiz, NJ). The total sequence reads were more than 30,000 for each amplicon sample. For the cells transfected with the ANAGO expression construct based on NgAgo, 32.0% of 32,207 sequence reads belong to the precise on-target HDR editing events. In the cells transfected with the other protein expression constructs of the human ANAGO, such as HA-NLS-PfAgo ORF, HA-NLS-TtAgo ORF, and HA-NLS-MjAgo ORF, the percentages of on-target HDR precise editing reads were 23.5%, 19.5% and 10.3% respectively (Table 1). The result also confirmed that the unintended indel events commonly associated with a DNA double-strand break (DSB) were rare, less than 1%.

TABLE 1

Summary of Annplicon Deep Sequencing Results

| ANAGO (originated from) | Target Reads | Precise HDR Reads | HDR (%) | WT Reads | WT (%) |
|---|---|---|---|---|---|
| NgAgo | 32207 | 10306 | 32.0 | 5672 | 18 |
| PfAgo | 37355 | 8774 | 23.5 | 10128 | 27 |
| TtAgo | 40280 | 7867 | 19.5 | 14188 | 35 |
| MjAgo | 43696 | 4512 | 10.3 | 19335 | 44 |

Our data indicates the potential clinical application of the AISE technology disclosed herein for the cure of CML and Ph+ ALL by permanently inactivation of BCR-ABL oncogene in hematopoietic stem cells isolated from these patients.

Example 3. Human Histone 2Bc

Histone 2Bc gene is an intronless and house-keeping gene. It encodes a histone 2B subunit. In this example, we want to expand the potential application of the AISE technology. Particularly, we want to see if a short homologous flanking sequence, for example, as short as 50 bps could be used to facilitate the knock-in of a large exogenous DNA fragment (>700 bp) in mammalian cells. We generated a donor fragment H2Bc-mCherry KI by using mCherry ORF (H2Bc-LH50-mCHer: 5'-ACGCAGTGTCCGAAGGTACCAAGGCTGTC

ACCAAGTATACAAGCTCCAAGATGGTGAGCAAGGGCGAG-3' (SEQ ID

NO: 19); and mCHer-H2Bc-RH50: 5'-GTGGCTCTGAAAAGAGC

CTTTGAGTTTTAAAGCACCTAAGCACACATTTACTTGTACAGCTCGTCCA

Figure 3C:
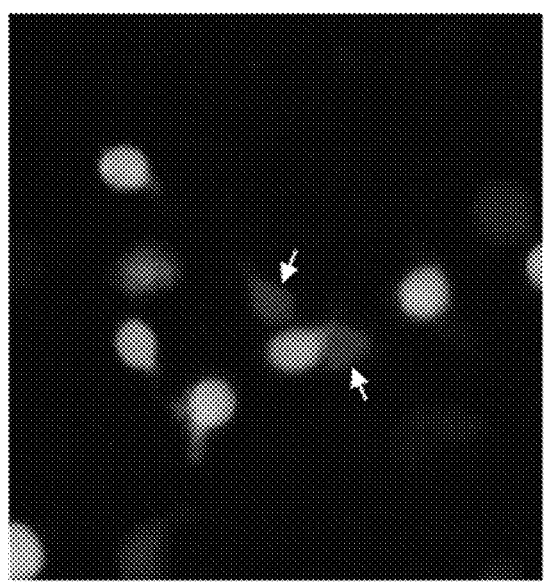
FIG. 3c shows the fluorescence image of live HEK293 cells expressing Histone 2Bc-mCherry fusion protein 72 hours post transfection of human ANAGO derived from NgAgo a and donor fragment.

TGC-3' (SEQ ID NO: 20))

that incorporated 50 bp of H2Bc sequence as flanking arm on each side of the amplified mCherry fragment. The insertion of donor fragment would result in the in-frame fusion of mCherry open reading frame (ORF) to the last codon of H2Bc (FIG. 3a). The precise integration was detected by genomic PCR reactions with primer pairs H2Bc-F1/mCherry-Rev (H2Bc-F1: 5'-TAACGACATCTTC-GAGCGCA-3' (SEQ ID NO: 21); and mCherry-Rev: 5'-TACGACACTGCATTACGGGG-3' (SEQ ID NO: 22)) and mCherry-For/H2Bc-R1 (mCherry-For: 5'-CCTTTC-CCACAACGAGGACT-3' (SEQ ID NO: 8); and H2Bc-R1: 5'-TGTGAGACTTGAGTGGCTCTG-3' (SEQ ID NO: 23)) that amplified the 5' and 3' junctional regions respectively. The three human ANAGO constructs (NLS-NgAgo ORF, HA-NLS-PfAgo ORF, and HA-NLS-TtAgo ORF) were all able to facilitate the precise knock-in of mCherry in Histon 2Bc (FIG. 3b). Moreover, the expression of H2Bc-mCherry fusion protein was observed in live cells 72 hours post transfection (FIG. 3c).

Example 4. Human CD274/PD-L1

High expression of PD-L1, which is also known as CD274, has been associated with tumor cells in advanced stage tumors such as liver cancer (Xu Y, Poggio M, Jin H Y, etc. (2019) Translation control of the immune checkpoint in cancer and its therapeutic targeting. Nature Medicine, 25, 301-311). PD-L1 blockade is a potential form of cancer immunotherapy. It aims to disrupt the activation of the PD-1/PD-L1 axis, which is likely to serve as a mechanism for tumor evasion of host tumor antigen-specific T-cell immunity. In this example, we explored the possibility to inactivate PD-L1 permanently in a tumor cell by AISE approach. A single-stranded oligo CD274-HDR1 72mer donor molecule (5'-GTGAAATTGCAGGATGCAGGGGTGTACCGC<u>AAGCTTGCTAGC</u>GCAT GATCAGCTATGGTGGTGCCGACTACA-3' (SEQ ID NO: 24))

was designed to introduce a premature stop codon as well as Hind III and NheI sites into the exon 3 region of human CD274 gene (FIG. 4a). We co-transfected donor DNA and plasmid DNA of a humanized ANAGO expression construct into HEK293 cells. The genomic DNA of transfected cells was harvested at 96 hours post transfection. The genomic region containing the entire exon 3 was amplified by PCR with a pair of specific primers (CD274-F3: 5'-AGCATT-TACTGTCACGGTTCCC-3' (SEQ ID NO: 25) and CD274-R2: 5'-AAAGATCAGGCCTCTCATCTATAA-3' (SEQ ID NO: 26)) for amplicon deep-sequencing (GeneWiz, New Jersey). The data analysis revealed that over 18% reads showed the on-target HDR editing in the exon 3 of CD274 gene in HEK293 cells transfected with the human ANAGO construct derived from PfAgo sequence (FIG. 4b).

Figure 4C:
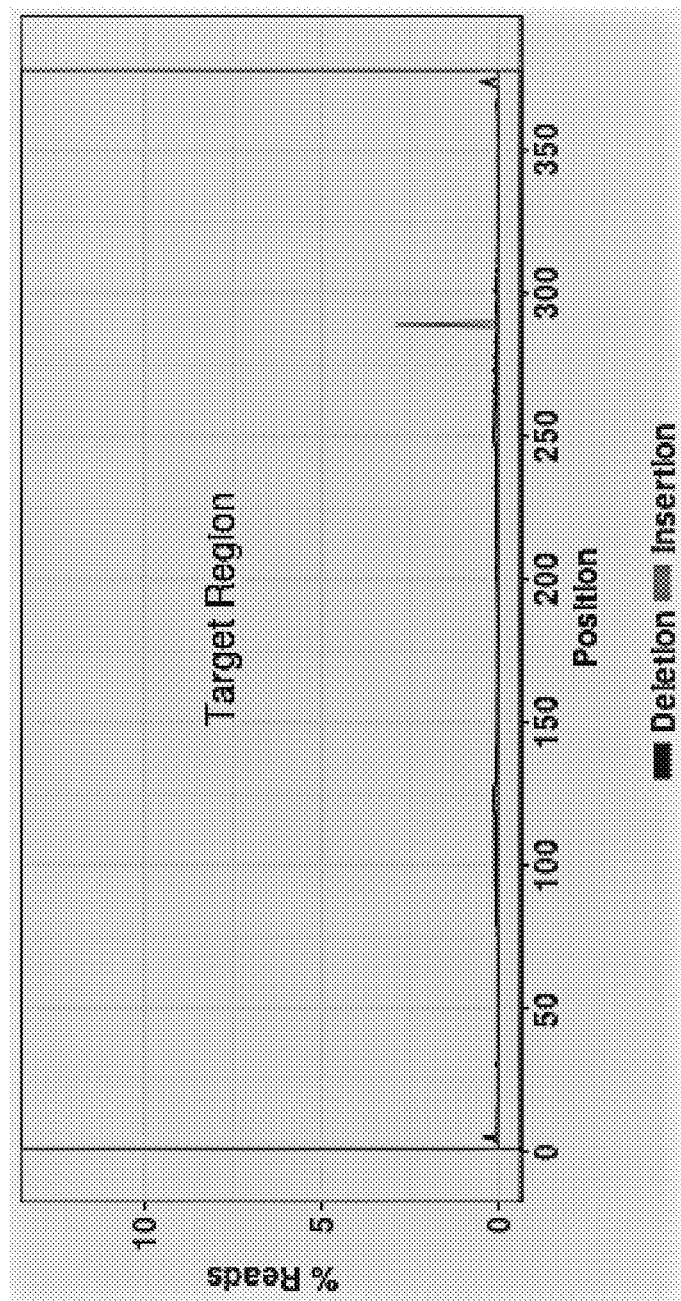
FIG. 4c shows the graphic representation of ultra-deep sequencing result of PCR amplicon products for the target genomic region when a guide molecule is also present.

In order to evaluate the difference between the AISE with both a guide molecule and a donor molecule and the AISE with a donor molecule alone without a guide molecule, a separate comparison experiment under the same condition as above with the exception of the addition of a guide molecule (5'-TGCAGGGGTGTACCGCTGCATGAT-3' (SEQ ID NO: 27)) that is targeted to the desired mutation site (FIG. 4c) in the presence of the donor molecule described above. In this case, the deep-sequencing data analysis revealed that only 2.7% of the reads showed the desired on-target HDR editing in the exon 3 of CD274 gene in HEK293 cells transfected with the human ANAGO construct derived from PfAgo sequence (FIG. 4c).

Based on the above results, the percentage of the total HDR and/or the precise HDR using AISE in the presence of both a guide molecule and a donor molecule was significantly reduced as compared to that of the AISE using a donor molecule alone without a guide molecule, >18% vs 2.7% respectively. These results clearly demonstrate that not only is a guide molecule not required for ANAGO-induced precise genomic sequence editing (AISE), but also the addition of a guide molecule in the AISE system may lead to significantly lower percentage of desired HDR as compared to AISE system with a donor molecule alone without a guide molecule. These data showed feasibility of using the AISE technology disclosed herein without a guide molecule to enhance natural immune response by inactivating PD-L1 gene in tumor tissues, and apparent advantages without using a guide molecule.

Perspectives of AISE Technology or Approach

Unlike Cas proteins, which only exist in prokaryotes, Argonaute proteins are conserved through evolution and can be identified in virtually all species. In mammalian cells, endogenous Argonaute proteins are considered to be a major component of the RNA-induced silencing complex (RISC), which mediates RNA interference. Argonaute uses a micro RNA (22 nt) as a guide for identifying complementary target mRNA. Interestingly, an evolutionarily related enzyme in prokaryotes, Argonaute of the bacterium *Thermus thermophiles* (TtAgo), was found to be able to use DNA-guided DNA interference as a defense mechanism to protect its host against foreign DNA. TtAgo bound with 5'-phosphorylated single-stranded DNA guide (13-25 nucleotides in length), effectively cleaved a foreign complementary DNA in vivo. Previously, we were among the pioneers who had utilized gene swamping experiments to demonstrate that evolutionarily conserved proteins, such as homeodomain-containing proteins, were not only conserved in structures, but also could functionally act in a similar fashion in a species that was diverged from a common ancestor over millions of years ago (Zhao J J, Lazzarini R A, Pick L. The mouse Hox-1.3 gene is functionally equivalent to the *Drosophila* Sex combs reduced gene. Genes Dev. 1993, 7: 343-354).

As shown herein the gene sequences of *Natronobacterium gregoryi* [NgAgo], *Pyrococcus furiosus* [PfAgo], *Thermus thermophilus* [TtAgo], *Thermus thermophilus* [TtAgo], and *Methanocaldococcus jannaschii* [MjAgo] were modified to that of SEQ ID NO:1, SEQ ID NO:2, SEQ ID NO:3, SEQ ID NO:4 correspondingly. These modifications resulted in enhanced expressions and/or activities of these human ANAGO in human cells. The human ANAGO described herein acts as a DNA directed gene editing nuclease in human cells.

The gene sequences of other microbial argonaute proteins, such as *Clostridium butyricum* [CbAgo], and *Limnothrix rosea* [LrAgo] may be also engineered in a similar fashion to generate species-specific ANAGO to eukaryotes for gene editing in eukaryotic cells, such as human cells.

The AISE technology described herein shall have at least following distinctive advantages over RNA-guided CRISPR/Cas approach:

1) The homology-directed repair or replacement (HDR) of AISE approach generally lead to measurable to high percentage of HDR editing event with superior precision, speed, and throughput, and without concerning about off-target effect. It is unlike the non-homologous end-joining (NHEJ)-mediated gene editing, which is error-prone and mainly utilized in CRISPR/Cas system.

2) A very versatile donor molecule, with either single-stranded or double-stranded, can be used in the ANAGO induced gene editing. The donor nucleic acid can accommodate as minimal as a single base change or as long as at least 1500 nucleotides of exogenous sequence. In fact, it has been reported recently that single-stranded oligodeoxy-nucleotides (ssODNs)-mediated knock-in of a donor fragment in mammalian cells occurs via HDR and is more efficient than using a double-stranded donor fragment.

3) ANAGO proteins are much smaller than a Cas nuclease. It is easy to fit into an adeno-associated viral (AAV) vector, a very promising tissue delivery system for clinical applications.

Unlike the CRISPR/Cas system, the precise genomic sequence editing using the AISE technology described herein has none or very low imprecise editing, since the AISE technology is mainly depended on homology directed recombination. The imprecise editing associated with AISE can be as low as about 0%, about 0.5%, about 1.3%, about 0%-6%, about 0%-5%, about 0%-0.1%, about 0.1%-6%, about 0.1%-5%, about 0.1%-4%, about 0.1%-3%, about 0.1%-2%, about 0.1%-1%, about 0%-1%, about 0%-2%, about 0%-3%, about 0%-4%, about 0%-0.5%, about 0.5%-1%, about 1%-1.5%, about 1.5%-2%, about 2%-2.5%, about 2.5%-3%, about 3%-3.5%, about 3.5%-4%, about 4%-4.5%, about 4.5%-5%, about 5%-5.5%, or about 5.5%-6% of the genomic PCR products, or any percentage in a range bounded by any of the above values. The AISE technology with very low or none imprecise editing provides a very powerful and desirable tool for precise genomic sequence editing, which enables wide applications using AISE to treat many gene associated diseases, disorders, or conditions, both known or yet to be known.

Furthermore, the AISE technology described herein has very low rate of the unintended indel events including both unintended deletion and unintended insertion at or around the target region, such as about 0%-2%, about 0%-0.1%, about 0.1%-2%, about 0%-1%, about 0.1%-1%, about 1%-2%, about 1%-1.5%, about 1.5%-2%, about 0%-0.1%, about 0%-0.5%, about 0.5-1%, about 0.1%, about 0.2%, about 0.3%, about 0.4%, about 0.5%, about 0.6%, about 0.7%, about 0.8%, about 0.9%, or about 1%, or any percentage in a range bounded by any of the above values.

The rate of the unintended sequence insertion event at or around the target region associated with AISE is very low, such as about 0%-2%, about 0%-0.1%, about 0.1%-2%, about 0%-1%, about 0.1%-1%, about 1%-2%, about 1%-1.5%, about 1.5%-2%, about 0.1%-2%, about 0.1%-1%, about 0.1%-0.5%, about 0.5%-1%, about 0.1%-0.3%, about 0.3%-0.5%, about 0.5%-0.7%, about 0.7%-0.9%, about 0.9%-1%, about 0.2%-0.4%, about 0.4%-0.6%, about 0.6-0.8%, about 0.8%-1.0%, about 0.1%, about 0.2%, about 0.25%, about 0.3%, about 0.4%, about 0.5%. about 0.55%, about 0.6%, about 0.7%, about 0.8%, about 0.9%, or about 1%, or any percentage in a range bounded by any of the above values.

The rate of the unintended sequence deletion event at or around the target region associated with AISE is very low, such as about 0%-2%, about 0%-0.1%, about 0.1%-2%, about 0%-1%, about 0.1%-1%, about 1%-2%, about 1%-1.5%, about 1.5%-2%, about 0.1%-2%, about 0.1%-1%, about 0.1%-0.5%, about 0.5%-1%, about 0.1%-0.3%, about 0.3%-0.5%, about 0.5%-0.7%, about 0.7%-0.9%, about 0.9%-1%, about 0.2%-0.4%, about 0.4%-0.6%, about 0.6-0.8%, about 0.8%-1.0%, about 0.1%, about 0.2%, about 0.25%, about 0.3%, about 0.4%, about 0.5%. about 0.55%, about 0.6%, about 0.7%, about 0.8%, about 0.9%, or about 1%, or any percentage in a range bounded by any of the above values.

The very low rate or none of unintended indel events associated with the AISE technology provides a very significant benefit in eliminating or significantly reduce the risks associated with the unintended indel events in gene therapy. Thus, AISE technology described herein could benefit a huge population of patients who have gene associated diseases, disorders, or conditions, both known or yet to be known.

The rate of the homologous directed replacement (HDR %) of the on-target integration of donor sequence detected with various methods using different human ANAGO are varied for different targets. The HDR % can be about 1%-100%, about 1%-95%, about 1%-90%, about 1%-80%, about 1%-70%, about 1%-60%, about 1-50%, about 1-5%, about 5-10%, about 10-15%, about 15-20%, about 20-30%, about 30-40%, about 40-50%, about 50-60%, about 2-4%, about 4-6%, about 6-8%, about 8-10%, about 10-20%, about 10-30%, about 30-50%, about 1%, about 3%, about 4%, about 4.2%, about 7.1%, about 10.3%, about 18%, about 19.5%, about 23.5%, about 32%, about 43%, at least 3%, at least 4%, at least 5%, at least 7%, at least 10%, at least 15%, at least 18%, at least 20%, at least 30%, or at least 40%, or any HDR % in a range bounded by any of the above values for the genomic PCR products of the cells transfected with various human ANAGO expression constructs. The fact that some embodiment using the AISE described herein has demonstrated 43% HDR of precise sequence editing indicating tremendous potential of AISE in gene therapy. The ability to manipulate any genomic sequence by AISE technology described herein may have far-reaching implications and opportunities in developing new treatments for many different human diseases and disorders. Some major applications contemplated herein are:

Cellular Immunotherapy

Cancer immunotherapy involves or uses components of the immune system such as antibodies and T cells to treat cancer patients. Recently, impressive treatment results have been reported in some cases of lymphoma, leukemia and melanoma with adoptive T-cell immunotherapy, in which autologous T cells are engineered to attack cancer antigen ex vivo and transferred back to the patient. The T-cell immunotherapy could be further enhanced via expressing synthetic receptors known as chimeric antigen receptors, or CARs, and knocking out the endogenous T-cell receptors with engineered nucleases such as the human ANAGO described herein. In addition, knocking out the human leukocyte antigen (HLA) via gene editing could avoid immune rejection of allogeneic cell therapy and offer a universal off-the-shelf cell therapy product.

Another useful application is to increase T-cell effector function and broadly enabling immunotherapy for diverse cancer types by knocking out genes of checkpoint inhibitor pathways such as CD274/PD-L1 (see the example 4 above) and CTLA-4.

Germline and Embryonic Engineering

Cystic fibrosis (CF) is a hereditary disease that affects the lungs and digestive system. The body produces thick and sticky mucus that can clog the lungs and obstruct the pancreas. Cystic fibrosis can be life-threatening, and people with the condition tend to have a shorter-than-normal life span. Cystic Fibrosis is caused by any one or combination of numerous mutations affecting the function of the Cystic Fibrosis Transmembrane Conductance Regulator (CFTR). Currently, there is no cure for the disease, but the symptoms can be mitigated through therapy. Mutations can affect different parts of the pathway thereby leading to distinct natural history and calling for unique therapies. In all cases, gene-editing to correct the mutation before a child is born would greatly increase the quality of life of the future child. Under the responsible ethical guidance, the AISE technology would be a method of choice for gene-editing in these cases because it can work easily in germ cells or fertilized eggs, has minimal off-target effects, and can easily correct simple mutations via homologous recombination. For example, if a set of germ cells or fertilized eggs are sequenced in vitro and found to have the F508del mutation, the CFTR misfolding that would be expected to occur can be reverted to normal form by using ANAGO mediated precise gene-editing technology.

Optogenetics

Optogenetics is a research tool that is commonly found in neuroscience laboratories. In this context, the ability of Argonaute to swap out large loci such as mCherry (700 base pairs) can be fully taken advantage of. Mice in optogenetics experiments are bred to have a genetic cassette containing ion channels possessing a light sensitive property. Rhodopsins are generally used as the light sensitive segment. Viral vehicles are typically used to deliver the gene engineering tool to introduce the channel Rhodopsin, flanked by a promoter, to the cell types of interest. In this case, ANAGO in a form of RNA could be placed in the viral capsid and injected into the portion of the mouse brain that is under study. The genetic engineering can also be done upstream in the germline cells of an animal model, and application for which AISE technology would equally be well-suited. A probe with the capability of delivering targeted beams of light is then inserted into the animal brain (a probe containing an optic fiber, commonly). Once the rig is cemented in place, researchers can toggle the light between on and off and change the activity of the neurons in different settings, environments, and in the presence of novel stimuli. Thus, ANAGO mediated gene editing technology has the ability of accelerating discoveries in the realm of neuroscience.

Antiviral Therapy

Gene editing strategy has been used to remove the integrated viral DNA sequence from a host genome or knock out CCR5, a coreceptor used for primary HIV infection. Currently, several ongoing clinical trials are evaluating this approach in HIV-positive patients. Early study results provide promising proof-of-principle of a gene-editing approach in humans, which show safe engraftment and survival of CCR5-modified T cells and control of viral load in some patients. The ANAGO mediated gene-editing platform could also be applied to attack viral genomes of various DNA viruses such as HIV, hepatitis B virus, herpes simplex virus, and human papilloma virus etc. To circumvent the high mutability of viral targets, several donor molecules could be used simultaneously to target multiple critical sites in the viral genome.

Liver-Targeted Gene Editing

Liver is probably one of the most accessible organs for applying gene-editing technology to treat many different diseases. At one hand, the AISE technology could be used to correct mutations caused severe diseases including clotting disorders such hemophilia A and hemophilia B, as well as lysosomal storage disorders such as Fabry disease, Gaucher disease, Pompe disease, von Gierke disease, and Hurler and Hunter syndromes. On the other hand, the disruption of particular genes in the tissue may also have a beneficial effect. For example, reducing PCSK9 activity is correlated with decreased LDL level. In contrast to continuous administration of PCSK9 inhibitors, a liver-targeted PCSK9 knockout or variant substitutions could lead to long-lasting effect of lowering cholesterol levels.

Blindness Treatment

Another highly accessible organ for applying gene-editing technology is eye. Recent successes in clinical trials for the treatment of Leber Congenital Amaurosis type 2 (LCA2) have raised hope of using gene therapy to treat blindness caused by genetic mutations. LCA is the leading cause of childhood blindness and is caused by mutations in at least 18 different genes. Other autosomal dominant disorders such as forms of retinoblastoma, primary open angle glaucoma, retinitis pigmentosa and Fuchs endothelial corneal dystrophy, could potentially be treated by targeted editing of mutation sites. More importantly, the proven safety of adeno-associated virus (AAV) delivery in eyes and the compact size of the ANAGO system make it a particularly attractive gene-editing strategy in clinical settings.

Broadly speaking, with the advent of the ANAGO mediated precise gene editing technology, manipulating the genome of plants, animals, and particularly human pluripotent stem cells will become an attainable task, allowing to modify a genome with superior precision, speed, and throughput. AISE described herein will revolutionize our scientific communities worldwide for both developing experimental models to understand biological processes and strategies for improving wellness of living organisms.

In certain aspects, the de novo chemically synthesized single stranded oligodeoxynucleotide-mediated sequence replacement protocol described herein can be applied to any target site without addition of a guide molecule, thus simplifying genome engineering in living organisms.

In some embodiments, the nucleic acids, compositions and methods described herein are useful for additional applications, non-limiting examples of which include single and multiplex gene knockouts, conditional gene knockouts, generation of knock-in alleles, introduction of small as well as large genetic modifications, generation of large deletions and chromosome engineering, genome-wide screens, transcriptional regulation, genetic modifications of mitochondrial DNA and target mitochondrial diseases, and the like.

Unless otherwise indicated, all numbers expressing quantities of ingredients, properties such as percentages, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A synthetic nucleic acid comprising:
a first nucleic acid sequence encoding a codon-Adapted Nuclear Argonaute protein (ANAGO) that is a polypeptide capable of editing a target nucleic acid sequence within a human cell in the presence of a donor nucleic acid without a guide nucleic acid, wherein the ANAGO is species-specific to human, wherein the ANAGO is attached to a nuclear localization signal peptide sequence (NLS);
wherein the first nucleic acid sequence is produced by modifying a second nucleic acid sequence of a microbial species, and wherein the second nucleic acid sequence comprises a coding region that is capable of encoding a microbial Argonaute protein that has endonuclease activities in a microorganism;

wherein the modifying comprises replacing microbial preferred codons of the second nucleic acid sequence with codons that have preferential usage in the human cell; and wherein the first nucleic acid sequence comprises at least 85% identity to the nucleic acid sequence of SEQ ID NO:2; SEQ ID NO:3; or SEQ ID NO:4.

2. The synthetic nucleic acid of claim 1, wherein the first nucleic acid sequence comprises the nucleic acid sequence of SEQ ID NO:2.

3. The synthetic nucleic acid of claim 1, wherein the first nucleic acid sequence comprises the nucleic acid sequence of SEQ ID NO:3.

4. The synthetic nucleic acid of claim 1, wherein the first nucleic acid sequence comprises the nucleic acid sequence of SEQ ID NO:4.

5. The synthetic nucleic acid of claim 1, further comprising a promoter operably linked to the first nucleic acid sequence.

6. A composition comprising the synthetic nucleic acid of claim 1, and a donor nucleic acid.

7. The composition of claim 6, wherein the donor nucleic acid comprises:
(i) a nucleic acid sequence to be introduced into the target nucleic acid sequence by the ANAGO;
(ii) a 5'-flanking sequence; and
(iii) a 3'-flanking sequence,
wherein the 5'-flanking sequence and the 3'-flanking sequence independently comprise at least 10 consecutive nucleotides that are at least 90% identical to the target sequence located in the genome of a human cell.

8. The composition of claim 7, wherein the 5'-flanking sequence and the 3'-flanking sequence each contain 10 nucleotides to 500 nucleotides.

9. The composition of claim 7, wherein each of the 5'-flanking sequence and the 3'-flanking sequence comprise at least 10 nucleotides that are identical to the target sequence.

10. A composition comprising the synthetic nucleic acid of claim 1, and one or more of a pharmaceutical acceptable excipient, diluent, additive, or carrier.

11. The composition of claim 7, further comprising a pharmaceutical acceptable excipient.

* * * * *

SEQUENCE LISTING

<160> NUMBER OF SEQ ID NOS: 44

<210> SEQ ID NO 1
<211> LENGTH: 2688
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

| | | | | | |
|---|---|---|---|---|---|
| atggtgccaa | aaaagaagag | aaaggtagcc | accgtgatcg | acctggactc | caccaccacc | 60 |
| gccgacgagc | tgacctccgg | ccacacctac | gacatctccg | tgaccctgac | cggcgtgtac | 120 |
| gacaacaccg | acgagcagca | ccccggatg | tccctggcct | tcgagcagga | caacggcgag | 180 |
| cggcggtaca | tcaccctgtg | aagaacacc | accccaagg | acgtgttcac | ctacgactac | 240 |
| gccaccggct | ccacctacat | cttcaccaac | atcgactacg | aggtgaagga | cggctacgag | 300 |
| aacctgaccg | ccacctacca | gaccaccgtg | gagaacgcca | ccgcccagga | ggtgggcacc | 360 |
| accgacgagg | acgagacctt | cgccggcggc | gagcccctgg | accaccacct | ggacgacgcc | 420 |
| ctgaacgaga | cccccgacga | cgccgagacc | gagtccgact | ccggccacgt | gatgacctcc | 480 |
| ttcgcctccc | gggaccagct | gcccgagtgg | accctgcaca | cctacaccct | gaccgccacc | 540 |
| gacggcgcca | agaccgacac | cgagtacgcc | cggcggaccc | tggcctacac | cgtgcggcag | 600 |
| gagctgtaca | ccgaccacga | cgccgccccc | gtggccaccg | acggcctgat | gctgctgacc | 660 |
| cccgagcccc | tgggcgagac | cccctggac | ctggactgcg | gcgtgcgggt | ggaggccgac | 720 |
| gagacccgga | ccctggacta | caccaccgcc | aaggaccggc | tgctggcccg | ggagctggtg | 780 |
| gaggagggcc | tgaagcggtc | cctgtgggac | gactacctgg | tgcggggcat | cgacgaggtg | 840 |
| ctgtccaagg | agcccgtgct | gacctgcgac | gagttcgacc | tgcacgagcg | gtacgacctg | 900 |
| tccgtggagg | tgggccactc | cggccgggcc | tacctgcaca | tcaacttccg | gcaccggttc | 960 |
| gtgcccaagc | tgaccctggc | cgacatcgac | gacgacaaca | tctaccccgg | cctgcgggtg | 1020 |
| aagaccacct | accggccccg | gcggggccac | atcgtgtggg | gcctgcggga | cgagtgcgcc | 1080 |
| accgactccc | tgaacaccct | gggcaaccag | tccgtggtgg | cctaccaccg | gaacaaccag | 1140 |
| accccccatca | acaccgacct | gctggacgcc | atcgaggccg | ccgaccggcg | ggtggtggag | 1200 |
| acccggcggc | agggccacgg | cgacgacgcc | gtgtccttcc | ccaggagct | gctggccgtg | 1260 |
| gagcccaaca | cccaccagat | caagcagttc | gcctccgacg | gcttccacca | gcaggcccgg | 1320 |
| tccaagaccc | ggctgtccgc | ctcccggtgc | tccgagaagg | cccaggcctt | cgccgagcgg | 1380 |
| ctggaccccg | tgcggctgaa | cggctccacc | gtggagttct | cctccgagtt | cttcaccggc | 1440 |
| aacaacgagc | agcagctgcg | gctgctgtac | gagaacggcg | agtccgtgct | gaccttccgg | 1500 |
| gacggcgccc | gggcgccca | ccccgacgag | accttctcca | agggcatcgt | gaaccccccc | 1560 |
| gagtccttcg | aggtggccgt | ggtgctgccc | gagcagcagg | ccgacacctg | caaggcccag | 1620 |
| tgggacacca | tggccgacct | gctgaaccag | gccggcgccc | ccccaccccg | gtccgagacc | 1680 |
| gtgcagtacg | acgccttctc | ctcccccgag | tccatctccc | tgaacgtggc | cggcgccatc | 1740 |
| gaccccctccg | aggtggacgc | cgccttcgtg | gtgctgcccc | ccgaccagga | gggcttcgcc | 1800 |
| gacctggcct | cccccaccga | gacctacgac | gagctgaaga | aggccctggc | caacatgggc | 1860 |
| atctactccc | agatggccta | cttcgaccgg | ttcgggacg | ccaagatctt | ctacacccgg | 1920 |
| aacgtggccc | tgggcctgct | ggccgccgcc | ggcggcgtgg | ccttcaccac | cgagcacgcc | 1980 |

```
atgcccggcg acgccgacat gttcatcggc atcgacgtgt cccggtccta ccccgaggac    2040
ggcgcctccg gccagatcaa catcgccgcc accgccaccg ccgtgtacaa ggacggcacc    2100
atcctgggcc actcctccac ccggccccag ctgggcgaga agctgcagtc caccgacgtg    2160
cgggacatca tgaagaacgc catcctgggc taccagcagg tgaccggcga gtcccccacc    2220
cacatcgtga tccaccggga cggcttcatg aacgaggacc tggaccccgc caccgagttc    2280
ctgaacgagc agggcgtgga gtacgacatc gtggagatcc ggaagcagcc ccagacccgg    2340
ctgctggccg tgtccgacgt gcagtacgac accccgtga agtccatcgc cgccatcaac    2400
cagaacgagc ccgggccac cgtggccacc ttcggcgccc ccgagtacct ggccacccgg    2460
gacggcggcg gcctgccccg gcccatccag atcgagcggg tggccggcga ccgacatc     2520 gagaccctga cccggcaggt gtacctgctg tcccagtccc acatccaggt gcacaactcc    2580 accgccggc tgcccatcac caccgcctac gccgaccagg cctccaccca cgccaccaag    2640
ggctacctgg tgcagaccgg cgccttcgag tccaacgtgg gcttcctg                2688

<210> SEQ ID NO 2
<211> LENGTH: 2364
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggtgtacc cctacgacgt gcccgactac gccccaaaaa agaagagaaa ggtagccaag      60
gccaaggtgg tgatcaacct ggtgaagatc aacaagaaga tcatccccga caagatctac     120
gtgtacagac tgttcaacga ccccgaggag gagctgcaga aggagggcta cagcatctac     180
agactggcct acgagaacgt gggcatcgtg atcgacccg agaacctgat catcgccacc      240
accaaggagc tggagtacga gggcgagttc atccccgagg gcgagatcag cttcagcgag     300
ctgagaaacg actaccagag caagctggtg ctgagactgc tgaaggagaa cggcatcggc     360
gagtacgagc tgagcaagct gctgagaaag ttcagaaagc ccaagacctt cggcgactac     420
aaggtgatcc ccagcgtgga gatgagcgtg atcaagcacg acgaggactt ctacctggtg     480
atccacatca tccaccagat ccagagcatg aagaccctgt gggagctggt gaacaaggac     540
cccaaggagc tggaggagtt cctgatgacc acaaggagaa acctgatgct gaaggacatc     600
gccagccccc tgaagaccgt gtacaagccc tgcttcgagg agtacaccaa gaagcccaag     660
ctggaccaca ccaggagat cgtgaagtac tggtacaact accacatcga gagatactgg      720
aacacccccg aggccaagct ggagttctac agaaagttcg ccaggtgga cctgaagcag      780 cccgccatcc tggccaagtt cgccagcaag atcaagaaga caagaacta caagatctac      840 ctgctgcccc agctggtggt gcccacctac aacgccgagc agctggagag cgacgtggcc     900
aaggagatcc tggagtacac caagctgatg cccgaggaga aaggagct gctggagaac       960 atcctggcc aggtggacag cgacatcatc gacaagagcc tgagcgagat cgaggtggag    1020
aagatcgccc aggagctgga gaacaagatc agagtgagag cgacaagggg caacagcgtg    1080
cccatcagcc agctgaacgt gcagaagagc cagctgctgc tgtggaccaa ctacagcaga    1140 aagtacccc tgatcctgcc ctacgaggtg cccgagaagt tcagaaagat cagagagatc      1200
cccatgttca tcatcctgga cagcggcctg ctggccgaca tccagaactt cgccaccaac    1260
gagttcagag agctggtgaa gagcatgtac tacagcctgg ccaagaagta caacagcctg    1320
```

| | |
|---|---|
| gccaagaagg ccagaagcac caacgagatc ggcctgccct tcctggactt cagaggcaag | 1380 |
| gagaaggtga tcaccgagga cctgaacagc gacaagggca tcatcgaggt ggtggagcag | 1440 |
| gtgagcagct tcatgaaggg caaggagctg ggcctggcct tcatcgccgc cagaaacaag | 1500 |
| ctgagcagcg agaagttcga ggagatcaag agaagactgt tcaacctgaa cgtgatcagc | 1560 |
| caggtggtga cgaggacac cctgaagaac aagagagaca agtacgacag aaacagactg | 1620 |
| gacctgttcg tgagacacaa cctgctgttc caggtgctga gcaagctggg cgtgaagtac | 1680 |
| tacgtgctgg actacagatt caactacgac tacatcatcg gcatcgacgt ggcccccatg | 1740 |
| aagagaagcg agggctacat cggcggcagc gccgtgatgt cgacagcca gggctacatc | 1800 |
| agaaagatcg tgcccatcaa gatcggcgag cagagaggcg agagcgtgga catgaacgag | 1860 |
| ttcttcaagg agatggtgga caagttcaag gagttcaaca tcaagctgga caacaagaag | 1920 |
| atcctgctgc tgagagacgg cagaatcacc aacaacgagg aggagggcct gaagtacatc | 1980 |
| agcgagatgt tcgacatcga ggtggtgacc atggacgtga tcaagaacca ccccgtgaga | 2040 |
| gccttcgcca acatgaagat gtacttcaac ctgggcggcg ccatctacct gatcccccac | 2100 |
| aagctgaagc aggccaaggg cacccccatc cccatcaagc tggccaagaa gagaatcatc | 2160 |
| aagaacggca aggtggagaa gcagagcatc accagacagg acgtgctgga catcttcatc | 2220 |
| ctgaccagac tgaactacgg cagcatcagc gccgacatga gactgcccgc ccccgtgcac | 2280 |
| tacgcccaca agttcgccaa cgccatcaga acgagtgga agatcaagga ggagttcctg | 2340 |
| gccgagggct tcctgtactt cgtg | 2364 |

<210> SEQ ID NO 3  
<211> LENGTH: 2109  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 3

| | |
|---|---|
| atggtctacc cctacgacgt gccagattac gcccctaaga aaaagcggaa ggtggccaac | 60 |
| cacctgggca agacagaggt gttcctgaac agattcgccc tgcggcctct gaaccctgag | 120 |
| gaactcagac cttggcggct ggaagtggtg ctggatcctc cacctggacg cgaggaagtg | 180 |
| tatcctctgc tggctcaagt ggctcggaga gctggcggag tgacagttag aatgggagat | 240 |
| ggcctggcca gctggtcccc acctgaagtt cttgtgctgg aaggcacccT ggccagaatg | 300 |
| ggccagacat acgcctaccg gctgtacccc aaaggcagaa ggcctctgga tcccaaggat | 360 |
| cccggcgaga gatctgtgct gtctgccctg gctagacggc tgctgcaaga gagactgaga | 420 |
| aggctcgaag gcgtgtgggt ggaaggactg gccgtgtaca aagagagca cgccagagga | 480 |
| cctggctggc gagttcttgg cggagctgtt ctggatctgt gggtgtcaga tagcggcgcc | 540 |
| tttctgctgg aagtcgaccc cgcctataga atcctgtgcg agatgagcct ggaagcttgg | 600 |
| ctggctcagg acacccctct gcctaaaaga gtgcggaacg cctacgacag acggacctgg | 660 |
| gaactgctga ctgggcga agaggacccc aaagaacttc ctctgcctgg cggactgagc | 720 |
| ctgctggatt accacgcctc taagggcaga ctgcaggca gagaaggtgg aagagtggcc | 780 |
| tgggttgccg atcctaagga ccccagaaag cccattcctc acctgacagg actgctggtg | 840 |
| cctgtgctga ccctggaaga tctgcacgag aagagggat ctctgccct gtctctgcct | 900 |
| tgggaagaga gaagaaggcg gaccagagag atcgccagct ggatcggaag aaggcttggc | 960 |

```
ctgggaacac ctgaggctgt tagagcccag gcctacagac tgagcatccc caagctgatg      1020
ggccgcagag ccgtgtctaa acctgccgat gctctgagag tgggcttcta cagagcccaa      1080
gagacagccc tggctctgct cagacttgat ggcgctcaag gctggcccga gtttctgaga      1140
agggctctgc tgagagcctt tggagcctct ggcgcttctc tgagactgca cacactgcac      1200
gcccatcctt ctcagggcct cgcctttaga gaggctctga aaaggccaa agaagagggc       1260 gttcaggccg tgctggttct gacacctcct atggcatggg aagatcggaa ccggctgaaa      1320
gccctgctgc tcagagaggg actgcctagc cagatcctga acgtgcccct gagagaagag      1380
gaacggcaca gatgggagaa tgccctgctg ggcctgctgg ccaaagctgg acttcaagtg      1440
gttgccctgt ccggcgccta tcctgctgaa ctggctgtgg gatttgacgc tggcggcaga      1500
gagagcttca gatttggagg cgctgcttgt gccgttggcg agatggtgg acatctgctg       1560 tggacactgc ctgaagctca ggccggcgaa agaatccctc aagaggtcgt gtgggacctg      1620
ctcgaagaaa ccctgtgggc cttcagaaga aggccggca ggctgccttc aagagtgctg       1680
ctcctgagag atggcagagt gccccaggat gagtttgccc tggcactgga agccctggca      1740
agagagggaa ttgcctacga cctggtgtcc gtgcggaaat ctggtggcgg aagagtgtac      1800
cccgtgcaag gcagactggc cgatggactg tatgtgcctc tggaagataa gaccttcctg      1860
ctgctgaccg tgcaccggga ctttagaggc acacccagac tctgaagct ggtgcatgaa       1920 gccggcgaca cacctctcga agctctggcc caccagatct ttcacctgac agactgtac      1980 cccgccagcg gctttgcctt tcctagactg cctgctcctc tgcacctggc cgacagactg      2040
gtcaaagaag tgggccgcct gggcatcaga cacctgaaag aggtggaccg cgagaagctg      2100
ttcttcgtg                                                             2109

<210> SEQ ID NO 4
<211> LENGTH: 2202
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atggtctacc cctacgacgt gccagattac gcccctaaga aaaagcggaa ggtggccttt       60
accatggtgc tgaacaaagt gacctacaag atcaacgcct ataagatcaa agaggaattc      120
atccccaaag aggtgcactt ctaccggatc aagagcttcg tgaacgaggc cttcaacttc      180
tacagattcg tgaacttcta cggcggcatg atcatcaaca gaaagacaa gtccttcgtg       240 ctgcccctaca aggtggacaa caaggtgctg aagtacaagg acggcaacaa cgagatcccc     300
atcgacatcg agtacatcaa gagcctgaag ctcgagtacg tgaagcccga gatcgccgag     360
aagcttgtgc ggggctatct gaagtccgtg cacaagatcg agcccgagct gagccggatc      420
atcaagaaca tccggaagca caaggtggtg gaaaacatca aggtggaaag ctactgcgag      480
tacgaagtga agaagcacga cggcgactac tacctgatcc tgaacttcag acacaccgcc      540
agcatcacca gcacctgtg gacttcgtg aatagagaca aggccctgct ggaagagtac       600
gtgggcaaga agatcatctt caagcccaat cctaaagtgc ggtacaccat cagcctggtg     660
gacgccccaa atcctcagaa atcgaggaa atcatgagcc acatcatcaa gtactacaag      720
tggagcgagg acatggtcaa gagcaccttc ggcgagatcg actacaacca gcctatcatg      780
tactgcgagg aaattctgga acccttcgca ccccagttct gcaacctggt gttctacatg      840
```

```
gacgagctgg acagctacat cctgaaagag ctgcagagct actggcggct gagcaacgag    900
aacaagggca agatcattaa cgagattgcc aagaaactgc ggttcatcga caacacgccc    960
aaagaactgg aattcatgaa gttcaacaac accccgctgc tggtcaagga cgtgaacaag   1020
aaccccacca agatctacag caccaacaca ctgttcacct ggatctacaa tcagaacgcc   1080
aaaatctacc tgccttacga cgtccccgag atcatccgga caagaatct gctgacctac    1140 atcctcatcg acgaagagat caaggatgag ctgaaggcca tcaaggacaa agtcaacaag   1200
atgttccgca actacaacaa gatcgccaac aagaccgagc tgcccaagtt caactacgcc   1260
aaccggtgga agtactttag caccgacgac atccggggca tcatcaaaga gattaagagc   1320
gagttcaacg acgagatctg cttcgccctg atcatcggca agagaagta taaggacaac    1380 gattactacg agatcctcaa gaagcagctg ttcgacctga agattatcag ccagaacatc   1440
ctgtgggaga actggcggaa ggacgacaag ggctacatga ccaacaacct gctgatccag   1500
atcatgggca agctgggcat caagtatttc atcctggaca gcaagaccc gtacgactac    1560 atcatgggcc tcgatacagg cctgggcatc ttcggcaatc acagagtcgg cggctgtacc   1620
gtggtgtacg atagcgaggg aaagatccgg cggatccagc aatcgagac accagctcca    1680 ggcgagagac tgcatctgcc ctacgtgatc gagtacctgg aaaacaaggc caacatcgac   1740
atggaaaaca aaacatcct gttcctccgc gacggcttca tccagaacag cgagcggaac    1800
gatctgaaag agatcagcaa agagctgaac agcaatatcg aagtgatctc tattcggaag   1860
aacaacaagt acaaagtgtt caccagcgac tacaggatcg gcagcgtgtt cggcaacgac   1920
ggcatcttcc tgcctcacaa gacccctttc ggcagcaacc tgtgaagct gagcacctgg    1980 ctgagattca actgcggcaa cgaggaaggc ctgaaaatca cgagagcat catgcagctg    2040 ctgtacgatc tgaccaagat gaactacagc gccctgtacg gcgagggcag ataccctgaga   2100 atccccgctc ctatccacta cgccgacaag ttcgtgaagg ccctgggcaa aaactggaag   2160
atcgacgagg aactgctgaa gcacggcttt ctgtacttca tc                      2202

<210> SEQ ID NO 5
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cctgcaggcc caggctgcct gccggggata cctcaccaag atcctgcatg ccttccatgg    60
ccttcttcct                                                          70

<210> SEQ ID NO 6
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 ggcagggtc tgcacccggg agccccgtt ctaagctttc actgagttca tgacctacgg      60
gaacctcctg                                                          70

<210> SEQ ID NO 7
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgggtcccgc gggcgcccgt gcgc                                           24

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctttcccac aacgaggact                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgagaatacc tccgcccctt                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10 gcttttggt ccgcatttgg                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggctctaccc ctagctgtct                                                20

<210> SEQ ID NO 12
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tctctggctt ctgcaggcct tgaagttgcc ccatgtcgac tagatctagg aggactcctc    60
tgtctttgcc cagagcatcc cgtggaacc                                      89

<210> SEQ ID NO 13
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgtgttgca gggatatggg                                              20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
catttgtggg gcaacaggaa g                                            21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcgtctgaat tctgtggcag                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctttgccagg agcctagtgt                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttgggaccat gttggaagtt                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agcactgagg ttagaagctg                                              20

<210> SEQ ID NO 19
<211> LENGTH: 68
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
acgcagtgtc cgaaggtacc aaggctgtca ccaagtatac aagctccaag atggtgagca      60
agggcgag                                                               68

<210> SEQ ID NO 20
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtggctctga aaagagcctt tgagttttaa agcacctaag cacacattta cttgtacagc      60
tcgtccatgc                                                             70

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
taacgacatc ttcgagcgca                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tacgacactg cattacgggg                                                  20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgtgagactt gagtggctct g                                                21

<210> SEQ ID NO 24
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gtgaaattgc aggatgcagg ggtgtaccgc aagcttgcta gcgcatgatc agctatggtg      60
```

```
gtgccgacta ca                                                         72
```

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
agcatttact gtcacggttc cc                                              22
```

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
aaagatcagg cctctcatct ataa                                            24
```

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

```
tgcaggggtg taccgctgca tgat                                            24
```

<210> SEQ ID NO 28
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

```
gccggggata cctcaccaag atcctgcatg tcttccatgg ccttcttcct ggcttcctgg     60
tgaagatgag tggcg                                                      75
```

<210> SEQ ID NO 29
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

```
gccggggata cctcaccaag atcctgcatg ccttccatgg ccttcttcct ggcttcctgg     60
tgaagatgag tggcg                                                      75
```

<210> SEQ ID NO 30
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gccggggata cctcaccaag atccgcatgt cttccatggc cttcttcctg gcttcctggt    60
gaagatgagt ggcg    74

<210> SEQ ID NO 31
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gccggggata ctgtcttcca tggccttctt cctggcttcc tggtgaagat gagtggcg    58

<210> SEQ ID NO 32
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: a, c, t, g, unknown or other

<400> SEQUENCE: 32
gccggggata cctcaccaag atcctngcat gtcttccatg gccttcttcc tggcttcctg    60
gtgaagatga gtggc    75

<210> SEQ ID NO 33
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(37)
<223> OTHER INFORMATION: a, c, t, g, unknown or other

<400> SEQUENCE: 33
gccggggata cctcaccaag atcctnnnnn nnnnnnngca tgtcttccat ggcctccttc    60
ctggcttcct ggtga    75

<210> SEQ ID NO 34
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gccggggata cctcaccaag atcgccttct tcctggcttc ctggtgaaga tgagtggcg    59

<210> SEQ ID NO 35
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 35
gccggggata cctcacccat gtcttccatg gccttcttcc tggcttcctg gtgaagatga      60
gtggcg                                                                66

<210> SEQ ID NO 36
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gccggggata cctcatgtct tccatggcct tcttcctggc ttcctggtga agatgagtgg      60
cg                                                                    62

<210> SEQ ID NO 37
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gccggggata cccttcttcc tggcttcctg gtgaagatga gtggcg                    46

<210> SEQ ID NO 38
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(29)
<223> OTHER INFORMATION: a, c, t, g, unknown or other

<400> SEQUENCE: 38
gccggggata cctcaccaag atcctnnnng catgtcttcc atggccttct tcctggcttc      60
ctggtgaaga tgagt                                                      75

<210> SEQ ID NO 39
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gttgccccat gtcgactaca tcgaggagga ctcctctgtc tttgcccaga gcatcccgtg      60
gaacctggag cggat                                                      75

<210> SEQ ID NO 40
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
```

-continued

```
gttgccccat gtcgactaga tctaggagga ctcctctgtc tttgcccaga gcatcccgtg    60
gaacctggag cggat                                                    75

<210> SEQ ID NO 41
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ccgggagccc ccgttctata tcatcactga gttcatgacc tacgggaacc tcctggacta    60
cctgagggag tgcaa                                                    75

<210> SEQ ID NO 42
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ccgggagccc ccgttctaag ctttcactga gttcatgacc tacgggaacc tcctggacta    60
cctgagggag tgcaa                                                    75

<210> SEQ ID NO 43
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ccgggagccc ccgttctata tgttcatgac ctacgggaac ctcctggact acctgaggga    60
gtgcaa                                                              66

<210> SEQ ID NO 44
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, t, g, unknown or other

<400> SEQUENCE: 44
gggtctgcac ccgggagccc ccgttctata tnttcactga gttcatgacc tacgggaacc    60
tcctgg                                                              66
```